(12) United States Patent
Wallach et al.

(10) Patent No.: US 7,354,736 B2
(45) Date of Patent: Apr. 8, 2008

(54) CASPASE-8 BINDING PROTEIN, ITS PREPARATION AND USE

(75) Inventors: David Wallach, Rehovot (IL); Tania Goncharov, Rehovot (IL); Ganesh Kolumam, Bellevue, WA (US); Akhil Rajput, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 74 days.

(21) Appl. No.: 10/488,614

(22) PCT Filed: Sep. 4, 2002

(86) PCT No.: PCT/IL02/00733

§ 371 (c)(1),
(2), (4) Date: Aug. 25, 2004

(87) PCT Pub. No.: WO03/020759

PCT Pub. Date: Mar. 13, 2003

(65) Prior Publication Data

US 2005/0048639 A1    Mar. 3, 2005

(30) Foreign Application Priority Data

Sep. 4, 2001  (IL) ..................... 145278
Oct. 31, 2001 (IL) ..................... 146251
Jan. 6, 2002  (IL) ..................... 147487

(51) Int. Cl.
  *C12P 21/06*   (2006.01)
  *C12N 15/00*   (2006.01)
  *C12N 5/00*    (2006.01)
  *C07H 21/04*   (2006.01)
  *C07K 14/00*   (2006.01)
(52) U.S. Cl. .................. 435/69.1; 435/320.1; 435/325; 536/23.1; 530/350
(58) Field of Classification Search ............... 435/69.1, 435/7.1, 23, 226; 530/350
See application file for complete search history.

(56) References Cited

U.S. PATENT DOCUMENTS

2004/0101927 A9 * 5/2004 Rosen et al. ............... 435/69.1

FOREIGN PATENT DOCUMENTS

WO         WO 9830582 A2 *   7/1998

OTHER PUBLICATIONS

Wang, J., et al. 2001 PNAS 98(24): 13884-13888.*

* cited by examiner

*Primary Examiner*—Karen Cochrane Carlson
*Assistant Examiner*—Marsha Tsay
(74) *Attorney, Agent, or Firm*—Browdy and Neimark, P.L.L.C.

(57) ABSTRACT

The present invention relates to a caspase-8 interacting polypeptide (Cari), methods for its preparation, and its use.

36 Claims, 18 Drawing Sheets

MDFSRNLYDIGEQLDSEDLASLKFLSLDYIPQRKQEPIKDALMLFQRLQEKRMLEESNLS
FLKELLFRINRLDLLITYLNTRKEEMERELQTPGRAQISAYRFHFCRMSWAEANSQCQTQ
SVPFWRRVDHLLIRVMLYQISEEVSRSELRSFKFLLQEEISKCKLDDDMNLLDIFIEMEK
RVILGEGKLDILKRVCAQINKSLLKIINDYEEFSKGEELCGVMTISDSPREQDSESQTLD
KVYQMKSKPRGYCLIINNHNFAKAREKVPKLHSIRDRNGTHLDAGALTTTFEELHFEIKP
HHDCTVEQIYEILKIYQLMDHSNMDCFICCILSHGDKGIIYGTDGQEAPIYELTSQFTGL
KCPSLAGKPKVFFIQACQGDNYQKGIPVETDSEEQPYLEMDLSSPQTRYIPDEADFLLGM
ATVNNCVSYRNPAEGTWYIQSLCQSLRERCPRGDDILTILTEVNYEVSNKDDKKNMGKQM
PQPTFTLRKKLVFPSD

Figure 1

The extent of viability compared with cell treated with Fas ligand alone

| | | |
|---|---:|---|
| p72 | 1 | mslkmdnrdvagkanrwfgvappksgkmnmnilhqeeliaqkkreieakmegkakqnqva |
| THC510568 | 1 | ----argrdvagkanrwfgvappksgkmnmnilhqeeliaqkkreieakmegkakqnqva |
| p72 | 61 | spqpphpgeitnahnsscisnkfandgsflqqflklqkaqtstdaptsapsappstptps |
| THC510568 | 57 | spqpphpgeitnahnsscisnkfandgsflqqfl-------------------------n |
| p72 | 121 | agkrsllisrrtglglaslpgpvksyshakqlpvahrpsvfqspdedeeedyeqwleiky |
| THC510568 | 92 | agkrsllisrrtglglaslpgpvksyshakqlpvahrpsvfqspdedeeedyeqwleiky |
| p72 | 181 | sppegaetrkvieklarfvaeggpbelekvamedykdnpafaflhdknsreflyyrkkvae |
| THC510568 | 152 | sppegaetrkvieklarfvaeggpbelekvamedykdnpafaflhdknsreflyyrkkvae |
| p72 | 241 | irkeaqksqaasqkvsppedeevknlaeklarfiadggpevetialqnnrengafsflye |
| THC510568 | 212 | irkeaqksqaasqkvsppedeevknlaeklarfiadggpevetialqnnrengafsflye |
| p72 | 301 | pnsqgykyyrqkleefrkakasstgsftapdbgfkrksppealsgslppattcpasstpa |
| THC510568 | 272 | pnsqgykyyrqkleefrkakasstgsftapdbgfkrksppealsgslppattcpasstpa |
| p72 | 361 | ptiipapaapgkpasaatvkrkrksrwgpeedkvellpaelvqrdvdaspsplsvqqlkg |
| THC510568 | 332 | ptiipapaapgkpasaatvkrkrksrwgpeedkvelppaelvqrdvdaspsplsvqqlkg |
| p72 | 421 | lgyekgkpvglvgvtelsdaqkkqlkeggemqqmydmimqhkramqdmqllwekavcqhq |
| THC510568 | 392 | lgyekgkpvglvgvtelsdaqkkqlkeggemqqmydmimqhkramqdmqllwekavcqhq |
| p72 | 481 | hgydsdeevdselgtwehqlrrmemdktrewaeqltkmgrgknfigdflppdelekfmet |
| THC510568 | 452 | hgydsdeevdselgtwehqlrrmemdktrewaeqltkmgrgknfigdflppdelekfmet |
| p72 | 541 | fkalkegrepdyseykefkltvenigyqmlnkngwkegeglqseggqiknpvnkgtttvd |
| THC510568 | 512 | fkalkegrepdyseykefkltvenigyqmlnkngwkegeglqseggqiknpvnkgtttvd |
| p72 | 601 | gagfcldrpaelskeddeyeafrkrmmlayrfrpnplnnprrpyy |
| THC510568 | 572 | gagfcldrpaelskeddeyeafrkrmmlayrfrpnplnnprrpyy |

Figure 13

GYEKGKPVGLVGVTEL

Figure 15

CASPASE-8 BINDING PROTEIN, ITS PREPARATION AND USE

FIELD OF THE INVENTION

The present invention relates to a caspase-8 interacting polypeptide (Cari), methods for its preparation, and its use.

BACKGROUND OF THE INVENTION

Tumor Necrosis Factor (TNF-alpha) and Lymphotoxin (TNF-beta) are multifunctional pro-inflammatory cytokines formed mainly by mononuclear leukocytes, which have many effects on cells (Wallach D. (1986); and Beutler and Cerami (1987)). Both TNF-alpha and TNF-beta initiate their effects by binding to specific cell surface receptors. Some of the effects are likely to be beneficial to the organism: they may destroy, for example, tumor cells or virus infected cells and augment antibacterial activities of granulocytes. In this way, TNF contributes to the defense of the organism against tumors and infectious agents and contributes to the recovery from injury. Thus, TNF can be used as an anti-tumor agent in which application it binds to its receptors on the surface of tumor cells and thereby initiates the events leading to the death of the tumor cells. TNF can also be used as an anti-infectious agent.

However TNF-alpha has deleterious effects. There is evidence that overproduction of TNF-alpha may play a major pathogenic role in several diseases. For example, effects of TNF-alpha, primarily on the vasculature, are known to be a major cause for symptoms of septic shock (Tracey et al, 1994). 1994). In some diseases, TNF may cause excessive loss of weight (cachexia) by suppressing activities of adipocytes and by causing anorexia, and TNF-alpha was thus called cachectin. It was also described as a mediator of the damage to tissues in rheumatic diseases (Beutler and Cerami, 1987) and as a major mediator of the damage observed in graft-versus-host reactions (Grau et al, 1989). In addition, TNF is known to be involved in the process of inflammation and in many other diseases.

Two distinct, independently expressed receptors, the p55 (CD120a) and the p75 (CD120b) TNF-receptors, which bind both TNF-alpha and TNF-beta specifically, initiate and/or mediate the above noted biological effects of TNF. These two receptors have structurally dissimilar intracellular domains suggesting that they signal differently (See Hohmann et al, 1989; Engelmann et al, 1990a and b; Brockhaus et al, 1990; Loetscher et al, 1990; Schall et al, 1990; Nophar et al, 1990; Smith et al, 1990). However, the cellular mechanisms, for example, the various proteins and possibly other factors, which are involved in the intracellular signaling of the CD120a and CD120b, have yet to be elucidated. It is intracellular signaling, which occurs usually after the binding of the ligand, i.e., TNF (alpha or beta), to the receptor that is responsible for the commencement of the cascade of reactions that ultimately result in the observed response of the cell to TNF.

As regards the above-mentioned cytocidal effect of TNF, in most cells studied so far, this effect is triggered mainly by CD120a. Antibodies against the extracellular domain (ligand binding domain) of CD120a can themselves trigger the cytocidal effect (see EP 412486) which correlates with the effectiveness of receptor cross-linking by the antibodies, believed to be the first step in the generation of the intracellular signaling process. Further, mutational studies (Brakebusch et al, 1992; Tartaglia et al, 1993) have shown that the biological function of CD120a depends on the integrity of its intracellular domain, and accordingly it has been suggested that the initiation of intracellular signaling leading to the cytocidal effect of TNF occurs as a consequence of the association of two or more intracellular domains of CD120a. Moreover, TNF (alpha and beta) occurs as a homotrimer, and as such, has been suggested to induce intracellular signaling via CD120a by way of its ability to bind to and to cross-link the receptor molecules, i.e., cause receptor aggregation (Engelmann et al 1990b).

Another member of the TNF/NGF superfamily of receptors is the FAS/APO1 receptor (CD95). CD95 mediates cell death in the form of apoptosis (Itoh et al, 1991), and appears to serve as a negative selector of autoreactive T cells, i.e., during maturation of T cells, CD95 mediates the apoptotic death of T cells recognizing self-antigens. It has also been found that mutations in the CD95 gene (lpr) cause a lymphoproliferation disorder in mice that resembles the human cell-surface associated molecule carried by, amongst others, killer T cells (or cytotoxic T lymphocytes—CTLs), and hence when such CTLs contact cells carrying CD95, they are capable of inducing apoptotic cell death of the CD95-carrying cells. Further, monoclonal antibodies have been prepared that are specific for CD95, these monoclonal antibody being capable of inducing apoptotic cell death in cells carrying CD95, including mouse cells transformed by cDNA encoding human CD95 (e.g., Itoh et al, 1991).

TNF receptor and Fas signaling mechanisms comprising the different receptors, their regulation, and the down stream signaling molecules identified are reviewed in detailed by Wallach et al (1999).

It has been found that certain malignant cells and HIV-infected cells carry CD95 on their surface, antibodies against CD95, or the CD95 ligand, may be used to trigger the CD95 mediated cytotoxic effects in these cells and thereby provide a means for combating such malignant cells or HIV-infected cells (see Itoh et al, 1991). Finding yet other ways for enhancing the cytotoxic activity of CD95 may therefore also have therapeutic potential.

It has been a long felt need to provide a way for modulating the cellular response to TNF (alpha or beta) and CD95 ligand. For example, in the pathological situations mentioned above, where TNF or CD95 ligand is overexpressed, it is desirable to inhibit the TNF- or CD95 ligand-induced cytocidal effects, while in other situations, e.g., wound is desirable to inhibit the TNF- or CD95 ligand-induced cytocidal effects, while in other situations, e.g., wound healing applications, it is desirable to enhance the TNF effect, or in the case of CD95, in tumor cells or HIV-infected cells, it is desirable to enhance the CD95 mediated effect.

A number of approaches have been made by the applicants (see, for example, European patent specifications of EP 186,833, EP 308,378, EP 398,327 and EP 412,486) to regulate the deleterious effects of TNF by inhibiting the binding of TNF to its receptors using anti-TNF antibodies or by using soluble TNF receptors (being essentially the soluble extracellular domains of the receptors) to compete with the binding of TNF to the cell surface-bound TNF-receptors (TNF-Rs). Further, on the basis that TNF-binding to its receptors is required for the TNF-induced cellular effects, approaches by applicants (see, for example, EP 568,925) have been made to modulate the TNF effect by modulating the activity of the TNF-Rs.

EP 568,925 relates to a method of modulating signal transduction and/or cleavage in TNF-Rs whereby peptides or other molecules may interact either with the receptor itself or with effector proteins interacting with the receptor, thus modulating the normal function of the TNF-Rs. In EP 568,925, there is described the construction and characterization of various mutant forms of CD120a, having mutations in its extracellular, transmembrane and intracellular domains. In this way, regions within the above domains of CD120a were identified as being essential to the functioning of the receptor, i.e., the binding of the ligand (TNF) and the subsequent signal transduction and intracellular signaling which ultimately results in the observed TNF-effect on the cells. Further, there are also described a number of approaches to isolate and identify proteins, peptides or other factors which are capable of binding to the various regions in the above domains of CD120a, which proteins, peptides and other factors may be involved in regulating or modulating the activity of TNF-Rs. A number of approaches for isolating and cloning the DNA sequences encoding such proteins and peptides; for constructing expression vectors for the production of these proteins and peptides; and for the preparation of antibodies or fragments thereof which interact with CD120a or with the above proteins and peptides that bind various regions of CD120a, are also set forth in EPO 368,925. However, EP 568,925 does not specify the actual proteins and peptides that bind to the intracellular domains of the TNF-Rs. Similarly, in EP 568,925 there is no disclosure of specific proteins or peptides capable of binding the intracellular domain of CD95.

Thus, when it is desired to inhibit the effect of TNF, or of the CD95 ligand, it would be desirable to decrease the amount or the activity of TNF-Rs or CD95 at the cell surface, while an increase in the amount or the activity of TNF-R or CD95 would be desired when an enhanced TNF or CD95 ligand effect is sought. To this end the promoters of both the CD120a and the CD120b have been sequenced, analyzed and a number of key sequence motifs have been found that are specific to various transcription regulating factors, and as such the expression of these TNF-Rs can be controlled at their promoter level, i.e., inhibition of transcription from the promoters for a decrease in the number of receptors, and an enhancement of transcription from the promoters for an increase in the number of receptors (EP 606,869 and WO 95/31206).

While it is known that the tumor necrosis factor (TNF) receptors, and the structurally related receptor CD95, trigger in cells, upon stimulation by leukocyte-produced ligands, destructive activities that lead to their own demise, the mechanisms of this triggering are still little understood. Mutational studies indicate that in CD95 and CD120a signaling for cytotoxicity involve distinct regions within their intracellular domains (Brakebusch et al, 1992; Tartaglia et al, 1993; Itoh and Nagata, 1993). These regions (the 'death domains') have sequence similarity. The 'death domains' of both CD95 and CD120a tend to self-associate. Their self-association apparently promotes the receptor aggregation, which is necessary for initiation of signaling (see Bigda et al, 1994; Boldin et al, 1995), and at high levels of receptor expression can result in triggering of ligand-independent signaling (Boldin et al, 1995).

Some of the cytotoxic effects of lymphocytes are mediated by interaction of a lymphocyte-produced ligand with CD95 in target cells (see also Nagata and Goldstein, 1995). Cell killing by mononuclear phagocytes involves TNF and its receptor CD120a (see also Vandenabeele et al, 1995). Like other receptor-induced effects, cell death induction by the TNF receptors and CD95 occurs via a series of protein-protein interactions, leading from ligand-receptor binding to the eventual activation of enzymatic effector functions, which have been shown to comprise non-enzymatic protein-protein interactions that initiate signaling for cell death: binding of trimeric TNF or the CD95 ligand molecules to the receptors, the resulting interactions of their intracellular domains (Brakebusch et al, 1992; Tartaglia et al, 1993; Itoh and Nagata, 1993) augmented by a propensity of the death-domain motifs to self-associate (Boldin et al, 1995a), and induced binding of two cytoplasmic proteins (which can also bind to each other) to the receptors' intracellular domains— MORT-1 (or FADD) to CD95 (Boldin et al, 1995b; Chinnaiyan et al, 1995; Kischkel et a, 1995) and TRADD to CD120a (Hsu et al, 1996). Besides their binding to CD95 and CD120a, MORT-1 and TRADD are also capable of binding to each other, as well as to other death domain containing proteins, such as RIP (Stanger et al, 1995), which provides for a functional "cross-talk" between CD95 and CD120a. These bindings occur through a conserved sequence motif, the 'death domain module' common to the receptors and their associated proteins. Furthermore, although in the yeast two-hybrid test MORT-1 was shown to bind spontaneously to CD95, in mammalian cells, this binding takes place only after stimulation of the receptor, suggesting that MORT-1 participates in the initiating events of CD95 signaling. MORT-1 does not contain any sequence motif characteristic of enzymatic activity, and therefore, its ability to trigger cell death seems not to involve an intrinsic activity of MORT-1 itself, but rather, activation of some other protein(s) that bind MORT-1 and act further downstream in the signaling cascade. Cellular expression of MORT-1 mutants lacking the N-terminal part of the molecule have been shown to block cytotoxicity induction by CD95 or CD120a (Hsu et al, 1996; Chinnaiyan et al, 1996), indicating that this N-terminal region transmits the signaling for the cytocidal effect of both receptors through protein-protein interactions.

Recent studies have implicated a group of cytoplasmic thiolproteases, which are structurally related to the *Caenorhabditis elegans* protease CED3 and to the mammalian interleukin-1 beta-converting enzyme (ICE) in the onset of various physiological cell death processes (reviewed in Kumar, 1995 and Henkart, 1996). There is also evidence that protease(s) of this family take part in the cell-cytotoxicity induced by CD95 and TNF-Rs. Specific peptide inhibitors of the proteases and two virus-encoded proteins that block their function, the cowpox protein CrmA and the Baculovirus p35 protein, were found to provide protection to cells against this cell-cytotoxicity (Enari et al, 1995; Tewari et al, 1995; Xue et al, 1995; Beidler et al, 1995). Rapid cleavage of certain specific cellular proteins, apparently mediated by protease(s) of the CED3/ICE (caspase) family, could be demonstrated in cells shortly after stimulation of CD95 or TNF-Rs.

One such protease and various isoforms thereof (including inhibitory ones), is known as MACH (now caspase-8) which is a MORT-1 binding protein has been isolated, cloned, characterized, and its possible uses also described, as is set forth in detail and incorporated herein in their entirety by reference, in co-owned PCT/US96/10521, and in a publication of the present inventors (Boldin et al, 1996). Another such protease and various isoforms thereof (including inhibitory ones), designated Mch4 (also called caspase-10) has also been isolated and characterized by the present inventors (unpublished) and others (Fernandes-Alnemri et al, 1996; Srinivasula et al, 1996). Caspase-10 is also a MORT-1 binding protein. Thus, details concerning all aspects, features, characteristics and uses of caspase-10 are set forth in the above noted publications, all of which are incorporated herein in their entirety by reference.

It should also be noted that the caspases, caspase-8 and caspase-10, which have similar pro-domains (see Boldin et al, 1996; Muzio et al, 1996; Fernandes-Alnemri et al, 1996; Vincenz and Dixit, 1997) interact through their pro-domains with MORT-1, this interaction being via the 'death effector domain', DED, present in the N-terminal part of MORT-1 and present in duplicate in caspase-8 and caspase-10 (see Boldin et al, 1995b; Chinnaiyan et al, 1995).

The caspases (cysteine aspartate-specific proteinases) are a growing family of cysteine proteases that share several common features. Most of the caspases have been found to participate in the initiation and execution of programmed cell death or apoptosis, while the others appear to be involved in the production of proinflammatory cytokines (Nicholson and Thornberry et al, 1997, Salvesen et al, 1997, Cohen, 1997). They are synthesized as catalytically almost inactive precursors and are generally activated by cleavage after specific internal aspartate residues present in interdomain linkers. The cleavage sites of caspases are defined by tetrapeptide sequences (X-X-X-D) and cleavage always occurs downstream of the aspartic acid. As a result certain mature active caspases can process and activate their own as well as other inactive precursors (Fernandes-Alnemri et al, 1996, Srinivasula et al, 1996).

Activation of the programmed cell death process is generally specific and involves sequential processing of downstream caspases named "executioner" caspases by upstream caspases named "initiator" caspases. The functional characteristics of the two classes of caspases are also reflected by their structure. In fact the "initiator caspases" contain longer pro-domain regions as compared to the "executioner" caspases (Salvesen et al, 1997; Cohen, 1997). The long pro-domain allows the initiator or "'apical" caspases to be activated by triggering of the death receptors of the TNF receptor family. Upon ligand-induced trimerization of the death receptors, the initiator caspases are recruited through their long N-terminal pro-domain to interact with specific adapter molecules to form the death inducing signaling complex (Cohen, 1997; Kischkel et al, 1995). For example, caspase-8/MACH and probably caspase-10, which contain two DEDs, are recruited to the receptor complex by the adapter molecules FADD/MORT-1, whereas caspase-2 is assumed to be recruited by CRADD/RAIDD and RIP (Nagata et al, 1997; MacFarlane et al, 1997; Ahmad et al, 1997; Duan and Dixit, 1997). Due to the trimeric nature of the activated receptor complex, at least two caspase molecules are thought to be brought in close proximity to each other, thus leading to their activation by auto-catalytic processing (Yang et al, 1998; Muzio et al, 1998).

Caspases are synthesized as pro-enzymes consisting of three major subunits, the N-terminal pro-domain, and two subunits, which are sometimes separated by a linker peptide. The two subunits have been termed "long" or subunit 1 (Sub-1) containing the major part of the active enzymatic site, and "short" or subunit 2 (Sub-2). For full activation of the enzyme, it is processed to form the pro-domain and the two sub-domains. The two subunits form a heterodimer. Based on the deduced three dimensional structure of caspase-3, it appears that the C-terminal end of the long domain as well as the N-terminus of the short sub-domain have to be freed and the C-terminus of the short subunit has to be brought into close proximity with the N-terminus of the long subunit in order to yield a correctly folded and active enzyme (Rotonda et al, 1996; Mittl et al, 1997; Srinivasula et al, 1998).

Although pathways leading to apoptosis or necrosis have always been considered to be completely distinct, recent findings have suggested that the caspases, which represent the main mediators of apoptosis, can also be implicated in necrosis both in a negative and a positive manner. Indeed, overexpression of the caspase inhibitor CrmA in L929 cells was shown to increase by a factor of 1000 the sensitivity of these cells for the necrotic activity of TNF (Vercammen et al, 1998), indicating an inhibitory role of caspases on TNF-induced necrotic activity. Moreover, the TNFR1- and Fas-associated death domains that play a crucial role in apoptosis induction by these ligands (reviewed in Wallach et al, 1999), were recently also suggested to play an important role in necrosis induction (Boone et al, 2000). Interestingly, the FasL-induced liver necrosis was shown to be blocked by caspase inhibitors (Kunstleet al, 1997).

Because caspase-mediated proteolysis is critical and central element of the apoptotic process (Nicholson and Thornberry, 1997; Villa et al, 1997; and Salvesen and et al, 1997), identification of the crucial downstream molecular targets of these proteases is inevitable for understanding apoptotic signal transduction. Various structural and signaling proteins have been shown to be cleaved by caspases during apoptotic death (Nicholson and Thornberry, 1997; Villa. et al., 1997) including ICAD, an inhibitor of caspase-activated Dnase, which is essential for internucleosomal DNA degradation but not for execution of apoptosis (Enari et al, 1998; Sakahira et al, 1998). Gelsolin, an actin-regulatory protein that modulates cytoplasmic actin gelsol transformation (Yin and Stossel, 1979), is implicated in apoptosis on the basis of (i) its cleavage during apoptosis in vivo (Kothakota et al, 1997) (ii) prevention of apoptosis by its overexpression (Ohtsu et al, 1997) and (iii) induction of apoptosis by one of the cleaved products Kothakota et al, 1997). Gelsolin has Ca+2 activated multiple activities, severs actin filaments, and caps the fast growing ends of filaments, and also nucleates actin polymerization (Yin and Stossel, 1980; Kurth and Bryan, 1984; Janmey and Stossel, 1987).

Application WO 00/39160 discloses caspase-8 interacting proteins capable of interacting with Sub-1 and/or Sub-2 of caspase-8. The caspase interacting proteins were discovered by two-hybrid screen using single chain construct of caspase-8.

Application WO 98/30582 (Jacobs et al) discloses nucleotide and the predicted amino acid sequences of secreted or membrane protein DF518_3 isolated from a human adult brain cDNA library. The protein was identified by using methods that are selective for cDNAs encoding secreted proteins (U.S. Pat. No. 5,536,637), and was also identified as encoding a secreted or transmembrane protein on the basis of computer analysis of the amino acid sequence of the encoded protein. The protein according to the present invention differs from DF518_3 in its location (intracellular versus membrane/secreted) and its amino acid sequence (has one non-conservative amino acid change in residue 230 E versus G). In the WO application numerous non-related activities that are not supported by any data, are attributed to DF518_3.

SUMMARY OF THE INVENTION

The present invention relates to an intracellular polypeptide (Cari) capable of interacting with a pro-caspase or mutein or fragment thereof, which polypeptide comprises the amino acid sequence of SEQ ID NO:3, or an isoform, a mutein except DF518_3, an allelic variant, fragment, fusion protein, or derivative thereof. In one embodiment, the polypeptide of the invention is cleavable in vitro and in vivo by caspases, preferably caspase-8.

In addition, the invention provides for a Cari polypeptide mutein having a dominant-negative effect on the activity of the endogenous Cari polypeptide and muteins capable of inhibiting or increasing the cytotoxic effect of a caspase, more preferably, caspase-8.

In one embodiment, the invention provides a non-cleavable Cari mutant (Cari D600E) polypeptide, wherein the amino acid residue in which residue D600 in the Cari polypeptide is replaced with the glutamic acid residue. This polypeptide is capable of increasing the cytotoxic effect of caspase-8. In another embodiment, the invention provides peptides derived from Cari responsible for binding caspase-8 such as the ones comprising the amino acid sequences in SEQ ID NO:4 and SEQ ID NO:5.

Furthermore, the present invention provides a DNA sequence encoding a Cari polypeptide, or an isoform, allelic variant, fragment, mutein (e.g., Cari D600E), fusion protein, or derivative thereof, a DNA sequence capable of hybridizing under moderately stringent conditions to a DNA sequence encoding a Cari polypeptide, or an isoform, allelic variant, fragment, mutein, fusion protein, or derivative thereof, or to a DNA sequence corresponding to SEQ ID NO:2.

More specifically the present invention provides a DNA sequence encoding the polypeptide of SEQ ID NO:3. The invention also provides the DNA of a non-cleavable Cari mutant (e.g., Cari D600E), and the DNA encoding peptides (e.g., SEQ ID NO:4, SEQ ID NO:5). In addition, the present invention provides also a ribozyme and an antisense oligonucleotide comprising at least 9 nucleotides corresponding to the above DNA sequence, preferably the antisense oligonucleotide of SEQ ID NO:6 and SEQ ID NO:7.

The present invention also provides vectors comprising the DNA sequence encoding a Cari polypeptide, or its isoform, allelic variant, fragment, mutein, fusion protein, or derivative thereof, and methods for the production of the Cari polypeptide, or its isoform, allelic variant, fragment, mutein, fusion protein, or derivative thereof by introducing said vector in prokaryotic or eukaryotic host cells, preferably, a mammalian, insect, or yeast cell, and more preferably in cells selected from HeLa, 293 T HEK and CHO cells and growing the cells and isolating the protein produced.

Moreover, the invention provides a viral vector encoding a Cari polypeptide, or its isoform, allelic variant, fragment, mutein, a fusion protein, a ribozyme, an antisense oligonucleotide or derivative thereof and its use for introducing into mammalian cells a Cari polypeptide, isoform, allelic variant, fragment, mutein, fusion protein.

In addition the invention provides a vector suitable for targeting regulatory sequences functional in cells for the activation of the endogenous Cari or an inhibitor of Cari expression.

In another aspect the invention provides for a polyclonal or monoclonal antibody, chimeric antibody, fully humanized antibody, anti-anti-Id antibody or fragment thereof directed at an epitope of a Cari polypeptide, or its isoform, allelic variant, fragment, mutein, fusion protein, or derivative thereof and its use for diagnostic purposes or development in immunoassays for the detection of a Cari polypeptide, or its isoform, allelic variant, fragment, mutein, a fusion protein, or derivative thereof in biological fluids.

Furthermore, the invention provides a host cell selected from prokaryotic or eukaryotic cells, preferably HeLa, 293 T HEK and CHO cells, comprising a vector encoding Cari, and a method of producing Cari or an isoform, mutein, allelic variant, fragment, fusion protein or derivative thereof. Alternatively, the invention provides a method of producing Cari or an isoform, mutein, allelic variant, fragment, fusion protein or derivative thereof comprising the generation of a transgenic animal and isolating the protein produced from the body fluids of the animal.

In one aspect, the invention provides a method of gene therapy for treatment of an inflammatory disease selected from multiple sclerosis with primary oligodendrogliopathy, autoimmune uveoretinitis, diabetes, lupus, autoimmune myocarditis I, HCV mediated chronic hepatitis, chronic gastritis, e.g., type A gastritis, mixed connective tissue disease (MCTD), Crohn's disease, or ulcerative colitis, comprising inducing the expression of Cari or a mutein, (e.g., Cari D600E), fragment (e.g., SEQ ID NO:4, SEQ ID NO:5), antisense preferably of SEQ ID NO-6 and/or SEQ ID NO:7 and a ribozyme of Cari at a desired site in a human patient in need.

In addition, the invention provides a method of treatment and inflammatory disease selected from multiple sclerosis with primary oligodendrogliopathy, autoimmune uveoretinitis, diabetes, lupus, autoimmune myocarditis I, HCV mediated chronic hepatitis, chronic gastritis, e.g., type A gastritis, mixed connective tissue disease (MCTD), Crohn's disease, or ulcerative colitis, comprising regulation of endogenous Cari or Cari inhibitor, by targeting a vector having DNA regulatory sequences functional in cells for enabling endogenous gene activation of Cari or an endogenous Cari inhibitor at a desired site in a human patient in need.

Moreover, the invention provides the use of Cari pqlypeptide, mutein, isoform, allelic variant, fragment (e.g., SEQ ID NO:4, SEQ ID NO:5), fusion protein or derivative thereof, an antisense (e.g., SEQ ID NO:6 and/or SEQ ID NO:7), a vector encoding Cari and its fragments, and antibodies against Cari for down-regulation of a caspase, in situations where excessive cell death by apoptosis occurs, for example, by induction of the TNF receptor signaling pathway.

The invention provides further the use of Cari polypeptide, or a mutein (e.g., Cari D600E), an isoform, allelic variant, or fragment, fusion protein or derivative thereof, a vector encoding Cari and its fragments, a DNA encoding Cari or fragments and muteins, a vector comprising the DNA encoding Cari or fragment or muteins, vectors for endogenous Cari activation and anti-idiotype antibodies of Cari for up-regulation of a caspase activity and increase of apoptosis in situations where excessive cell death is required.

In another aspect, the invention provides a pharmaceutical composition comprising a therapeutically effective amount of Cari polypeptide, or a mutein (e.g., Cari D600E), isoform, allelic variant, fragment (e.g. SEQ ID NO:4, SEQ ID NO:5) fusion protein, or derivative thereof, a DNA or vector encoding Cari or muteins or fragments, a vector for endogenous activation of Cari or its inhibitor, antisense, ribozyme or an antibody specific for Cari, for the treatment of an inflammatory disease selected from multiple sclerosis with primary oligodendrogliopathy, autoimmune uveoretinitis, diabetes, lupus, autoimmune myocarditis I, HCV mediated chronic hepatitis, chronic gastritis, e.g., type A gastritis, mixed connective tissue disease (MCTD), Crohn's disease, or ulcerative colitis.

In addition, the invention provides a pharmaceutical composition comprising a therapeutically effective amount of Cari polypeptide, or a mutein (e.g., Cari D600E), isoform, allelic variant, fragment fusion protein, or derivative thereof, a DNA or vector encoding Cari or muteins or fragments, a vector for endogenous activation of Cari, or an anti idiotype antibody specific for Cari, for the treatment of cancer.

In another embodiment, the invention provides a pharmaceutical composition comprising a therapeutically effective amount of an inhibitor of Cari for the treatment or prevention of a disease in which the activity of Cari is involved.

The invention further provides a method for the isolation, identification and cloning of another polypeptide of the same class of Cari comprising the use of a DNA encoding Cari or muteins or fragments thereof to screen a DNA library, or a caspase specific antibody suitable for co-immunoprecipitation of a caspase and bound polypeptide or by affinity purification of such polypeptides from samples selected from body fluids, cell extracts and DNA expression libraries with Cari specific antibodies, or by using Cari polypeptide or a mutein, isoform, allelic variant, fragment, fusion protein or derivative thereof as the prey or the bait in the yeast two-hybrid procedure.

The invention also relates to a method for isolating a polypeptide or factor involved in intracellular signaling processes, from samples selected from cell extracts human fluids and expression libraries, comprising co-immunoprecipitating Cari and the polypeptides or factors involved in intracellular signaling using an antibody recognizing Cari.

Furthermore, the invention provides a method for screening for a peptide or a small molecule antagonist to Cari, comprising high through put screening and selection of such molecules able to inhibit the interaction of Cari to pro-caspase-8 or a mutein (e.g., Cari D600E), isoform, allelic variant, fragment (e.g., SEQ ID NO:4 or SEQ ID NO:5), fusion protein or derivative thereof or selection of molecules able to inhibit apoptosis enhanced by Cari or a mutein, isoform, allelic variant, fragment, fusion protein or derivative thereof.

In addition, the invention relates to a method of treatment and/or prevention of a disorder selected from, multiple sclerosis with primary oligodendrogliopathy, autoimmune uveoretinitis, diabetes, lupus, autoimmune myocarditis I, HCV mediated chronic hepatitis, chronic gastritis, e.g., type A gastritis, mixed connective tissue disease (MCTD), Crohn's disease, ulcerative colitis and cancer, comprising administering to a patient in need thereof a pharmaceutically effective amount of a Cari polypeptide or a mutein (e.g., Cari D600E), isoform, allelic variant, fragment (e.g., SEQ ID NO:4, SEQ ID NO:5), fusion protein or derivative thereof or a DNA or vectors encoding Cari or mutein or fragments thereof, or vectors for endogenous gene activation of Cari or Cari inhibitor, or a specific antibody for Cari.

BRIEF DESCRIPTION OF THE FIGURES

FIG. 1 shows the amino acid sequence of pro-caspase-8 (SEQ ID NO:8). The peptide sequences from caspase-8 used for the preparation of mAbs are in bold and underlined.

Peptide 179—The peptide CQGDNYQKGIPVETD (residues 360-374 of SEQ ID NO:8) corresponding to the C-terminus of the large subunit of caspase-8 (Sub-1).

Peptide 182—The peptide LSSPQTRYIPDEAD (residues 385-398 of SEQ ID NO:8) corresponding to the N-terminus of the small subunit of the caspase-8 (Sub-2, residues Leu385-Asp398).

Peptide 183—The peptide SESQTLDKVYQMKSKPR (residues 217-233 of SEQ ID NO:8) corresponding to the N-terminus of Sub-1 (residues Ser217-Arg233).

Figure 2:
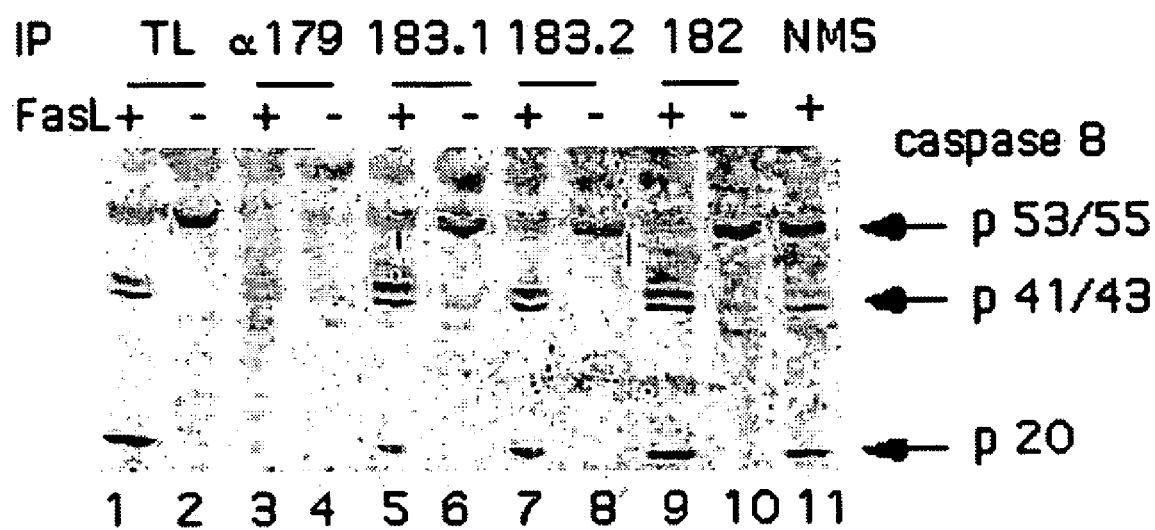

FIG. 2 shows the effective immunoprecipitation of minute amounts of caspase-8 found in lysates of BJAB cells using a monoclonal antibody against epitope 179. Depletion of caspase-8 from the BJAB cell lysates (prepared before, −, and after, +, Fas receptor stimulation) by immunoprecipitation with various antibodies is shown from left to right:

Lanes 3 and 4, mAb179: a monoclonal antibody prepared against a peptide corresponding to the C-terminus of Sub-1 (the large subunit of the caspase-8, residues Cys360-Asp374).

Lanes 5 and 6, mAb 183.1 and lanes 7 and 8, mAb 183.2, two monoclonal antibodies prepared against a peptide corresponding to the N-terminus of Sub-1 (residues Ser217-Gly234).

Lanes 9 and 10, mAb 182 a monoclonal antibody prepared against a peptide corresponding to the N-terminus of Sub-2 (the small subunit of the caspase-8) (residues Lys385-Asp399).

Lane 11, NMS—normal mouse serum.

The figure shows Western blotting assessment of the amounts of caspase-8 left in the cell lysates following immunoprecipitation by the indicated antibodies and in total cell lysates (lanes 1 and 2).

Figure 3A:
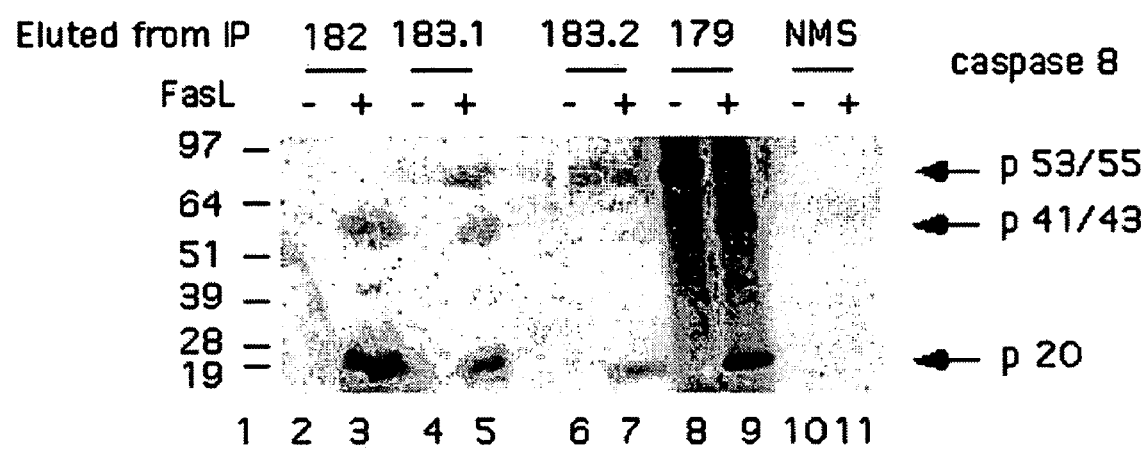

FIG. 3a shows the elution of the caspase-8 immunoprecipitated as in FIG. 2 by competing with the peptides against which the various antibodies have been raised. Caspase-8 in the eluates from the immunoprecipitates produced with the indicated antibodies is detected by Western blot analysis (as in FIG. 2).

Figure 3B:
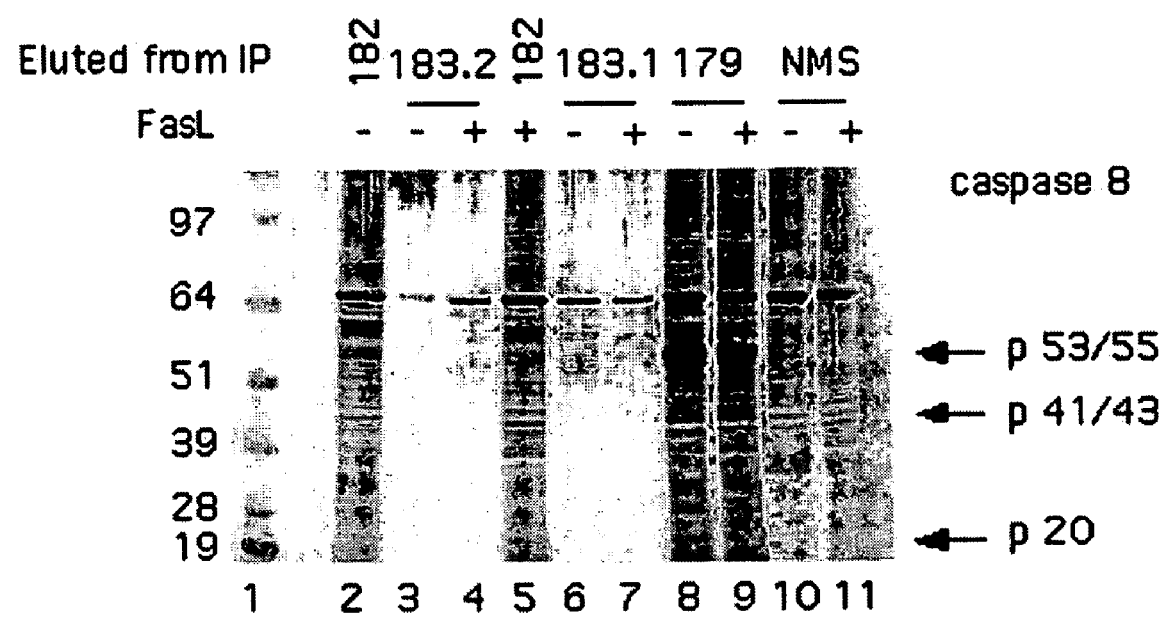

FIG. 3b shows the elution of the caspase-8 immunoprecipitated as in FIG. 2 by competing with the peptides against which the various antibodies have been raised. Caspase-8 in the eluates from the immunoprecipitates produced with the indicated antibodies is shown by Silver staining.

Figure 4:
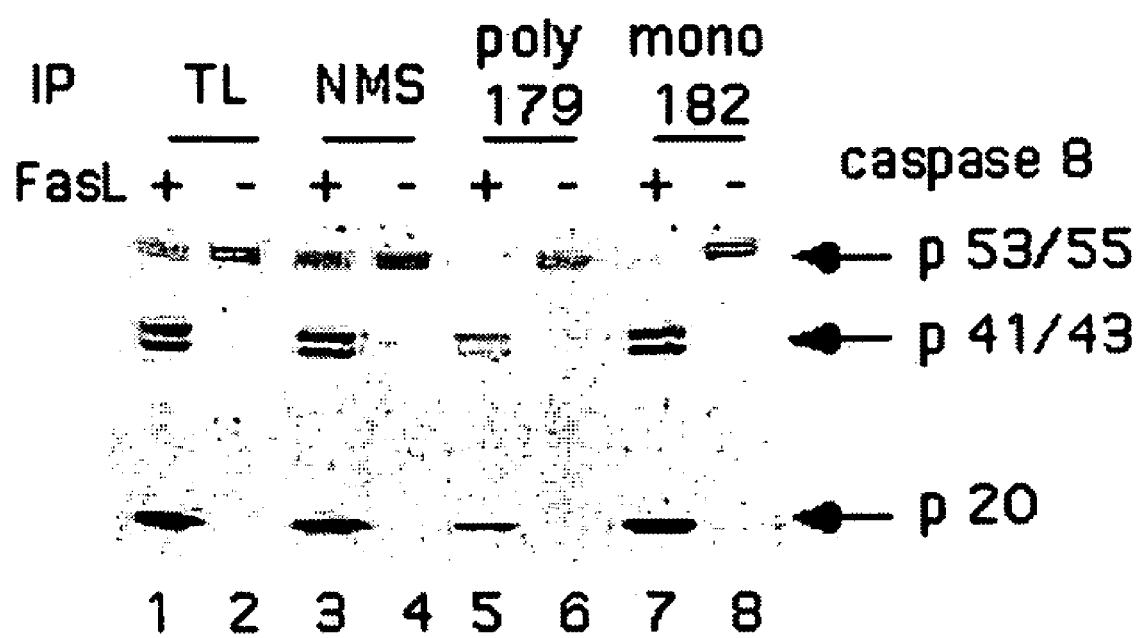

FIG. 4 shows effective immunoprecipitation of minute amounts of caspase-8 found in lysates of BJAB cells using polyclonal serum prepared by immunization with a peptide corresponding to the C-terminus of Sub-1 (the large subunit of the caspase-8, residues Cys360-Asp374). Depletion of caspase-8 from the BJAB cell lysates (prepared before, −, and after, +, Fas receptor stimulation) by immunoprecipitation with various antibodies is shown from left to right. Caspase-8 left in the lysate is detected by Western blot analysis after immunoprecipitation with the following antibodies:

Lanes 3 and 4, NMS—normal mouse serum

Lanes 5 and 6, anti 179 polyclonal antibodies, a rabbit polyclonal antibody prepared against the C-terminus of Sub-1 (the large subunit of the caspase-8, residues Cys360-Asp374).

Lanes 7 and 8 mAb 182.

TL-total cell lysate.

Figure 5:
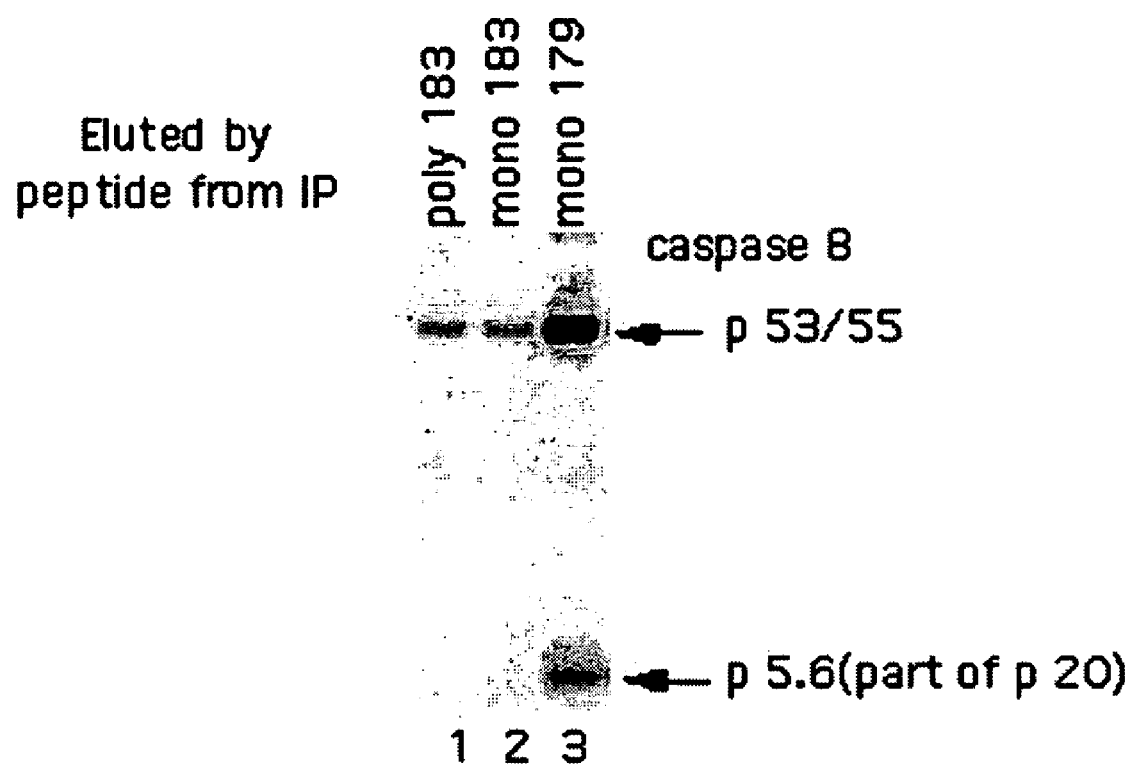

FIG. 5 shows immunoprecipitated and eluted caspase-8 from lysates of non-stimulated BJAB cells using various antibodies. Shown from left to right are the levels of caspase-8 detected by Western blot analysis after elution of immunoprecipitates carried out with the following antibodies:

Lane 1, anti 183 serum against the N-terminus of Sub-1 (residues Ser217-Gly234).

Lane 2, mAb 183.2, a monoclonal antibody against the N-terminus of Sub-1 (residues Ser217-Gly234).

Lane 3, mAb 179, a monoclonal antibody against the C-terminus of Sub-1 (the large subunit of the caspase-8, residues Cys360-Asp374).

The small (5.6 kDa) fragment of caspase-8, produced by the novel-processing mode imposed by mAb 179 is marked with an arrow.

Figure 6:
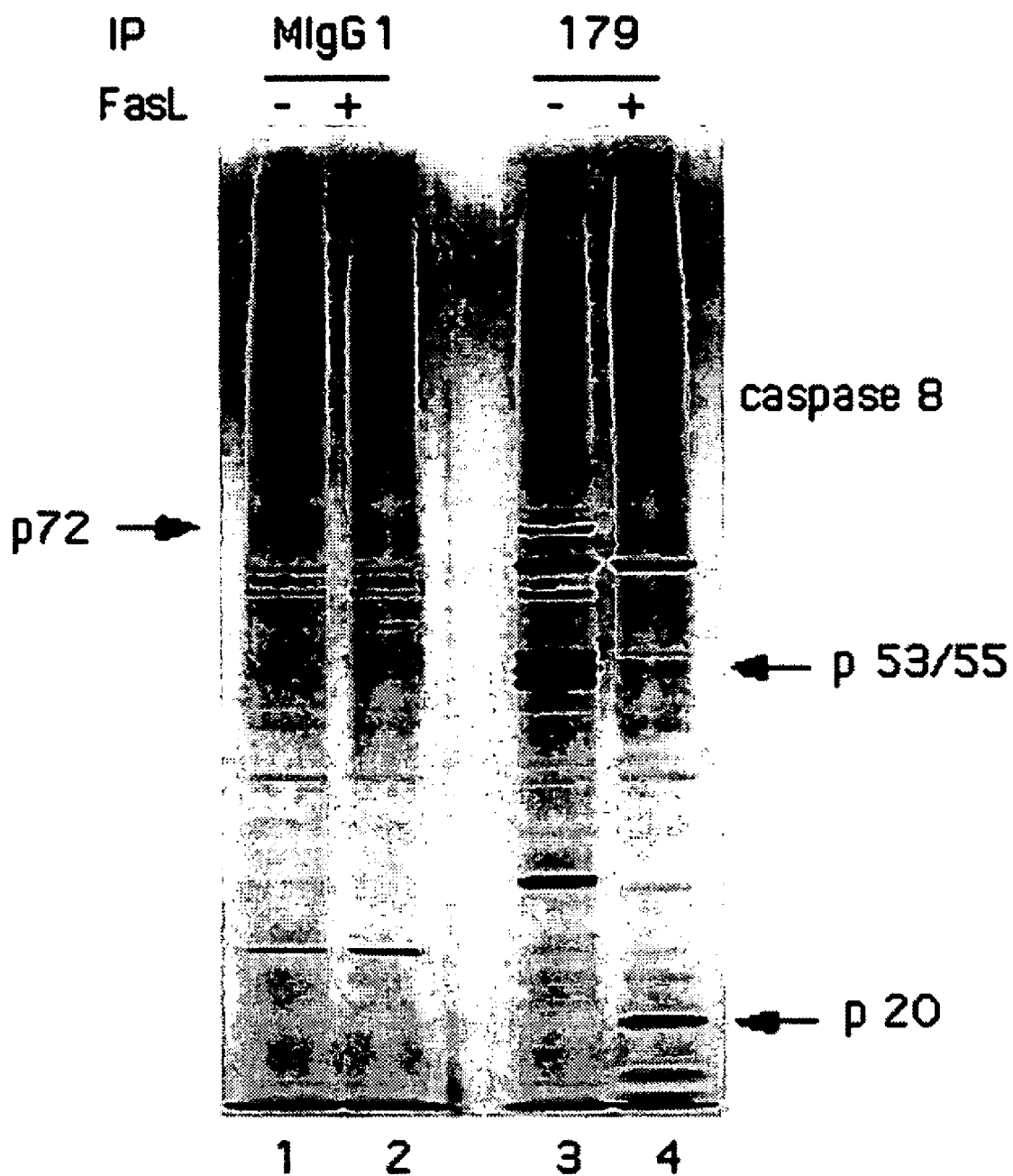

FIG. 6 shows caspase-8 and the caspase-8 bound polypeptide (p72/Cari) that had been immunoprecipitated by mAb 179 from lysates of BJAB cells before or after one-hour stimulation with Fas-ligand and eluted by peptide 179. Immunoprecipitated caspase-8 and bound polypeptides with mAb 179 were eluted (as in FIG. 3b) resolved by SDS-PAGE and Silver stained. Lanes 1 and 2 show controls in which the cell lysates were immunoprecipitated with MIgG1, mouse immunoglobulin IgG1.

Figure 7:
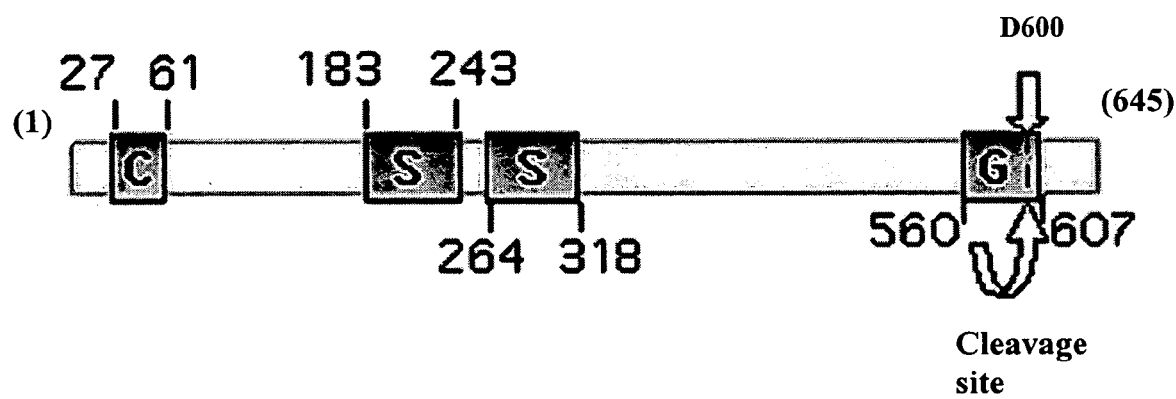

FIG. 7 shows a schematic representation of p72 (CARI) polypeptide motifs. One coiled coil motif (C) and two tandem located 'SURP motifs' (S) are located close to the N terminus of the polypeptide, and one 'G-patch' motif is located at the C terminus of the polypeptide (G motif). The aspartic residue D600 present inside the G motif is also indicated. D600—a mutant in which residue D600 in the polypeptide was replaced with the glutamic acid residue.

Figure 8:
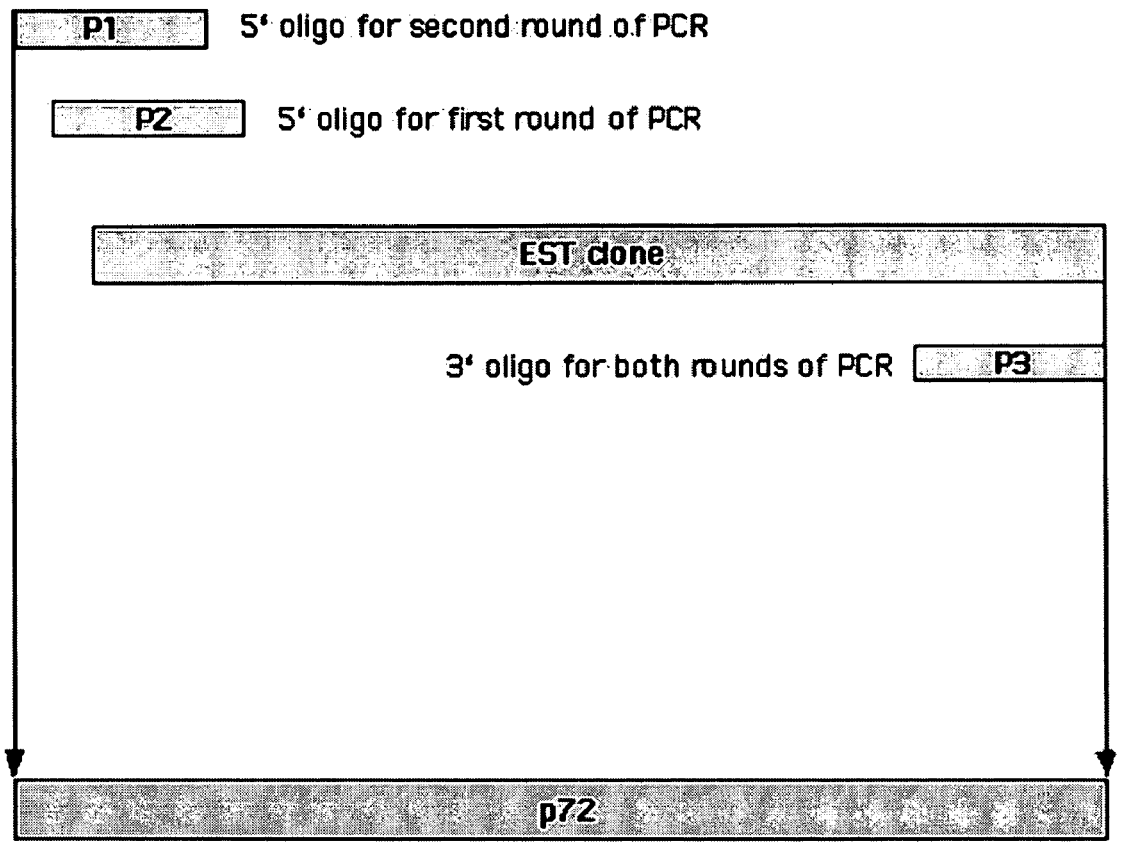

FIG. 8 shows a schematic representation of the approach used for the full-length preparation of p72 (Cari) cDNA. An EST clone IMAGE 2964545 purchased from Incyte Genomics which lacks the sequence of the first 21 nucleotides (which encode the first 7 amino acids) was used as the template for a first polymerase chain reaction (PCR) together with a pair of primers: the forward primer, P2 containing overlapping nucleic acids with the 5' EST clone and additional 15 nucleotides out of the 21 missing nucleotides and the reverse primer, P3 containing overlapping sequences with the 3' EST. The resulting PCR product was used as a template for a second PCR together with a pair of primers: the forward primer, P1 containing the whole 21 missing nucleotides and 5 nucleic acids of the EST and the reverse primer, P3 containing overlapping sequences with the 3' EST.

Figure 9:
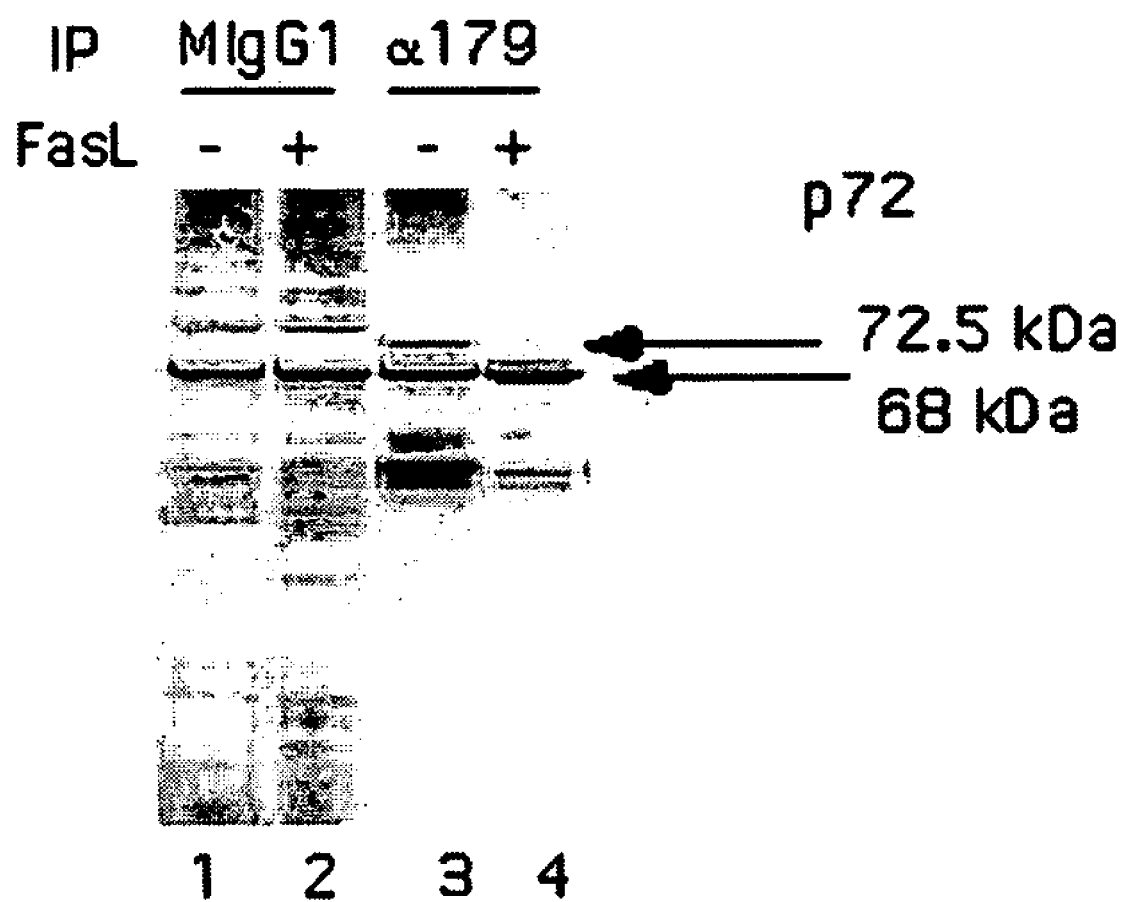

FIG. 9 shows co-immunoprecipitation of caspase-8 and p72 (Cari) by Mab179 from the lysates of BJAB cells at time zero and after 20 minutes stimulation with Fas-ligand. The polypeptides eluted after immunoprecipitating with mAb 179 are resolved in SDS-PAGE gels and detected by Silver staining. A band with an apparent molecular weight of about 72.5 kDa corresponding to p72 (Cari) is co-precipitated with pro-caspase-8 before Fas-ligand stimulation (lane 3). After 20 minutes of stimulation, the level of the 72.5 kDa band decreases and a new band corresponding to a polypeptide of lower apparent molecular weight of about 68 kDa is detected (lane 4).

Lane 1 and 2 show the negative controls comprising immunoprecipitation of cell lysates with MIgG1, mouse immunoglobulin IgG1.

Figure 10:
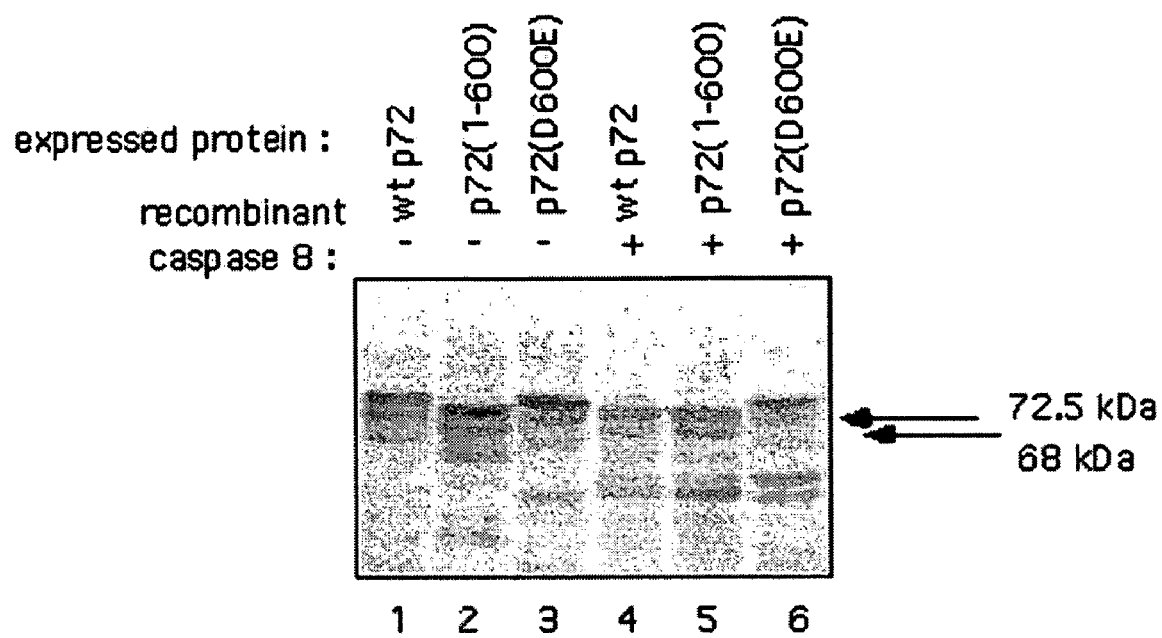

FIG. 10 shows the cleavage of Cari by active caspase-8. A polypeptide encoded by p72 (Cari) cDNA was expressed in vitro in reticulocyte lysates in the presence of $^{35}S$ methionine using the TnT T7 coupled reticulocyte lysate system, and tested after incubation of 1 hour at 37° C. in the presence or absence of recombinant active caspase-8. In addition the cleavage of Cari was studied with TnT products encoded by 2 different p72 cDNA mutants: one encoding Cari in which the residue D600, suspected to be the target residue for caspase-8, was mutated to E (p72 (D600E)) and another in which the gene is deleted and the resulting truncated polypeptide lacks the residues down-stream (D600 p72 (1-600)). The resulting polypeptides were separated on SDS-PAGE and the results were visualized by phosphoimaging.

Figure 11:
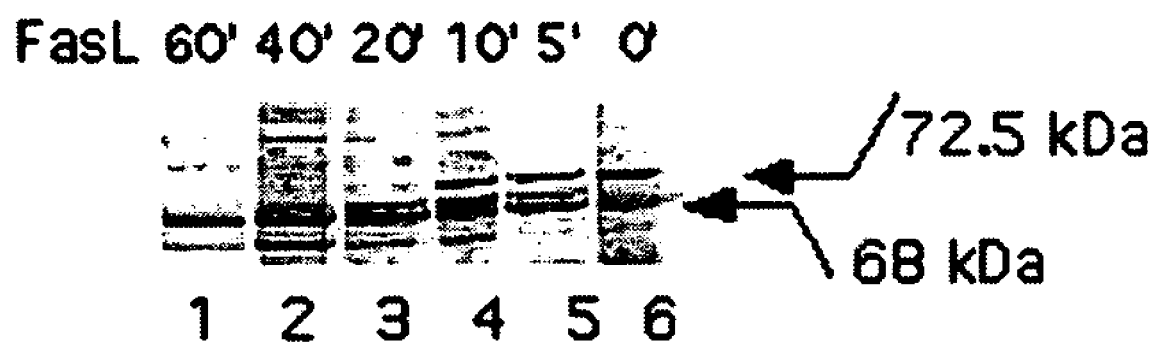

FIG. 11 shows caspase-8 and p72 (Cari) that were co-immunoprecipitated by mAb 179 from the lysates of BJAB cells before (0') or after 5, 10, 20, 40 and 60 minutes of stimulation with Fas-ligand. The peptides were eluted resolved in SDS-PAGE gels and detected by Silver staining. A peptide of apparent molecular weight of 72.5 kDa is detected before stimulation (0'). After 5 and 10 minutes of stimulation a new polypeptide with a lower apparent molecular weight of about 68 kDa appears. After 40 minutes of stimulation the 72.5 kDa band completely disappears and only the 68 kDa is detected. At 60 minutes none of the above polypeptides mentioned were co-precipitated with caspase-8.

Figure 12A:
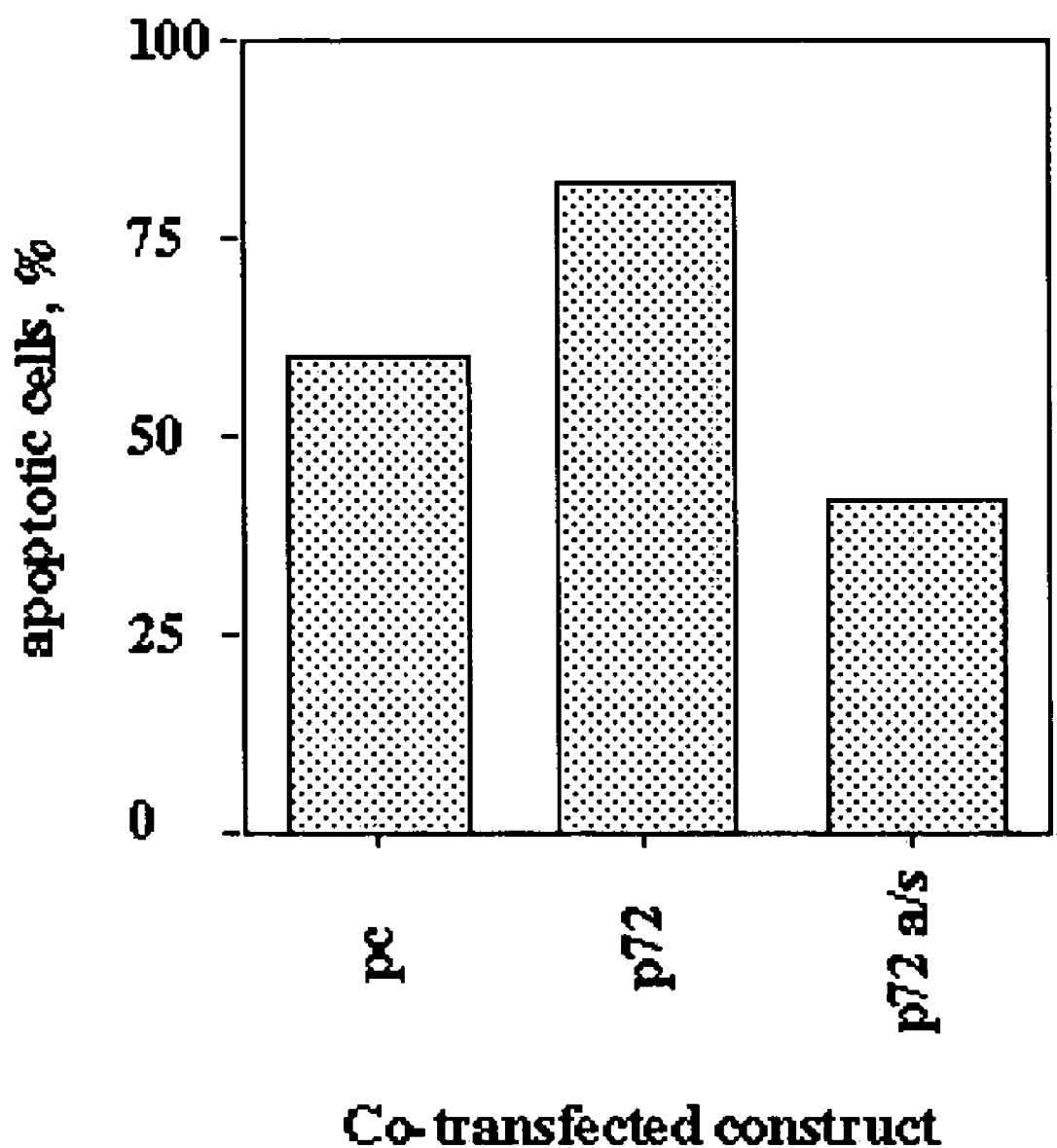

FIG. 12a shows the effect of p72 (Cari) on apoptotic cell death induced by the TNF receptor-signaling pathway. p72 (Cari) cDNA (p72) or antisense p72 (a/s) was inserted into the pcDNA 3.1 expression vector and co-transfected with the p55 TNF receptor inserted in the pcDNA 3.1 vector and with the green fluorescence protein (GFP) expressed from the pEGFPC1 vector, into HEK 293 cells constitutively expressing the T antigen (as a negative control the vector without p72 cDNA insert was used (pc)). After 24 hours, the transfected cells were examined under a fluorescent microscope and cell death was scored by determining the number of cells displaying apoptotic morphology out of the total population of fluorescent cells.

Figure 12B:
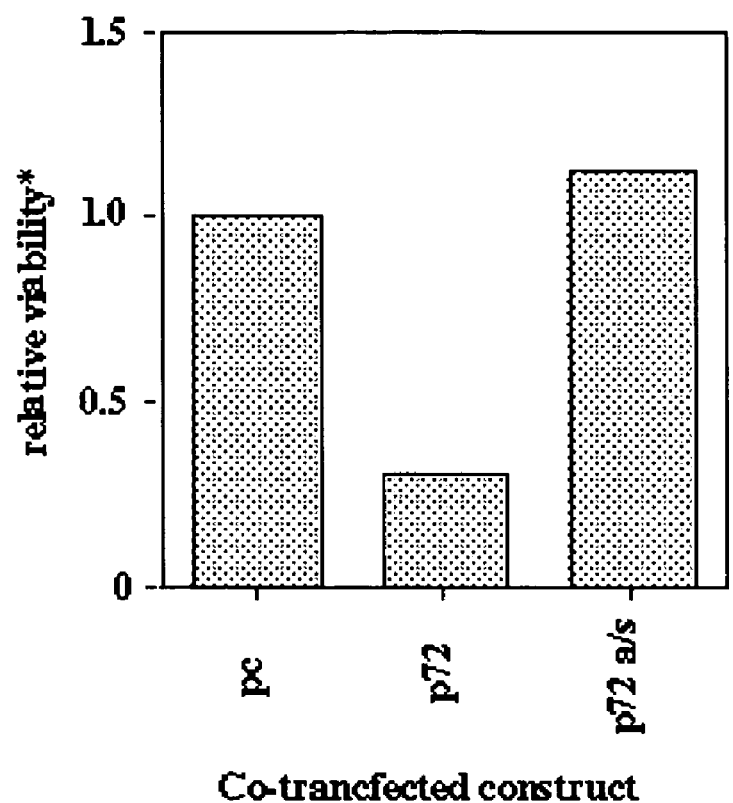

FIG. 12b shows induction of cell death by overexpression of p72 (Cari) in combination with Fas-ligand stimulation. The effect of Cari overexpression on Fas ligand mediated cell death was monitored in HEK 293 cells constitutively expressing the T antigen. In the experiment the cells were co-transfected with a vector pcDNA3.1 (control group) or with pcDNA3.1 encoding Cari or its antisense (pc, p72 or p72 a/s, respectively) and a vector pSBC-2 encoding secreted alkaline phosphatase (SEAP). After 24 hours the transfected cells were induced with Fas-ligand for 16 hours and the growth medium replaced with fresh growth medium. Cell death was measured by determining the amount of SEAP secreted into the growth medium in a period of the next 24 hours.

FIG. 13 shows the alignment between the sequence of the polypeptide obtained in the THC report (THC510568 SEQ ID NO:1) containing the consensus of all the ESTs and the polypeptide predicted by the generated full-length cDNA (SEQ ID NO:3).

Figure 14:
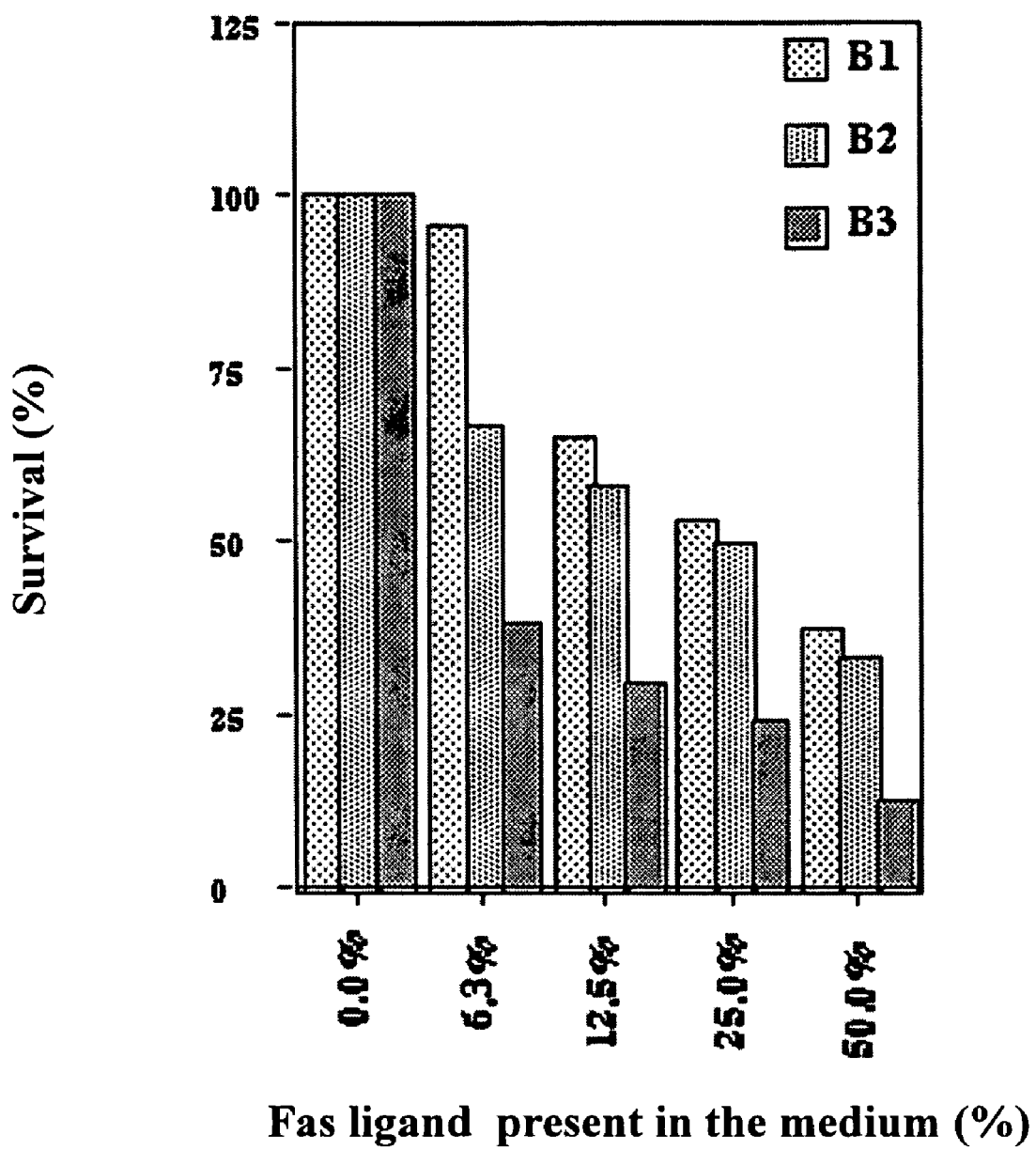

FIG. 14 shows kinetics of cell-death regulation by the Cari non-cleavable mutant D600E p72. Survival of BJAB cells was monitored after Fas ligand application in control cells (B1), cells constitutively expressing transfected p72 (B2) and cells constitutively expressing transfected D600E p72(B3).

FIG. 15 shows the minimal amino acid sequence (SEQ ID NO:5) of the polypeptide in Cari responsible for binding caspase-8. Identification of the minimal polypeptide in Cari that is responsible for binding to pro-caspase-8 was obtained by a detailed deletion study and co-precipitation with pro-caspase-8.

Figure 16:
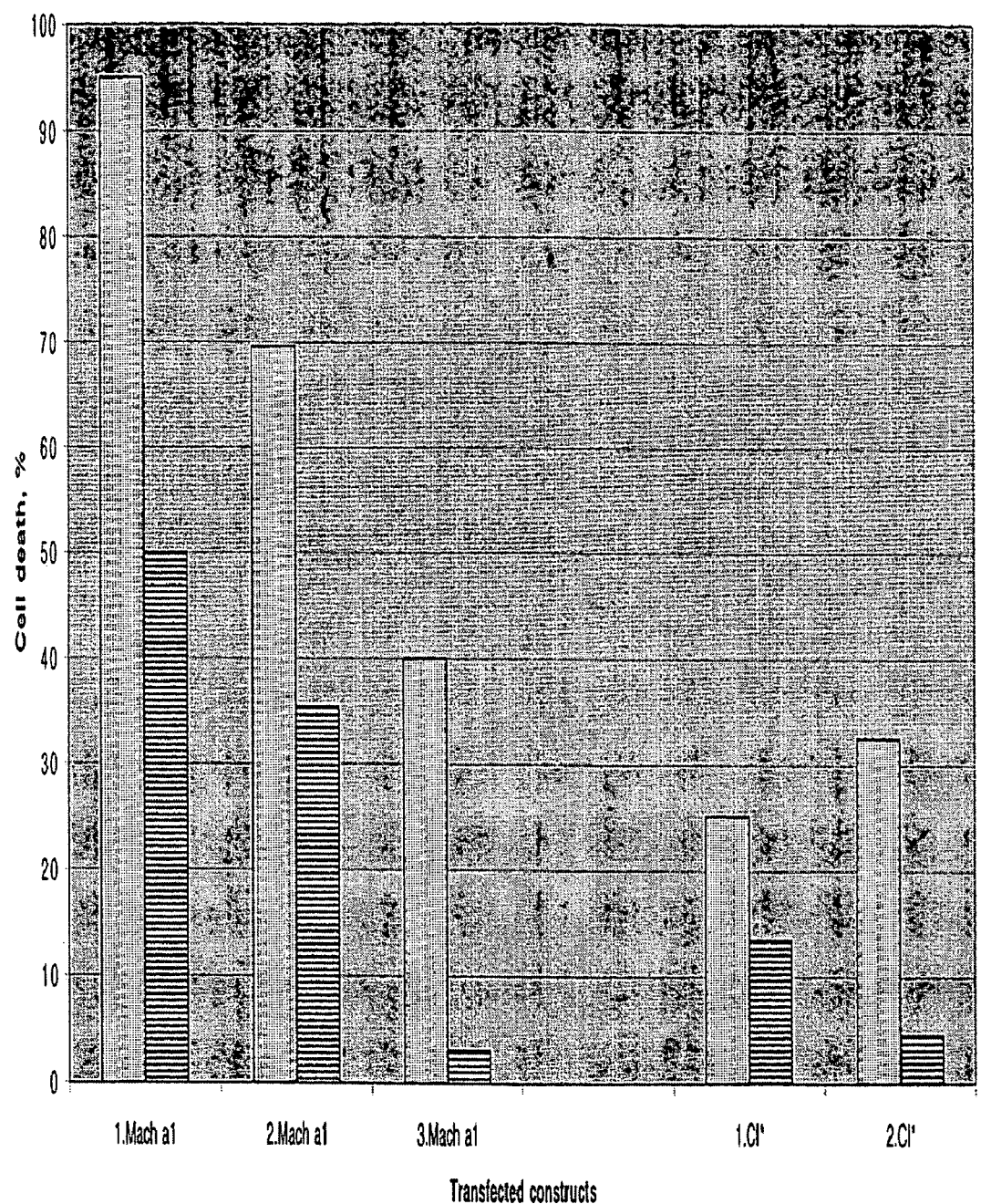

FIG. 16 shows inhibition of apoptosis by expression of a Cari antisense molecule, pSuper-Cari. Apoptosis of cells was induced by overexpression of caspase-8 (Mach a1) or a chimera of extracellular part of p55 TNF R1 fussed to transmembrane and intracellular part of Fas receptor (Cl*) by several independent transfections carried out with vectors encoding these polypeptides and inhibition by Cari antisense was assessed by cotransfection with pSuper-Cari (bars filled horizontally) or with pSuper-vector (Control, bars filled vertically).

DETAILED DESCRIPTION OF THE INVENTION

The present invention relates to an intracellular caspase binding polypeptide p72 (or Cari) or an isoform, a mutein, an allelic variant or a fragment thereof.

On one hand, Cari binds to pro-caspase-8 and enhances the conversion of pro-caspase-8 into active caspase-8 and, on the other hand, active caspase-8 cleaves Cari, and thus the activity of Cari is down-regulated by the active caspase-8.

Cari may bind in addition to pro-caspase-8, to a different caspase, or a mutein or fragment thereof and affect the activity of such caspase as well.

In addition, the invention relates to a fragment of Cari or to a mutein having a dominant-negative effect on the activity of the endogenous Cari polypeptide and to a Cari polypeptide or a mutein or fragment capable of increasing the cytotoxic effect of a caspase, preferably, caspase-8.

For example, a non-cleavable Cari mutant (Cari D600E) polypeptide, wherein the aspartic acid 600 was replaced with a glutamic acid, was generated. This polypeptide induces higher cytotoxicity than the wild type version. Also, small peptides derived from Cari (24 and 16 amino acid residues SEQ ID NO:4 and SEQ ID NO:5, respectively) containing the domain in Cari that was shown to be responsible for binding caspase-8, were generated. Such peptides may inhibit binding of Cari to pro-caspase-8 and therefore inhibit the cytotoxic effect of caspase-8.

For the identification of caspase bound polypeptides (e.g., Cari), cells can be lysed before or after ligand stimulation (e.g., Fas ligand) and subjected to immunoprecipitation by a suitable caspase specific antibody.

A suitable monoclonal antibody for the immunoprecipitation was generated against a peptide from the C-terminal domain of caspase-8 Sub-1. This antibody was capable to immunoprecipitate pro-caspase-8 together with the caspase-8-bound protein (e.g., Cari) and both the caspase-8 and caspase-bound protein could be efficiently eluted from the immune complex and recovered in the supernatant by competing with a peptide derived from the caspase that was originally used to generate the antibodies.

Thus caspase bound polypeptides may be co-immunoprecipitated according to the invention, with such caspase specific suitable antibodies from samples selected from cell lysates of resting or stimulated cells, from expression cDNA libraries and from genomic or combinatorial peptide libraries.

Stimulation of the cells can be effected by lymphokines, for example, Fas-ligand, TNF by environmental factors such as starvation, heat shock etc.

Antibodies may be developed against caspase bound proteins (e.g., Cari) found according to the invention. The antibodies specific to Cari, including the fragments thereof, may be used also to quantitatively or qualitatively detect Cari in a sample or to detect presence of cells, which express Cari. This can be accomplished by immunofluorescence techniques employing a fluorescent labeled antibody (see below) coupled with light microscopic, flow cytometric, or fluorometric detection.

The generation of polyclonal antibodies against polypeptides is described Chapter 2 of Ausubel (1978-1995, 1999 and 2003). The generation of antibodies against peptides may necessitate some changes in protocol, because of the generally lower antigenicity of peptides when compared to polypeptides. The generation of polyclonal antibodies against peptides is described in Ausubel (1978-1995, 1999 and 2003), Chapter 9.

The antibodies prepared against Cari can be used for altering the activity of the protein inside the cells, e.g., by selectively targeting Cari on cells comprising transducing the cells with an intracellularly expressed antibody, or intrabody, against the Cari. The preparation of intrabodies is disclosed in WO 99/14353.

Monoclonal antibodies may be prepared from B cells taken from the spleen or lymph nodes of immunized animals, in particular rats or mice, by fusion with immortalized B cells under conditions, which favors the growth of hybrid cells. For fusion of murine B cells, the cell line Ag-8 is preferred.

The technique of generating monoclonal antibodies is described in many articles and textbooks, such as Ausubel (1978-1995, 1999 and 2003), Chapter 2. Chapter 9 therein describes the immunization, with peptides, or animals. Spleen or lymph node cells of these animals may be used in the same way as spleen or lymph node cells of polypeptide-immunized animals, for the generation of monoclonal antibodies as described in chapter 2 therein.

The techniques used in generating monoclonal antibodies are further described in Kohler and Milstein (1975), and in U.S. Pat. No. 4,376,110.

The preparation of antibodies from a gene bank of human antibodies the hyper variable regions thereof are replaced by almost random sequences is described in U.S. Pat. No. 5,840,479. Such antibodies are preferred if it is difficult to immunize an animal with a given peptide or polypeptide. Some structures are poorly immunogenic and may remain so despite of the addition of adjuvants and of linking to other polypeptides in fusion constructs. The antibodies described in U.S. Pat. No. 5,840,479 are further preferred if it is desired to use antibodies with a structure similar to human antibodies, for instance, when antibodies are desired that have a low immunogenicity in humans.

Once a suitable antibody has been identified, it may be desired to change the properties thereof. For instance, a chimeric antibody may achieve higher yields in production. Chimeric antibodies wherein the constant regions are replaced with constant regions of human antibodies are further desired when it is desired that the antibody be of low immunogenicity in humans. The generation of chimeric antibodies is described in a number of publications, such as Cabilly et al (1984), Morrison et al (1984), Boulianne et al (1984), EP 125023, EP 171496, EP 173494, EP 184187, WO 86/01533, WO 87/02671, and Harlow and Lane (1988).

"Fully humanized antibodies" are molecules containing both the variable and constant region of the human immunoglobulin. Fully humanized antibodies can be potentially used for therapeutic use, where repeated treatments are required for chronic and relapsing diseases such as autoimmune diseases. One method for the preparation of fully human antibodies consist of "humanization" of the mouse humoral immune system, i.e., production of mouse strains able to produce human Ig (Xenomice), by the introduction of human immunoglobulin (Ig) loci into mice in which the endogenous Ig genes have been inactivated. The Ig loci are exceedingly complex in terms of both their physical structure and the gene rearrangement and expression processes required to ultimately produce a broad immune response. Antibody diversity is primarily generated by combinatorial rearrangement between different V, D, and J genes present in the Ig loci. These loci also contain the interspersed regulatory elements, which control antibody expression, allelic exclusion, class switching and affinity maturation. Introduction of unrearranged human Ig transgenes into mice has demonstrated that the mouse recombination machinery is compatible with human genes. Furthermore, hybridomas secreting antigen specific hu-mAbs of various isotypes can be obtained by Xenomice immunization with antigen.

Fully humanized antibodies and methods for their production are known in the art (Mendez et al, 1997; Bruggemann et al, 1991; Tomizuka et al, 2000; Patent WO 98/24893.

Another type of antibody is an anti-idiotypic antibody. An anti-idiotypic (anti-Id) antibody is an antibody, which recognizes unique determinants generally associated with the antigen-binding site of an antibody. An Id antibody can be prepared by immunizing an animal of the same species and genetic type (e.g., mouse strain) as the source of the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb, which induced the anti-Id. Thus, by using antibodies to the idiotypic determinants of a mAb, it is possible to identify other clones expressing antibodies of identical specificity.

The term "antibody" is also meant to include both intact molecules as well as fragments thereof, such as, for example, Fab and F (ab') 2, which are capable of binding antigen. Fab and F (ab') 2 fragments lack the Fc fragment of intact antibody, clear more rapidly from the circulation, and may have less non-specific tissue binding than an intact antibody (Wahl et al, 1983).

It will be appreciated that Fab and F (ab') 2 and other fragments of the antibodies useful in the present invention may be used for the detection and quantitation of Cari according to the methods disclosed herein for intact antibody molecules. Such fragments are typically produced by proteolytic cleavage, using enzymes such as papain (to produce Fab fragments) or pepsin (to produce F (ab') 2 fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody, which can also be recognized by that antibody. Epitopes or "antigenic determinants" usually consist of chemically active surface groupings of molecules such as amino acids or sugar side chains and have specific three-dimensional structural characteristics as well as specific charge characteristics.

The antibodies (or fragments thereof) useful in the present invention may be employed histologically, as in immunofluorescence or immunoelectron microscopy, for in situ detection of Cari. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of Cari polypeptide, but also its distribution on the examined tissue. Using the present invention, those of ordinary skill will readily perceive that any of wide variety of histological methods (such as staining procedures) can be modified in order to achieve such in situ detection.

Such assays for the Cari polypeptide of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying the Cari polypeptide, and detecting the antibody by any of a number of techniques well known in the art.

"Biological fluid" or biological sample denotes any fluid derived from or containing cells, cell components or cell products. Biological fluids include, but are not limited to, cell culture supernatants, cell lysates, cleared cell lysates, cell extracts, tissue extracts, blood, plasma, serum, milk and fractions thereof.

The biological sample may be treated with a solid phase support or carrier such as nitrocellulose, or other solid support or carrier, which is capable of immobilizing cells, cell particles or soluble polypeptides. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well-known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and used in an enzyme immunoassay (EIA). This enzyme, in turn, when later exposed to an appropriate substrate, will react with the substrate in such a manner as to produce a chemical moiety, which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholine-esterase. The detection can be accomplished by calorimetric methods, which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect R-PTPase through the use of a radioimmunoassay (RIA). A good description of RIA may be found in Laboratory Techniques and Biochemistry in Molecular Biology, by Work et al, North Holland Publishing Company, NY (1978) with particular reference to the chapter entitled "An Introduction to Radioimmune Assay and Related Techniques" by Chard T., incorporated by reference herein. The radioactive isotope can be detected by such means as the use of a g counter or a scintillation counter or by autoradiography.

It is also possible to label an antibody in accordance with the present invention with a fluorescent compound. When the fluorescent-labeled antibody is exposed to light of the proper wavelength, its presence can be then detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$E, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including un-reacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the un-reacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and un-complexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of un-reacted labeled antibody. The determination of labeled antibody associated with a solid support or carrier is then determined as in the "simultaneous" and "forward" assays.

The creation of immunoassays, such as RIA or ELISA, has been described in many articles, textbooks, and other publications. Reference is made to WO 97/03998, p. 48, line 4 to p. 52, line 27. Immunoassays of the invention may be if two general types: Firstly, immunoassays using immobilized Cari polypeptide, or an equivalent peptide, may be used in the quantification of Cari. Secondly, immunoassays using immobilized antibodies directed against an epitope of a Cari polypeptide may be used to quantify Cari polypeptides.

Such assays may find use in diagnostics, as the level of Cari and of other polypeptides involved in apoptotic pathways may need to be evaluated in a number of disorders or syndromes where involvement of such pathways is a possibility.

The terms protein and polypeptide are interchangeable in the present specification.

The polypeptide of the invention, a 72 kDa polypeptide, was found to specifically bind pro-Caspase-8. The polypeptide was then further analyzed by partial sequencing and mass-spec analysis. The so-obtained sequence was then entered into a database search program and overlapping sequences and ESTs were identified by computer search. The programs used are well known to all of skill in the art and comprise, e.g., the GCG (genetics computer group) package. Preferably, a search utility such as Basic Local Alignment Search Tool (BLAST) available from the EMBL server (e.g., http://dove.embl-heidelberg.de/Blast2/) is used. The Blastn command may be used for searching for nucleotide sequences that are overlapping or similar with the clone identified.

Alternatively, or in addition to the above-noted methods of searching databases, a library, such as a genomic library or a cDNA library, may be screened in order to identify complete clones. Such screening methods are described in the above-noted Sambrook et al (1989) and Ausubel et al (1978-1995, 1999 and 2003). Alternatively, or in addition, PCR-based cloning techniques may be used, such as rapid amplification of cDNA ends (5' and 3' RACE, Graham et al, 1991, and references therein).

In the present embodiment the EST sequence found was searched in a TIGR Human gene index and the THC report was obtained. Consensus of all the ESTs, that fit these sequences, THC510568, was obtained (SEQ ID NO:1). The consensus sequence lacked the nucleotides that encode the first methionine and the subsequent 6 amino acids of Cari as judging from the mouse EST that exhibits high similarity to the human EST (about 90% identity). The first methionine and the subsequent 6 amino acids of a mouse counterpart protein, which were not missing in the mouse ESTs, were compared to the working draft sequence of the human genome in order to complete the missing human sequence. A hit was obtained corresponding to the sequence of *Homo sapiens* chromosome 19, clone LLNLR-232E12. This clone confirmed the missing 7 amino acids of p72. The full-length cDNA of the p72 protein was obtained by PCR schematically represented in FIG. 8. The whole DNA encoding p72 was recovered, sequenced (SEQ ID NO:2) and the amino acid sequence deduced (SEQ ID NO:3).

P72 polypeptide was found to contain three conserved motifs (FIG. 7): the C motif a coiled motif, two tandem located 'SURP' (also called 'SWAP' motifs, denoted as S FIG. 7) (Denhez and Lafyatis, 1994) close to the N terminus of the polypeptide, and one C terminally located 'G-patch' (FIG. 7 denoted as G) (Aravind and Koonin, 1999). Both the SURP and the G-patch motifs are believed to contribute to RNA-binding, suggesting that the target of p72 may be a RNA molecule. Thus p72 was renamed Cari (the name stands for Caspase-8 Associated polypeptide with RNA binding motifs). Thus, the terms Cari and p72 in the present specification are interchangeable.

The band corresponding to the full Cari polypeptide disappears after stimulation of the cells and instead, a new polypeptide of lower molecular weight appears. The possibility that Cari might be cleaved by activated caspase-8 was inspected by an in vitro assay comprising incubating recombinant produced caspase-8 and Cari labeled polypeptide. Cari may be produced by introducing the coding sequence thereof into an expression vector containing a strong promoter and transfection into a mammalian cell. Alternatively, Cari may be produced in vitro using an in vitro translation system. The technique of in vitro translation is well known to the person of skill in the art, and reagents and detailed protocols therefore are available, e.g., from Stratagene, La Jolla, USA.

In the present embodiment, Cari was labeled, using a radioisotope. Advantageously, when using isotopic labeling, the polypeptide to be tested is expressed in vitro and the isotopically labeled amino acid, preferably, the isotope is $S^{35}$, together with unlabeled amino acid, is added during the in vitro translation reaction. Further preferably, the labeled amino acid is $S^{35}$-Methionine and the ration between libeled and unlabeled amino acid is 1:1 to about 1:1000.

The radioisotope labeled Cari polypeptide and the recombinant produced caspase-8 active enzyme were then combined in a suitable buffer and for a time period sufficient to allow cleavage to occur. The preferred buffer and other preferred parameters of the assay are described in the publication Boldin et al (1996). The preferred time period is generally between 10 min and several hours, preferably between 30 min and one hour.

After allowing cleavage to occur, the reaction was resolved by SDS polyacrylamide gel electrophoresis. The gel was dried and the isotope was detected by photographic film or by phosphoimaging. The polypeptide to be tested can be tagged, and may be detected also by using tag-specific antibodies in a Western blot.

The appearance of additional low molecular weight bands in reactions, in which caspase-8 is added, by comparison with control reactions without caspase-8, indicates cleavage of Cari by caspase-8. The calculated size of the lower molecular weight band detected after the cleavage hints to the approximate location of the cleavage site.

Mutation analysis studies were carried out to find the accurate residue target in Cari. Residue D-600 was found to be the target for cleavage since a mutant Cari having a mutation in residue 600 from D to E is not cleaved by caspase-8 (p72/Cari D600E mutant).

The present invention relates also to the DNA sequence encoding Cari. Moreover, the present invention further concerns the DNA sequences encoding a biologically active isoform, mutein, allelic variant, fragment or fusion protein of Cari. The preparation of such muteins and fragments and derivatives is by standard procedure (see for example, Sambrook et al, 1989) in which in the DNA sequences encoding Cari, one or more codons may be deleted, added or substituted by another, to yield muteins having at least one amino acid residue change with respect to the native polypeptide, except a mutein exhibiting Glycine at amino acid residue 230 in place of Glutamic acid as in the polypeptide DF518-3 in WO 98/30582.

The DNA sequences of the invention encode Cari, isoform, allelic variant, fragment, muteins, or derivative, DNA sequences capable of hybridizing with a cDNA sequence derived from the coding region of a native Cari polypeptide, in which such hybridization is performed under moderately stringent conditions, and which hybridizable DNA sequences encode a biologically active Cari. These hybridizable DNA sequences therefore comprise DNA sequences which have a relatively high similarity to the native Cari cDNA sequence and as such represent Cari-like sequences which may be, for example, naturally-derived sequences encoding the various Cari isoforms, or naturally-occurring sequences encoding polypeptides belonging to a group of Cari-like sequences encoding a polypeptide having the activity of Cari. Further, these sequences may also, for example, include non-naturally occurring, synthetically produced sequences, which are similar to the native Cari cDNA sequence but incorporate a number of desired modifications. Such synthetic sequences therefore include all of the possible sequences encoding muteins, fragments and derivatives of Cari, all of which have the activity of Cari.

As used herein, stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al (1984) for determining the stability of hybrids of 100% identity expressed as melting temperature $T_m$ of the DNA-DNA hybrid:

$$T_m=81.5°\ C.+16.6(\text{Log}M)+0.41\ (\%\ GC)-0.61\ (\%\ \text{form})-500/L$$

where M is the molarity of monovalent cations, % GC is the percentage of G and C nucleotides in the DNA, % form is the percentage of formamide in the hybridization solution, and L is the length of the hybrid in base pairs. For each 1° C. that the $T_m$ is reduced from that calculated for a 100% identity hybrid, the amount of mismatch permitted is increased by about 1%. Thus, if the $T_m$ used for any given hybridization experiment at the specified salt and formamide concentrations is 10° C. below the $T_m$ calculated for a 100% hybrid according to the equation of Meinkoth, hybridization will occur even if there is up to about 10% mismatch.

"Moderately stringent conditions" are those which provide a $T_m$ which is not more than 20° C. below the $T_m$ that would exist for a perfect duplex with the target sequence, either as calculated by the above formula or as actually measured. Without limitation, moderately stringent (15-20° C. below the calculated or measured $T_m$ of the hybrid) conditions use a wash solution of 2×SSC (standard saline citrate) and 0.5% SDS (sodium dodecyl sulfate) at the appropriate temperature below the calculated $T_m$ of the hybrid. The ultimate stringency of the conditions is primarily due to the washing conditions, particularly if the hybridization conditions used are those, which allow less stable hybrids to form along with stable hybrids. The wash conditions at higher stringency then remove the less stable hybrids. A common hybridization condition that can be used with moderately stringent wash conditions described above is hybridization in a solution of 6×SSC (or 6×SSPE) (standard saline-phosphate-EDTA), 5× Denhardt's reagent, 0.5% SDS, 100 μg/ml denatures, fragmented salmon sperm DNA at a temperature approximately 200 to 25° C. below the $T_m$. If mixed probes are used, it is preferable to use tetramethyl ammonium chloride (TMAC) instead of SSC (Ausubel, 1978-1995, 1999 and 2003).

To obtain the various above noted naturally occurring Cari-like sequences, standard procedures of screening and isolation of naturally-derived DNA or RNA samples from various tissues may be employed using the natural Cari cDNA or portion thereof as probe (see, for example, standard procedures set forth in Sambrook et al, 1989).

The caspase binding polypeptide of the invention could be identified by the above immunoprecipitation with mAb 179 specific to C-terminal domain of the Sub-1 of caspase-8. However in the above immunoprecipitation assay, antibody specific to the C-terminal domain of the Sub-1 from a different caspase than caspase-8 can be used in exchange. The invention also relates to a polypeptide or protein substantially corresponding to Cari. The term "substantially corresponding" includes not only Cari polypeptide but also polypeptides or proteins that are muteins thereof. They may also comprise the corresponding "fusion proteins", i.e., polypeptides comprising Cari or a mutation thereof fused with another protein and having a longer half-life in body fluids. CARI can therefore be fused with another protein such as, for example, an immunoglobulin, a high molecular weight polymer, such as polyethylene glycol (PEG), or the like.

Muteins that substantially correspond to Cari polypeptide are those polypeptides in which one or more amino acid of the caspase-8 interacting protein's amino acid sequence has been replaced with another amino acid, deleted and/or inserted, except a mutein exhibiting Glycine at amino acid residue 230 in place of Glutamic acid and provided that the resulting polypeptide exhibits substantially the same or higher biological activity as the Cari to which it corresponds.

In order to substantially correspond to Cari, the changes in the sequence of Cari, such as isoforms are generally relatively minor. Although the number of changes may be more than ten, preferably there are no more than ten changes, more preferably no more than five, and most preferably no more than three such changes. While any technique can be used to find potentially biologically active polypeptides, which substantially correspond to polypeptide Cari, one such technique is the use of conventional mutagenesis techniques on the DNA encoding the polypeptide, resulting in a few modifications. The polypeptides expressed by such clones can then be screened for their ability to bind to caspase-8 and/or to modulate caspase-8 activity in modulation/mediation of the intracellular pathways noted above.

"Conservative" changes are those changes, which would not be expected to change the activity of the polypeptide, and are usually the first to be screened as these would not be expected to substantially change the size, charge or configuration of the polypeptide and thus would not be expected to change the biological properties thereof.

Conservative substitutions of Cari polypeptide include a mutein wherein at least one amino acid residue in the polypeptide has been conservatively replaced by a different amino acid. Such substitutions preferably are made in accordance with the following list as presented in Table IA, which substitutions may be determined by routine experimentation to provide modified structural and functional properties of a synthesized polypeptide molecule while maintaining the biological activity characteristic of Cari polypeptide.

TABLE IA

| Original Residue | Exemplary Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Alternatively, another group of substitutions of Cari are those in which at least one amino acid residue in the polypeptide has been removed and a different residue inserted in its place according to the following Table IB. The types of substitutions, which may be made in the polypeptide, may be based on analysis of the frequencies of amino acid changes between a homologous polypeptide of different species, such as those presented in Table 1-2 of Schulz et al (1979), and FIGS. 3-9 of Creighton TE (1983). Based on such an analysis, alternative conservative substitutions are defined herein as exchanges within one of the following five groups:

TABLE IB

| 1. | Small aliphatic, nonpolar or slightly polar residues: Ala, Ser, Thr (Pro, Gly); |
| 2. | Polar negatively charged residues and their amides: Asp, Asn, Glu, Gln; |
| 3. | Polar, positively charged residues: His, Arg, Lys; |
| 4. | Large aliphatic nonpolar residues: Met, Leu, Ile, Val (Cys); and |
| 5. | Large aromatic residues: Phe, Tyr, Trp. |

The three amino acid residues in parentheses above have special roles in protein architecture. Gly is the only residue lacking any side chain and thus imparts flexibility to the chain. This, however, tends to promote the formation of secondary structure other than a-helical. Pro, because of its unusual geometry, tightly constrains the chain and generally tends to promote beta-turn-like structures, although in some cases Cys can be capable of participating in disulfide bond formation, which is important in protein folding. Note that Schulz et al (1979) would merge Groups 1 and 2, above. Note also that Tyr, because of its hydrogen bonding potential, has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and substitutions according to the present invention are those, which do not produce radical changes in the characteristics of the protein or polypeptide molecule. "Characteristics" is defined in a non-inclusive manner to define both changes in secondary structure, e.g., a-helix or beta-sheet, as well as changes in biological activity, e.g., binding to caspase-8 and/or mediation of the effect of caspase-8 on cell death.

Examples of production of amino acid substitutions in proteins which can be used for obtaining muteins of caspase-8 interacting polypeptide Cari for use in the present invention include any known method steps, such as presented in U.S. Pat. Nos. RE 33,653, 4,959,314, 4,588,585 and 4,737,462 to Mark et al; U.S. Pat. No. 5,116,943 to Koths et al, U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 to Shaw et al Besides conservative substitutions discussed above which would not significantly change the activity of polypeptide Cari, either conservative substitutions or less conservative and more random changes, which lead to an increase in biological activity of the muteins of Cari polypeptide, are intended to be within the scope of the invention.

When the exact effect of the substitution or deletion is to be confirmed, one skilled in the art will appreciate that the effect of the substitution(s), deletion(s), etc., will be evaluated by routine binding and cell death assays. Screening using such a standard test does not involve undue experimentation.

Acceptable Cari muteins are those, which retain at least the capability of interacting with pro-caspase-8, and thereby, regulate the activity of caspase-8 in the intracellular pathways. In one embodiment Cari was found to increase cell death mediated by Fas, probably by increasing the rate of pro-caspase-8 conversion into active caspase-8. Once caspase-8 is formed it cleaves Cari causing probably its inactivation. A non-cleavable mutein of Cari (Cari D600E mutant) was generated and found to be more potent than the wild type polypeptide in cell death induction. Non-cleavable mutants and preferably the p72 D600E mutant can be used in certain situations where it may be desired to increase caspase-8 activity. Mutein polypeptides can be produced which have a so-called dominant-negative effect, namely, a polypeptide which is defective either in binding to caspase-8, or in subsequent signaling or other activity following such binding. Muteins can be used, for example, to inhibit the cytotoxic effect of caspase-8, or to increase it, depending on whether it is desired to increase cell death or cell survival and depending on which of these activities is the major one modulated by the interaction of Cari and caspase-8 (see above), and this by such muteins competing with the natural Cari polypeptide for binding to or interacting with caspase-8.

At the genetic level, muteins are generally prepared by site-directed mutagenesis of nucleotides in the DNA encoding the Cari polypeptide, thereby producing DNA encoding the mutein, and thereafter synthesizing the DNA and expressing the polypeptide in recombinant cell culture. The muteins typically exhibit the same or increased qualitative biological activity as the naturally occurring polypeptide, Ausubel et al (1978-1995, 1999 and 2003); Sambrook et al (1989).

Preparation of a Cari in accordance herewith, or an alternative nucleotide sequence encoding the same polypeptide but differing from the natural sequence due to changes permitted by the known degeneracy of the genetic code, can be achieved by site-specific mutagenesis of DNA that encodes an earlier prepared muteins or a native version of a Cari polypeptide. Site-specific mutagenesis allows the production of muteins through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 complementing nucleotides on each side of the sequence being altered. In general, the technique of site-specific mutagenesis is well known in the art, as exemplified by publications such as Adelman et al (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al (1981), the disclosure of which is incorporated herein by reference. These phages are readily available commercially and their use is generally well known to those skilled in the art. Alternatively, plasmid vectors that contain a single-stranded phage origin of replication (Vieira et al, 1987) may be employed to obtain single-stranded DNA.

In general, site-directed mutagenesis in accordance herewith is performed by first obtaining a single-stranded vector that includes within its sequence a DNA sequence that encodes the relevant polypeptide. An oligonucleotide primer bearing the desired mutated sequence is prepared synthetically by automated DNA/oligonucleotide synthesis. This primer is then annealed with the single-stranded protein-sequence-containing vector, and subjected to DNA-polymerizing enzymes such as E. coli polymerase I Klenow fragment, to complete the synthesis of the mutation-bearing strand. Thus, a mutated sequence and the second strand bear the desired mutation. This heteroduplex vector is then used to transform appropriate cells, such as E. coli JM101 cells, and clones are selected that include recombinant vectors bearing the mutated sequence arrangement.

After such a clone is selected, the mutated Cari sequence may be removed and placed in an appropriate vector, generally a transfer or expression vector of the type that may be employed for transfection of an appropriate host.

Accordingly, gene or nucleic acid encoding for Cari can also be detected, obtained and/or modified, in vitro, in situ and/or in vivo, by the use of known DNA or RNA amplification techniques, such as polymerase chain reaction (PCR) and chemical oligonucleotide synthesis. PCR allows for the amplification (increase in number) of specific DNA sequences by repeated DNA polymerase reactions. This reaction can be used as a replacement for cloning; all that is required is knowledge of the nucleic acid sequence. In order to carry out PCR, primers are designed which are complementary to the sequence of interest. The primers are then generated by automated DNA synthesis. Because primers can be designed to hybridize to any part of the gene, conditions can be created such that mismatches in complementary base pairing can be tolerated. Amplification of these mismatched regions can lead to the synthesis of a mutagenized product resulting in the generation of a peptide with new properties (i.e., site directed mutagenesis). See also, e.g., Ausubel (1978-1995, 1999 and 2003), Chapter 16.

Furthermore, PCR primers can be designed to incorporate new restriction sites or other features such as termination codons at the ends of the gene segment to be amplified. This placement of restriction sites at the 5' and 3' ends of the amplified gene sequence allows for gene segments encoding Cari polypeptide or a fragment thereof to be custom designed for ligation other sequences and/or cloning sites in vectors.

PCR and other methods of amplification of RNA and/or DNA are well known in the art and can be used according to the present invention without undue experimentation, based on the teaching and guidance presented herein. Known methods of DNA or RNA amplification include, but are not limited to polymerase chain reaction and related amplification processes (see, e.g., U.S. Pat. Nos. 4,683,195, 4,683,202, 4,800,159, 4,965,188, to Mullis et al; U.S. Pat. Nos. 4,795,699 and 4,921,794 to Tabor et al; U.S. Pat. No. 5,142,033 to Innis; U.S. Pat. No. 5,122,464 to Wilson et al; U.S. Pat. No. 5,091,310 to Innis; U.S. Pat. No. 5,066,584 to Gyllensten et al; U.S. Pat. No. 4,889,818 to Gelfand et al; U.S. Pat. No. 4,994,370 to Silver et al; U.S. Pat. No. 4,766,067 to Biswas; U.S. Pat. No. 4,656,134 to Ringold; and Inniset al, 1990) and RNA mediated amplification which uses anti-sense RNA to the target sequence as a template for double stranded DNA synthesis (U.S. Pat. No. 5,130,238 to Malek et al, with the tradename NASBA); and immuno-PCR which combines the use of DNA amplification with antibody labeling (Ruzicka et al (1993); Sano et al (1992); Sano et al (1991), the entire contents of which patents and reference are entirely incorporated herein by reference.

In an analogous fashion, biologically active fragments of Cari (e.g., those of any of the Cari polypeptides or its isoforms) may be prepared as noted above with respect to the muteins of Cari. Suitable fragments of Cari are those which retain the pro-caspase-8 binding protein capability and which can mediate the biological activity of Cari or other proteins associated with caspase-8 directly or indirectly. Alternatively, suitable fragments of Cari are those which retain the pro-caspase-8 binding protein capability and which can inhibit the biological activity of Cari or other proteins associated with caspase-8 directly or indirectly. Accordingly, Cari fragments can be prepared which have a dominant-negative or a dominant-positive effect as noted above with respect to the muteins. It should be noted that these fragments represent a special class of the muteins of the invention, namely, they are defined portions of Cari derived from the full Cari sequence (e.g., from that of any one of the Cari protein or its isoforms), each such portion or fragment having any of the above-noted desired activities. Such fragment may be, e.g., a peptide.

Similarly, derivatives may be prepared by standard modifications of the side groups of one or more amino acid residues of the Cari polypeptide, its muteins or fragments, or by conjugation of the Cari polypeptide, its muteins or fragments, to another molecule, e.g., an antibody, enzyme, receptor, etc., as are well known in the art. Accordingly, "derivatives" as used herein covers derivatives which may be prepared from the functional groups which occur as side chains on the residues or the N- or C-terminal groups, by means known in the art, and are included in the invention. Derivatives may have chemical moieties such as carbohydrate or phosphate residues, provided such a derivative has the same or higher biological activity as Cari polypeptide.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (for example, that of seryl or threonyl residues) formed with acyl moieties.

The term "derivatives" is intended to include only those derivatives that do not change one amino acid to another of the twenty commonly occurring natural amino acids.

As described above, the cleavage assays may be used to determine whether Cari polypeptide and muteins are cleaved by caspase-8.

In an embodiment of the present invention, the cleavage site (D600) was further determined by preparing deletion mutants or point mutations of Cari and testing each deletion and point mutant for its susceptibility to cleavage by caspase-8 as described above. Deletion mutants may be constructed by PCR cloning of desired fragments of the polypeptide to be tested, using the DNA sequence of the clone coding for said polypeptide to be tested as a template. The PCR amplified fragments may then be inserted into expression vectors, whereby an ATG start codon and preferably, a Kozak sequence (Kozak, 1984) must be provided. Further details on expressing polypeptides may be found in the above-noted information of Qiagen, relating to his-tagged proteins, but also to protein expression in general. Another reference for protein expression of the further above-mentioned Ausubel (1978-1995, 1999 and 2003), and specifically Chapter 16 therein.

The cleavage site of a polypeptide to be tested may thus be defined by preparing various deletion mutants therefrom and determining the smallest such deletion mutant that is cleaved by caspase-8.

Another way of identifying the cleavage site uses peptides, which are generated according to the predicted polypeptide sequence of the clone to be tested. Peptides may be synthesized chemically, e.g., as detailed in Bodanszky and Bodanszky (1984), and Bodanszky (1993). Custom peptide synthesis is further available from several commercial companies, e.g., SynPep Corp., Dublin, Calif. USA, and California Peptide Research, Inc., Napa, Calif., USA. Peptides may also be produced, either as fusion with other proteins or unfused, by expressing recombinant DNA coding therefore, as detailed in Chapter 16 of Ausubel (1978-1995, 1999 and 2003).

In order to use peptides for mapping the cleavage site of a polypeptide to be tested, the predicted amino acid sequence of said polypeptide is divided into areas and a peptide corresponding to each area is synthesized. In addition, peptides comprising about half of the amino acids of one area and contiguously comprising further about half of the amino acids of a directly neighboring area are synthesized, so as to be overlapping the border between the two areas. The areas comprise between 5 and 100 amino acids, preferably between 9 and 40 amino acids, and most preferably between 20 and 30 amino acids. After the cleavage reaction, they may therefore be analyzed directly by SDS polyacrylamide gel electrophoresis and UV detection or visualization by staining, e.g., using Coomassie blue. Alternatively, peptides may be labeled for easier detection, e.g., by isotopic end labeling (see, e.g., Shevchenko et al, 1997).

After a peptide screen as described above has been completed, the peptide which is now known to comprise the cleavage site for caspase-8 can be further studied be repeating the same technique, but choosing smaller areas selected from the sequence of the peptide that has been identified.

The actual cleavage site of the peptides should conform to the caspase cleavage sequence XXXD (see Boldin et al, 1996 and Nicholson et al, 1997). The contribution of each amino acid in the peptide may be evaluated by preparing peptides that are mutated in one amino acid and testing these mutated peptides for susceptibility to cleavage with caspase-8. The amino acid to be mutated is preferably replaced by an amino acid selected from the group of charged non-polar amino acids (see Lehninger,), most preferably selected from glycine or alanine.

By mutating critical amino acids, it is possible to generate peptides that bind pro-caspase-8, but are not susceptible to cleavage thereby. Binding may be tested by size separation of peptide-caspase-8 complexes under non-denaturing conditions using acrylamide gel electrophoresis or by co-precipitation with caspase-8 specific antibodies.

The polypeptide to be tested, or a peptide fragment thereof, may be further characterized by introducing said polypeptide or peptide into a mammalian cell and measuring the effect of apoptosis-including reagents in said cell.

Expression of a Cari polypeptide or peptide in a mammalian cell may be done by inserting the DNA coding for Cari into a vector comprising a promoter, optionally an intron sequence and splicing donor/acceptor signals, and further optionally comprising a termination sequence. These techniques are in general described in Ausubel (1978-1995, 1999 and 2003), Chapter 16.

The above promoter, intron, and termination sequences are operable in mammalian cells. The promoter is preferably a strong promoter such as the above-noted RSV, CMV, or MPSV promoter. The promoter may also be the SV40 early promoter (Everett, et al, 1983, and references therein), or a cellular promoter, such as the beta-actin promoter or the ELF-1 promoter (Tokushige et al, 1997). Also, a hybrid promoter may be used, such as the hybrid between the lac operator and the human ELF-1 alpha promoter as described by Edamatsu et al, 1997, the CMV-beta actin hybrid promoter described by Akagi et al (1997), or the hybrid between tet operator sequences and the CMV promoter (Furth et al, 1994, and references therein).

Intron sequences, which may be inserted as complete sequences, i.e., including the splice donor and acceptor sites, may be inserted into the coding sequence of the polypeptide, which it is desired to express. Insertion if such intron sequences may enhance RNA stability and thus enhance production of the desired polypeptide. While, in principle, suitable intron sequences may be selected from any gene containing introns, preferred intron sequences are the beta-actin intron, the SV 40 intron, and the p55 TNF receptor intron.

The intron sequence may contain enhancer elements, which may enhance transcription from the above-noted promoters.

Often, intron sequences also contain transcriptional or translational control sequences that confer tissue specific expression. Therefore, when it is desired to express a polypeptide of the invention in a tissue-specific manner, such intron sequences may be advantageously employed. An example of an intron containing tissue-specific enhancer elements is the erythroid-specific enhancer located in intron 8 of the human 5-aminolevulinate synthase 2 gene (Surinya et al, 1998), and a discussion of the principle of enhancing protein production using intron sequences, together with example intron sequences, is provided in Huang et al, 1990.

Transcriptional termination sequences and polyadenylation signals may be added at the 3' end of the DNA coding for the polypeptide that it is desired to express. Such sequences may be found in many or even most genes. Advantageously, the SV 40 polyadenylation signal can be used (Schek et al, 1992, and references therein).

Vectors for expression of Cari in a mammalian cell could be used, for example, the pcDNA3.1 vector (Invitrogen), which contains the CMV promoter for driving expression of the gene encoding the desired polypeptide and pMPSVEH vectors with the MPSV promoters.

Recombinant polypeptides can be produced either in bacterial or eukaryotic (e.g., CHO) cultured host cells transfected with vectors encoding such polypeptides or in transgenic animals. When using transgenic animals, it is particularly advantageous to produce heterologous polypeptides in their milk. Dairy animals such as cattle, sheep and goats are thus preferred hosts. See, for example, patent specifications WO 88/00239, WO 90/05188, WO 91/02318, and WO 92/11757; and U.S. Pat. Nos. 4,873,191; 4,873,316; and 5,304,489, which are incorporated herein by reference in their entirety.

Using recombinant expression of the polypeptide to be tested, the polypeptide can now be evaluated for its effect on the apoptotic signal, which is mediated by a caspase, for example, caspase-8. For that purpose, apoptosis may be induced by either overexpression of an apoptosis-inducing protein, such as the p55 TNFR, the Mort-1 protein, caspase-8, or an equivalent thereof; or activation of an apoptotic signal by triggering p55 TNFR, CD120a, CD95, TRAMP/DR3, or an equivalent receptor. In one embodiment, apoptosis is induced by overexpression of p55 TNFR.

Receptor activation may be achieved also by contacting the receptors with specific ligands or by cross-linking receptors with antibodies, preferably polyclonal antibodies (see Engelmann et al, 1990). In one embodiment overexpression of Cari is followed by stimulation with Fas-ligand.

While in general, triggering of a receptor like CD95 by Fas Ligand requires the addition of a protein synthesis inhibitor like cycloheximide in order to achieve a strong signal for apoptosis, the overexpression of receptor intracellular domains or of proteins involved in apoptosis signal transduction do not (see Boldin et al, 1996). In contrast, when Fas Ligand stimulation was given to cells overexpressing Cari, cycloheximide was not required to achieve a strong signal for apoptosis. The detection of apoptosis, incubation times and other details and parameters for this assay have been described in the above Boldin et al.

Cell death in cells overexpressing Cari, versus control cells, may be evaluated by any number of methods, such as methods based upon DNA fragmentation or detection of apoptosis-specific antigens and epitopes. Reagents and protocols for detection of apoptosis in kit form are available from the above-noted Boehringer Mannheim and other companies.

Cell death may also be determined by evaluating the morphological appearance of the cells. Apoptotic cell death is characterized by a wavy cell membrane and shrinking of the cells in the absence of cell lysis.

Advantageously, a reporter gene is expressed in the mammalian cell, in order to provide a marker for successful transfection. As the transfection procedure by itself results in some cell death, including cell death of cells that have not been transfected, it is of advantage to only evaluate cells that have been transfected. A preferred reporter gene for this purpose is the GFP, the green fluorescent protein, may be used for direct detection without the need for a color reaction, this reporter gene necessitates the use of a fluorescent microscope. However, any other known reporter gene may be used, preferably a gene whose products are easily detected using a simple color reaction, for example, lacZ gene, is easily detected by incubation of transfected cells with Xgal or a similar reagent indicative of active beta-galactosidase the results of which may be evaluated by using a microscope.

Thus, by only considering cells that have been transfected, i.e., that express the reporter gene, and by counting the percentage of cells demonstrating apoptotic morphology, it is possible to evaluate the effect of a particular transfected clone and the polypeptide expressed therefrom on apoptosis.

Mammalian cells to be used for transfection and testing of apoptosis are selected from HeLa cells, human Caucasian chronic myelogenous with lymphoblast morphology (K562), human T cell lymphoma with lymphoblast morphology (Hut78), human Negroid Burkitt's lymphoma with lymphoblast morphology (Raji), Namalwa-human Burkitt's lymphoma with lymphoblast morphology (Nalm), human Caucasian promyelocytic leukemia with promyeloid morphology (HL-60), acute lymphoblastic leukemia with lymphoblast morphology (CEM) and human T cell with lymphoblast morphology (H9) and preferably human embryonic kidney (HEK) 293 cells overexpressing the T antigen cells. The transfection is preferably done by the calcium phosphate method as described in Ausubel (1978-1995, 1999 and 2003). The morphology of the cells if evaluated one to 150 hours after transfection, preferably 4 to 35 hours and most preferably 24 hours after transfection.

The use of a vector for inducing and/or enhancing the endogenous production of Cari or an inhibitor of Cari normally silent, are also contemplated according to the invention. The vector may comprise regulatory sequences functional in the cells desired to express Cari or the inhibitor of Cari. Such regulatory sequences may be, for example, promoters or enhancers. The regulatory sequence may then be introduced into the right locus of the genome by homologous recombination, thus operably linking the regulatory sequence with the gene, the expression of which is required to be induced or enhanced. The technology is usually referred to as "endogenous gene activation" (EGA), and it is described, e.g., in WO 91/09955.

It will be understood by the person skilled in the art that it is also possible to shut down Cari expression using the same technique, i.e., by introducing a negative regulation element, like, e.g., a silencing element, into the gene locus of Cari, thus leading to down-regulation or prevention of Cari expression. The person skilled in the art will understand that such down-regulation or silencing of Cari expression has the same effect as the use of a Cari inhibitor in order to prevent and/or treat disease.

The clones obtained in the screening of caspase binding polypeptides by the method of the invention may be partial clones. The generation of complete clones, if necessary, has been described further above. The DNA sequence of a complete clone and of the partial clone initially found in the screening of the invention may find a variety of uses.

For example, in order to manipulate the expression of Cari, it may be desirable to produce antisense RNA in a cell. For this purpose, the complete or partial cDNA, preferably 9 nucleotides, coding for Cari polypeptide is inserted into an expression vector comprising a promoter, as noted further above. The 3' end of the cDNA is thereby inserted adjacent to the 3' end of the promoter, with the 5' end of the cDNA being separated from the 3' end of the promoter by said cDNA. Upon expression of the cDNA in a cell, an antisense RNA is therefore produced which is incapable of coding for the polypeptide. The presence of antisense RNA in the cell reduces the expression of the cellular (genomic) copy of the Cari.

For the production of antisense RNA, the complete cDNA may be used. Alternatively, a fragment thereof may be used, which is preferably between about 9 and 2,000 nucleotides in length, more preferably between 15 and 500 nucleotides, and most preferably between 20 and 150 nucleotides.

A synthetic oligonucleotide may be used as antisense oligonucleotide. The oligonucleotide is preferably a DNA oligonucleotide. The length of the antisense oligonucleotide is preferably between 9 and 150, more preferably between 12 and 60, and most preferably between 20 and 50 nucleotides, for example, the sequence in SEQ ID NO:6 and SEQ ID NO:7.

The mechanism of action of antisense RNA and the current sate of the art of use of antisense tools is reviewed in Kumar et al (1998). The use of antisense oligonucleotides in inhibition of BMP receptor synthesis has been described by Yeh et al (1998). The use of antisense oligonucleotides for inhibiting the synthesis of the voltage-dependent potassium channel gene Kv1.4 has been described by Meiri et al (1998). The use of antisense oligonucleotides for inhibition of the synthesis of Bcl-x has been described by Kondo et al (1998).

The therapeutic use of antisense drugs is discussed by Stix (1998), Flanagan, (1998), Guinot and Temsamani, (1998), and references therein.

Modifications of oligonucleotides that enhance desired properties are generally used when designing antisense oligonucleotides. For instance, phosphorothioate bonds are used instead of the phosphoester bonds naturally occurring in DNA, mainly because such phosphorothioate oligonucleotides are less prone to degradation by cellular enzymes. Peng et al teach that undesired in vivo side effects of phosphorothioate oligonucleotides may be reduced when using a mixed phosphodiester-phosphorothioate backbone. Preferably, 2'-methoxyribonucleotide modifications in 60% of the oligonucleotide are used. Such modified oligonucleotides are capable of eliciting an antisense effect comparable to the effect observed with phosphorothioate oligonucleotides. Peng et al (2001) teach further that oligonucleotide muteins incapable of supporting ribonuclease H activity are inactive.

Therefore, the preferred antisense oligonucleotide of the invention has a mixed phosphodiester-phosphorothioate backbone. Most preferably, 2'-methoxyribonucleotide modifications in about 30% to 80%, most preferably about 60% of the oligonucleotide are used.

Further modification may be introduced to an antisense oligonucleotide. For instance, the oligonucleotide molecule may be linked to a group comprising optionally partially unsaturated aliphatic hydrocarbon chain and one or more polar or charged groups such as carboxylic acid groups, ester groups, and alcohol groups. Alternatively, oligonucleotides may be linked to peptide structures, which are preferably membranotropic peptides. Such modified oligonucleotide penetrates membranes more easily, which is critical for their function and may therefore significantly enhance their activity. Membrane permeability is especially desirable for antisense drugs that are desired to reach the brain. Palmityl-linked oligonucleotides have been described by Gerster et al (1998). Geraniol-linked oligonucleotides have been described by Shoji et al, (1998). Oligonucleotides linked to peptides, e.g., membranotropic peptides, and their preparation have been described by Soukchareun et al, (1998). Modifications of antisense molecules or other drugs that target the molecule to certain cells and enhance uptake of the oligonucleotide by said cells are described by Wang (1998).

Given the known mRNA sequence of a gene, ribozymes may be designed, which are RNA molecule that specifically bind and cleave said mRNA sequence (see, e.g., Chen et al, 1992, Zhao and Pick 1993, Shore et al, 1993, Joseph and Burke, 1993, Shimayama et al, 1993, Cantor et al, 1993).

Accordingly, ribozyme-encoding RNA sequence may be designed that cleave the mRNA of a Cari polypeptide of the invention. The point of cleavage is preferably located in the coding region or in the 5' non-translated region, more preferably, in the 5' part of the coding region close to the AUG translation start codon.

A DNA encoding a ribozyme according to the invention may be introduced into cells by way of DNA uptake, uptake of modified DNA (see modifications for oligonucleotides and proteins that result in enhanced membrane permeability, as described herein below), or viral vector-mediated gene transfer as detailed herein below.

The present invention provides therefore Cari, peptides derived therefrom, mutants, specific antibodies, DNA encoding the protein, ribozyme, antisense DNA molecules, and oligonucleotides. A therapeutic or research-associated use of these tools necessitates their introduction into cells of a living organism. For this purpose, it is desired to improve membrane permeability of peptides, polypeptides and oligonucleotides. Derivatization with lipophilic structures may be used in creating peptides and polypeptides with enhanced membrane permeability. For instance, the sequence of a known membranotropic peptide as noted above may be added to the sequence of the peptide or polypeptide. Further, the peptide or polypeptide may be derivatized by partly lipophilic structures such as the above-noted hydrocarbon chains, which are substituted with at least one polar or charged group. For example, lauroyl derivatives of peptides have been described by Muranishi et al (1991). Further modifications of peptides and polypeptides comprise the oxidation of methionine residues to thereby create sulfoxide groups, as described by Zacharia et al (1991). Zacharia and co-workers also describe peptide or derivatives wherein the relatively hydrophobic peptide bond is replaced by its ketomethylene isoester ($COCH_2$). These and other modifications known to the person of skill in the art of polypeptide and peptide chemistry enhance membrane permeability.

Another way of enhancing membrane permeability is the use receptors, such as virus receptors, on cell surfaces in order to induce cellular uptake of the peptide or polypeptide. This mechanism is used frequently by viruses, which bind specifically to certain cell surface molecules. Upon binding, the cell takes the virus up into its interior. The cell surface molecule is called a virus receptor. For instance, the integrin molecules CAR and AdV have been described as virus receptors for Adenovirus, see Hemmi et al (1998), and references therein. The CD4, GPR1, GPR15, and STRL33 molecules have been identified as receptors/co-receptors for HIV, see Edinger et al (1998) and references therein.

Thus, conjugating peptides, polypeptides or oligonucleotides to molecules that are known to bind to cell surface receptors will enhance membrane permeability of said peptides, polypeptides or oligonucleotides. Examples for suitable groups for forming conjugates are sugars, vitamins, hormones, cytokines, transferrin, asialoglycoprotein, and the like molecules. Low et al U.S. Pat. No. 5,108,921, describes the use of these molecules for the purpose of enhancing membrane permeability of peptides, polypeptides and oligonucleotides, and the preparation of said conjugates.

Low and co-workers further teach that molecules such as folate or biotin may be used to target the conjugate to a multitude of cells in an organism, because of the abundant and unspecific expression of the receptors for these molecules.

The above use of cell surface proteins for enhancing membrane permeability of a peptide, polypeptide or oligonucleotide of the invention may also be used in targeting said peptide, polypeptide or oligonucleotide of the invention to certain cell types or tissues. For (instance, if it is desired to target cancer cells, it is preferable to use a cell surface protein that is expressed more abundantly on the surface of those cells. Examples are the folate receptor, the mucin antigens MUC1, MUC2, MUC3, MUC4, MUC5AC, MUC5B, and MUC7, the glycoprotein antigens KSA, carcinoembryonic antigen, prostate-specific membrane antigen (PSMA), HER-2/neu, and human chorionic gonadotropin-beta. The above-noted Wang et al (1998), teaches the use of folate to target cancer cells, and Zhang et al (1998), teaches the relative abundance of each of the other antigens noted above in various types of cancer and in normal cells.

The polypeptide, peptide or oligonucleotide of the invention may therefore, using the above-described conjugation techniques, be targeted to certain cell type as desired. For instance, if it is desired to enhance apoptosis in cells of the lymphocytic lineage, Cari peptide, fragment thereof, mutants and derivatives of the invention may be targeted at such cells, for instance, by using the MHC class II molecules that are expressed on these cells. This may be achieved by coupling an antibody, or the antigen-binding site thereof, directed against the constant region of said MHC class II molecule to the polypeptide or peptide of the invention. Further, numerous cell surface receptors for various cytokines and other cell communication molecules have been described, and many of these molecules are expressed with in more or less tissue- or cell-type restricted fashion. Thus, when it is desired to target a subgroup of T cells, the CD4 T cell surface molecule may be used for producing the conjugate of the invention. CD4-binding molecules are provided by the HIV virus, whose surface antigen gp42 is capable of specifically binding to the CD4 molecule. An apoptosis-enhancing Cari, mutant or peptide of the invention may be advantageously targeted to T cells in the treatment of patient who suffer from autoimmune reactions based upon T cells, such as lupus erythematodes patients.

The polypeptides, peptides and antisense sequences of the invention may be introduced into cells by the use of a viral vector. The use of vaccinia vector for this purpose is detailed in the Chapter 16 of Ausubel (1978-1995, 1999 and 2003). The use of adenovirus vectors has been described, e.g., by Teoh et al (1998), Narumi et al (1998), Pederson et al (1998), Guang-Lin et al (1998), and references therein, Nishida et al (1998), Schwarzenberger et al (1998), and Cao et al (1998). Retroviral transfer of antisense sequences has been described by Daniel et al (1998).

In order to treat and/or prevent diseases in which Cari is involved, a gene therapy vector comprising the sequence of an inhibitor of Cari, if inhibition of apoptosis is required, or alternatively comprising the sequence of Cari if enhancement of apoptosis is required, for either inhibition or induction of Cari production and/or action respectively, may be injected directly into the diseased joint, for example, thus avoiding problems involved in systemic administration of gene therapy vectors, like dilution of the vectors, reaching and targeting of the target cells or tissues, and of side effects.

When using viruses as vectors, the viral surface proteins are generally used to target the virus. As many viruses, such as the above adenovirus, are rather unspecific in their cellular tropism, it may be desirable to impart further specificity by using a cell-type or tissue-specific promoter. Griscelli et al (1998) teach the use of the ventricle-specific cardiac myosin light chain 2 promoter for heart-specific targeting of a gene whose transfer is mediated by adenovirus.

Alternatively, the viral vector may be engineered to express an additional protein on its surface, or the surface protein of the viral vector may be changed to incorporate a desired peptide sequence. The viral vector may thus be engineered to express one or more additional epitopes, which may be used to target, said viral vector. For instance, cytokine epitopes, MHC class II-binding peptides, or epitopes derived from homing molecules may be used to target the viral vector in accordance with the teaching of the invention.

Thus, Cari can be used for gene therapy by reducing or increase the endogenous amount of Cari at a desired site in a human patient.

The interaction of Cari with caspase-8 has several possible consequences:

The first is modulation of apoptosis. This is demonstrated herein in an in vivo assay wherein overexpressed Cari potentiates apoptosis induced by overexpression of p55TNFR, P72 overexpression or by stimulation with Fas-ligand. In one embodiment, the non-cleavable mutant p72 D600E was shown to be more potent in Fas-ligand cell death potentiation than the wild type Cari. One possible explanation for this result may be that Cari is involved in the conversion of pro-caspase-8 into active caspase-8. Therefore a non-cleavable Cari will continuously induce conversion of pro caspase-8 into active caspase-8 and increase apoptosis unlike the wild type Cari, which can be progressively cleaved and inactivated by active caspase-8. Cari has RNA binding motifs; therefore, its mechanism of action may involve changes in translation rate and/or turnover of different mRNA transcripts, which consequently effect the expression of key proteins involved in modulation of cell death.

Secondly, the activity of Cari may be modulated. This is demonstrated herein by the ability of caspase-8 to cleave Cari. It is likely that Cari is inactivated by the cleavage. However, it is also possible that the activity of the Cari is changed, that novel activities are induced, or that the Cari polypeptide is activated by cleavage, just as the caspases themselves.

Consequently, Cari, mutants, preferably the Cari/p72 D600E mutant, the peptides, for example the caspase-8 binding domain in Cari comprising amino acid residues from 414 to 437 (SEQ ID NO:4) and from residues 422 to 437 (SEQ ID NO:5), oligonucleotides such as Cari antisense and specific antibodies for Cari are useful in modulating the activity of caspase-8 and apoptosis.

Down-regulation of caspase-8 is desirable in situations where excessive cell death by apoptosis occurs. For instance, in inflammatory diseases such as multiple sclerosis with primary oligodendrogliopathy, autoimmune uveoretinitis, diabetes, lupus, autoimmune myocarditis I, acute liver failure regardless of etiology, HCV-mediated chronic hepatitis, chronic gastritis, e.g., type A gastritis, mixed connective tissue disease, (MCTD), Crohn's disease, and ulcerative colitis, it has been suggested that destruction of body tissue is caused by apoptotic signals. Therefore, it may be beneficial to patients suffering from these diseases to down-modulate caspase-8 activity in those cells that are destroyed by apoptotic cell death.

Similarly, the peptides or polypeptides of the invention such as Cari 414-437 and Cari 422-437 may be targeted to other cell type involved in other diseases listed above and other diseases where an excess of apoptotic cell death has been shown to mediate the damage in body tissue observed.

Up-regulation of caspase-8 activity and increase of apoptosis by Cari may be employed in situations where excessive cell death is required.

For instance, in the above oligodendropathy, it is desired to inhibit caspase-8 activity, in oligodendrocytes. The cell surface G-protein-coupled phospholipid lysophosphatidic acid receptor is expressed in oligodendrocytes and in various other brain cells, but not in other tissues of the body. Since it has been demonstrated in one of the embodiments that TNF receptor signaling pathway or caspase-8 dependent apoptosis requires the activity of CARI a small peptide of Cari, for example, the Cari polypeptide of 24 amino acid (Cari 414-437), which was found to bind caspase-8, can be targeted to the oligodendrocytes to inhibit apoptosis mediated by caspase-8. This may be achieved by either coupling said peptide or polypeptide to phospholipid lysophosphatidic acid, or by introducing the sequence of an antibody that specifically recognizes said phospholipid lysophosphatidic acid receptor into a viral vector, so that said viral vector specifically binds to said phospholipid lysophosphatidic acid receptor.

Also, the antisense RNA, antisense oligonucleotide with sequences derived from human Cari cDNA's, such as, AAGAGGATAAGGTAGAGCTCC (1169-1190) (SEQ ID NO:6) and/or from 3'-non-translated region AATGAC-CAACCGTCCCTGGAC (3' 26-47 bp) (SEQ ID NO:7), and ribozyme of the invention may be targeted similarly to the above oligodendrocytes, or corresponding cells in other diseases. In that case, the expression of Cari polypeptide is inhibited, rather than the expression of caspase-8 itself. Inhibiting the expression of Cari may decrease the apoptotic effect of caspase-8. However, decreasing the expression of Cari polypeptides may actually increase the effect of caspase-8, as certain endogenous Cari polypeptides are capable of acting as a negative regulator of caspase-8 activity. The effect of using antisense oligonucleotides and antisense RNA, and of ribozymes must therefore be first tested, e.g., in the above-described assay, before such agents are considered for treatment.

On the other hand, there are certain situations where it may be desired to increase caspase-8 activity. This may be the case in the same disease as noted above, e.g., in systemic lupus erythematodes. However, the cell types that are to be targeted are different. For instance, in Lupus, the T cell population may contain autoreactive cells that are not destroyed in the thymus. Therefore, the caspase-8 up-regulating agent of the invention should be targeted to T cells. It is preferable to target the caspase-8 up-regulating agent to autoreactive cells. In some diseases, such as multiple sclerosis, certain T cell clones are presumed to play a critical role in development of the disease. The caspase8 up-regulating agent according to the invention may therefore be targeted to such cells, by using one or more antibodies specifically directed at the variable region of the T cell receptor of the autoreactive T cell clones, for targeting the caspase-8 up-modulating agent of the invention, which may be a Cari polypeptide, mutants or a peptide according to the invention.

Increasing caspase-8 activity and apoptosis by Cari can be used also for treating cancer.

The present invention encompasses pharmaceutical compositions comprising an active substance selected from one or more of a Cari polypeptide, mutants, preferably p72 D600E, a peptide such as the one comprising amino acid residues from 414 to 437 (SEQ ID NO:4) and amino acid residues from 422 to 437 (SEQ ID NO:5), vectors encoding such Cari, muteins thereof and fragments an antibody specific for Cari, a ribozyme, antisense RNA, or antisense oligonucleotide according to the invention.

The therapeutically effective amounts of the active protein(s) will be a function of many variables, e.g., the route of administration, the clinical condition of the patient.

A "therapeutically effective amount" is such that when administered, Cari or its antagonist, exhibit biological activity. The dosage administered, as single or multiple doses, to an individual will vary depending upon a variety of factors, including pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the effect in an individual.

The invention further encompasses pharmaceutical compositions comprising a viral vector capable of infecting mammalian cells wherein said vector comprises an operably linked promoter and a DNA sequence of the invention coding for a Cari, mutants (e.g., p72 D600E), peptide (e.g., Cari 414-437 or Cari 422-437), a ribozyme, an antisense RNA, an antisense oligonucleotide, or a Cari antibody according to the invention. The viral vector may optionally comprise a coding sequence operably linked to a promoter, which encodes a peptide, or protein located on the virus surface and which is capable of binding a surface protein of a mammalian cell. The surface protein is preferably a protein that enables uptake of the viral vector, and is preferably expressed in a tissue- or cell-type specific manner, so as to enable targeting of the viral vector.

Cari, its muteins, fragments or derivatives the p72 D600E mutant, peptides Cari 414-437 or Cari 422-437, a ribozyme, an antisense RNA, an antisense oligonucleotide, or a Cari antibody according to the invention may also be used to isolate, identify and clone other polypeptides of the same class, i.e., those binding to caspase-8 or to isolate functionally related proteases or proteins, involved in the intracellular signaling process.

For this purpose the above immunoprecipitation system may be used, or there may be used a developed system employing non-stringent Southern hybridization followed by PCR cloning (Wilks et al, 1989). In the Wilks et al publication, there is described the identification and cloning of two putative protein-tyrosine kinases by application of non-stringent southern hybridization followed by cloning by PCR based on the known sequence of the kinase motif, a conceived kinase sequence. This approach may be used, in accordance with the present invention using the sequence of the Cari polypeptide to identify and clone those of related Cari polypeptides.

Another approach to utilizing the Cari polypeptide, muteins, fragments or derivatives thereof or Cari antibodies of the invention is to use them in methods of affinity chromatography to isolate and identify other polypeptides or factors to which they are capable of binding, e.g., other polypeptides or factors involved in the intracellular signaling process. Cari, its muteins, fragments or derivatives thereof, Cari antibodies may be individually attached to affinity chromatography matrices and then brought into contact with cell extracts human fluids or isolated polypeptides or factors suspected of being involved in the intracellular signaling process. Following the affinity chromatography procedure, the other polypeptides or factors which bind to the Cari polypeptide, or its muteins, fragments or derivatives thereof of the invention, can be eluted, isolated and characterized.

The present invention also relates to the use of Cari and peptides thereof such as the caspase-8 binding domain in Cari (residues 414-437 or residues 422-437) or Cari antibodies for the preparation of antagonist molecules to Cari, with potential therapeutic value. These methods comprise the use of Cari and fragments thereof for the isolation of natural antagonists, small peptide antagonists and non-peptide chemical antagonists. High throughput screening uses robots to test the binding activity of thousands of compounds (peptides or chemical compounds, e.g., created by combinatorial chemistry) against a Cari target. The compounds tested may be obtained not only through combinatorial chemistry, but also from other high throughput synthesis methods. Automated techniques enable the rapid synthesis of libraries of molecules, large collections of discrete compounds, which can be screened. Compounds may be also screening for inhibiting Cari or Cari (414-437) and caspase-8 interaction. Antagonistic molecules can be also detected by their capability of inhibiting binding of Cari to pro-caspase-8, or inhibiting cell death mediated by Cari, caspase-8 or TNF receptor family ligands. Producing larger and more diverse compound libraries increases the likelihood of discovering a useful drug within the library.

As noted above, Cari its muteins, fragments or derivatives thereof, may also be used as immunogens (antigens) to produce specific antibodies thereto. These antibodies may also be used for the purposes of purification of the Cari polypeptide either from cell extracts or from the medium of transformed cell lines producing Cari polypeptide, or its muteins or fragments. Further, these antibodies may be used for diagnostic purposes for identifying disorders related to abnormal functioning of the caspase-8 mediated Fas or TNF system. Thus, should such disorders be related to a malfunctioning intracellular signaling system involving caspase-8, or a Cari polypeptide, such antibodies would serve as an important diagnostic tool. Such antibodies produced using Cari, especially fully humanized antibodies (e.g., intrabodies, see above), may have also therapeutic value.

It should also be noted that the isolation, identification and characterization of polypeptide according the invention or one of the same class, might be performed using any of the well-known standard screening procedures, for example, one of these screening procedures, the yeast two-hybrid procedure (see Stanger et al, 1995). Likewise, as noted above and below, other procedures may be employed such as affinity chromatography, DNA hybridization procedures, etc. as are well known in the art, to isolate, identify and characterize the polypeptide of the invention or to isolate, identify and characterize additional polypeptides, factors, receptors, etc. which are capable of binding to the polypeptides of the invention.

Having now described the invention, it will be more readily understood by reference to the following examples that are provided by way of illustration and are not intended to be limiting of the present invention.

EXAMPLES

Example 1

Immunization of Mice for Generation of Monoclonal Antibodies Specific to Caspase-8

Following activation, caspase-8 is cleaved and assembled in two sub units (Sub-1 and Sub-2).

For the generation of antibodies specific to new possible epitopes formed following caspase-8 activation, synthetic peptides derived from the C-terminus of Sub-1 and N-terminus of Sub-1 and Sub-2 were used to immunize mice.

The following peptides were used to immunize mice for the generation of monoclonal antibodies:

Peptide 179—The peptide CQGDNYQKGIPVETD (residues 360-374 of SEQ ID NO:8) corresponding to the C-terminus of the large subunit of caspase-8 (Sub-1), (epitope corresponding to residues Cys360-Asp374 FIG. 1) was synthesized purified by reverse HPLC and coupled to the carrier KLH through its natural cysteine, to expose the peptide to the surface of the carrier.

Peptide 182—The peptide LSSPQTRYIPDEADC (SEQ ID NO:9) corresponding to the N-terminus of the small subunit of the caspase-8 (Sub-2, residues Leu385-Asp398) was synthesized purified by reverse HPLC and coupled to carrier KLH through the C which is not derived from the sequence of Sub-2.

Peptide 183—The peptide SESQTLDKVYQMKSKPRC (SEQ ID NO:10) corresponding to the N-terminus of Sub-1 (residues Ser217-Arg233), was synthesized purified by reverse HPLC and coupled to carrier KLH through the C that is not derived from the sequence of Sub-1.

Four immunizations and two boosts with the same amount of antigen (peptide-KLH) were administered to mice as follows:

First immunization with 50 μg of peptide-KLH were dissolved in 50 μl PBS and homogenized with 50 μl complete Freund's Adjuvant and injected into the footpad of each of five 7 week old Balb/C female mice.

For the second immunization, carried out 2 weeks after the first immunization, mice were intramuscularly boosted with the same amount of the peptide in a 50% (v/v) solution of incomplete Freund's adjuvant.

For the third immunization, carried out two weeks after the second immunization, mice were injected intraperitoneal with 50 μg of peptide-KLH in 50 μl PBS.

Sera of the injected mice were tested 10 days after the second and the third immunization.

The fourth immunization (carried only for peptides 182 and 183), was performed a month latter in similar way as the third immunization.

One month after the fourth immunization (or third immunization for mice challenged with peptide 179) two boosts were carried out (in a similar way as the third and fourth immunization) within two-day interval.

Four days latter the spleen and inguinal lymph nodes of the two mice exhibiting the highest specific immunoreactivity were taken for fusion with myeloma cells (Eshhar, 1985).

Example 2

Immunization of Rabbits for Generation of Polyclonal Antibodies Specific to Caspase-8

Rabbits were immunized with 179-KLH and 183-KLH for the generation of specific polyclonal antibodies.

The first immunization was carried out with 100 μg of peptide-KLH which was dissolved in 50 μl PBS and homogenized with 50 μl complete Freund's Adjuvant and injected subcutaneously. A second immunization was carried out two weeks later with the same amount of peptide-KLH and injected intramuscularly two weeks later with incomplete Freund's adjuvant. These two immunizations were followed by two boosts of the same amount of peptide-KLH dissolved in PBS and administered subcutaneously at two weeks interval.

Example 3

Hybridoma Preparation, Selection of Antibody Producing Clones and Purification of Antibodies from Ascites Fluids The fusion process and hybridoma cell selection were performed according to the protocols in Eshhar (1985). Briefly, a mixture of spleen and lymph node cells from 2 reactive mice $110 \times 10^6$ were fused with $32 \times 10^6$ NSO/1 myeloma variant myeloma cells by a short incubation with PEG. The PEG was first slowly diluted with DMEM and then completely removed by centrifugation. The cells were re-suspended in DMEM-HAT medium, distributed in 96 wells plates at a concentration of about $2.5 \times 10^4$ cells/well and incubated in an 8% $CO_2$ incubator at 37° C. The medium in all the hybridoma wells was changed to DMEM supplemented with 10% Horse Serum (HS). Hybridoma culture supernatant samples were screened for the presence of specific mAbs two weeks after the fusion by ELISA (described in Example 12 below). Cells from wells, in which the presence of specific antibodies was detected in the culture supernatant, were transferred to 24 well plates. Positive cells were subcloned twice; at this stage all the sub-clones were found to be positive. The clones were expanded in 24 wells and then to 25 $cm^2$ T-flasks. The expanded cultures were monitored for secretion of specific mAbs. Ampoules of cells from positive cultures were frozen and stored in liquid nitrogen.

Out of approximately 700 clones screened for detecting specific antibodies to peptide 179 only one positive clone was found (mAb 179), out of 700 clones screened for detecting specific antibodies to peptide 182 only 1 positive clone was found (mAb 182) and out of 1100 clones screened for detecting specific antibodies to peptide 183 only 2 positive clones were found (mAbs 183.1 and 183.2). The positive clones were sub-cloned by limiting dilution in 96 well plates. Supernatants from the growing clones were tested several times for specific antibodies by ELISA (described in Example 12).

Positive hybridoma clones were grown in tissue culture flasks in DMEM containing 15% horse serum and ampoules were frozen from part of the cultures. In parallel, cells of different hybridoma clones were injected, to 2-4 mice each, to obtain ascites fluids. The antibodies were purified from ascites fluid by affinity purification using affigel beads (affigel 15 Biorad) cross-linked with BSA (Pierce Cat 77116) coupled to the synthetic peptide used for mice immunization (peptides 179, 182 or 183).

For antibody purification, ascites precipitated by 50% ammonium sulfate was dialyzed against PBS for 16 hours at 0° C. Following dialysis, aliquots were incubated with 1 ml affigel-BSA-peptide beads for 16 hours at 0° C. and the pre-incubated beads were used to pack a 1 ml column. Initially the column was washed with 10 ml PBS, followed by a wash with 10 mM Tris pH 7.5 containing 1 M NaCl and a wash with PBS. The antibodies were eluted from the column with a solution containing 100 mM glycine HCl, pH 2.7 and 0.5M NaCl. 1 ml fractions were collected in tubes containing 40 μl Tris base for the neutralization of the eluent. From 25 ml ascites about 5-13.6 mg-purified antibodies was obtained.

Example 4

Monoclonal Antibodies Isotype

The isotype of monoclonal antibodies was determined using a commercial isotyping kit (Southern Biotechnology Associates, INC cat 5300-05) according to the manufacturer's assay procedure. mAbs 183 and 179 were identified as IgG1, whereas mAb 182 was found to be of the IgM class.

Example 5

Immunoprecipitation of Caspase-8 with mAbs 179, 182 and 183

The different monoclonal anti-caspase-8 antibodies described in the Example 3 above were tested for their capacity to immunoprecipitate caspase-8 (see Example 13 below) from lysates of resting and activated BJAB cells. BJAB line is a continuous lymphoma cell line derived from the African case of Burkitt's lymphoma (Clements et al, 1975). BJAB cells were stimulated with Fas-ligand for one hour. Cell lysates were prepared from BJAB cells before and after stimulation. Following immunoprecipitation with mAbs 179, 182 and 183 (as described in Example 13) the "depleted lysate" and the caspase-8 eluted with the corresponding peptides were analyzed by SDS-PAGE and Silver staining or by Western blot analysis using anti Sub-1 antibody as the first antibody (Cell Signaling Technology Caspase-8 ICI2 Cat 9746).

FIG. 2 shows a Western blot analysis (performed as described in Example 11 below) of total cell extracts and "depleted lysates", obtained after immunoprecipitation with mabs 179, 183.1 and 183.2 and 182.

In non-stimulated cells (lanes 2, 4, 6, 8 and 10), a band doublet corresponding to pro-caspase-8 isoform $\alpha 1$ and $\alpha 2$ (pro-caspase-8 53/55 kDa) was detected in total cell extracts (lane 2) and in depleted lysates obtained with anti-183 and anti-182 antibodies (lanes 6, 8 and 10) in contrast no pro-caspase-8 was detected in depleted lysates obtained with mAb 179 (lane 4). These results indicate that mAb 179 immunoprecipitates pro-caspase-8.

In stimulated cells the levels of pro-caspase-8 in total cell extract were lower (lane 1). Additional smaller bands corresponding to activated caspase-8 fragments appeared upon activation i.e. a doublet of partially processed caspase-8 corresponding to isoform $\alpha 1$ and $\alpha 2$ (partially processed caspase-8 p 41/43, lacking Sub-2) and a smaller band corresponding to Sub-1 (p 20). Depletion of the minute amounts of pro-caspase-8 and activated caspase-8 fragments by the mabs was tested on lysates of Fas-ligand stimulated cells (FIG. 2 lanes 3, 5, 7, 9 and 11).

It should be noted that depletion of Sub-1 by mAb 182, specific to Sub-2, was also tested since activated caspase-8 comprises Sub-1 bound to Sub-2 and therefore removal of Sub-2 by immunoprecipitation with mAb 182 should consequently lead to depletion of Sub-1.

Immunoprecipitation of caspase-8 from stimulated cell lysates show that mAbs 182, 183.1 and 183.2, similar to the normal mouse serum control (FIG. 2 lane 11), did not remove the small amounts of remaining pro-caspase-8 or the active caspase-8 fragments (lanes 9, 7, 5 and 11 respectively). In contrast to these results, treatment of the cell lysates with mAb 179 (lane 3), efficiently removed all the pro-caspase-8, as well as the active caspase-8 fragments.

FIGS. 3a (Western blot analysis) and 3b (protein detection by Silver staining) show that immunoprecipitated pro-caspase-8 and active caspase-8 fragments by mAbs 179, 182 and 183.1 and 183.2 antibodies could be efficiently recovered into the supernatant by competition with the respective peptides against which the various antibodies were been raised (Example 13).

In non-stimulated cells (FIG. 3a, lanes 2, 4, 6, 8 and 10 and FIG. 3b, lanes 2, 3, 6, 8, and 10), pro-caspase-8 is efficiently recovered by immunoprecipitation with mAb 179 and competition with peptide 179 (FIGS. 3a and 3b, lane 8). In stimulated cells, in spite of the small amount of pro-caspase-8 left after activation, immunoprecipitation with mAb 179 resulted in effective recovery of the protein (FIGS. 3a and 3b, lane 9). Some recovery of pro-caspase-8 could be observed in non activated cells by mAb 183.2 (FIG. 3a, lane 6) and in activated cells by mAb 183.1 (FIG. 3a, lane 5) where active fragments of caspase-8 could be recovered in lysates of activated cells by mAbs 182 (FIG. 3a, lane 3), 183.1 (FIG. 3a, lane 5) and 183.2 (FIG. 3a, lane 7, only p20).

The results obtained indicated that the mAb 179 developed against the peptide corresponding to the C-terminus of Sub-1 (179 epitope) is very efficient for immunoprecipitation and purification of pro-caspase-8, even present in trace amounts, as well as for activated caspase-8.

Polyclonal antibody specific to the same 179 epitope (prepared as described in Example 1 above) was generated to investigate whether the 179 epitope has the unique capability of eliciting antibodies, which can be generally used for the efficient immunoprecipitation and purification of pro-caspase-8 and active caspase-8. The "depleted lysates" obtained by immunoprecipitation with polyclonal antibody specific to epitope 179 (lanes 5 and 6 for activated and non-activated cells, respectively) or by monoclonal antibody specific to epitope 182 (lanes 7 and 8 for activated and non-activated cells, respectively) were compared. The results in FIG. 4 clearly show that indeed, pro-caspase-8 and caspase-8 fragments from stimulated cell lysates are also efficiently removed from the cell lysate with polyclonal anti 179 antibodies and even more efficient than with monoclonal anti182 antibody.

In parallel immunoprecipitation and recovery of pro-caspase-8 from resting cells lysates carried out with mAb 183 and polyclonal antibody specific to the 183 epitope (described in Example 1) were compared to those obtained with mAb 179. FIG. 5 shows that immunoprecipitation of pro-caspase-8 by mAb 183 and poly 183 is ineffective while immunoprecipitation of pro-caspase-8 by mAb 179 is remarkably superior.

An additional caspase-8 derived fragment of about 5.6 kDa is observed only in immunoprecipitates carried with mAb 179 (lane 3). Antibodies developed against the region of caspase-8 that corresponds to the C-terminus of the large caspase Sub-1 have a unique ability to impose on the caspase a novel mode of processing.

The results observed above indicate that epitope 179 of caspase-8, unlike other epitopes, has the special capability of eliciting specific antibodies that are very efficient for immunoprecipitation of pro-caspase-8 and activated caspase-8 and are able to induce pro-caspase-8 autoprocessing.

Example 6

Isolation and Identification of a Caspase-8 Binding Polypeptide (Cari)

Due to its capability to efficiently immunoprecipitate caspase-8, mAb 179 was exploited to co-immunoprecipitate caspase-8 and caspase-8-bound proteins.

BJAB cells (Steinitz et al, 1975) were stimulated with Fas-ligand for one hour and cell lysates were prepared from cells before and after stimulation. Following immunoprecipitation and elution, as described in Example 13, the recovered proteins were resolved by SDS-PAGE and detected by Silver-staining. Immunoprecipitation with mouse IgG1 served as the negative control. The results in FIG. 6 show that a polypeptide of an apparent molecular weight of about 72.5 kDa (herein called p72) is co-precipitated with pro-caspase-8 (p 53/55) in lysates from resting cells (lane 3), but not with active caspase-8 in lysates from stimulated cells (lane 4).

In addition, a p72 polypeptide was found to co-immunoprecipitate with pro-casapse-8 also in lysates prepared from non-stimulated HeLa, Raji, H9, K562, HL-60, CEM and Hut78 cells (ATCC).

These results suggest that a polypeptide, p72, is generally bound to pro-caspase-8 but not to active caspase-8.

The band in the SDS-PAGE corresponding to p72 was excised, trypsin digested and subject to limited sequence analysis and to mass spectroscopy analysis. Seven peptides obtained by trypsin digestion were used to search a protein database deduced from nucleotide sequences (or ESTs). The protein sequence matched part of a predicted protein sequence of a human EST clone (SEQ ID NO:1) found in the gene bank (accession number gi/2988397/gbAAC08052.1/ (AC004475) whose function was unknown.

Example 7

Generation of the Full-Length cDNA Encoding p72

The full-length cDNA encoding p72 was generated as follows:

The EST from (Example 6) was used to screen a TIGR Human gene index and the THC report (THC510568 SEQ ID NO:1) containing the consensus of all the ESTs that fit this sequence was obtained.

A DNA clone encoding part of the predicted polypeptide was purchased from Incyte Genomics (IMAGE #2964545). The clone lacked the nucleotide sequences encoding the first methionine and the 6 succeeding amino acids (i.e., 21 nucleotides). The mouse and human sequences of these proteins were found to be highly similar (about 90% identity), thus the nucleotide sequences encoding the first methionine and the 6 succeeding amino acids of the mouse protein which were not missing in the mouse ESTs were compared to the working draft sequence of the human genome in order to complete the missing human sequence. A hit was obtained corresponding to the sequence of *Homo sapiens* chromosome 19, clone LLNLR-232E12. This clone confirmed the nucleotide sequence, which encodes the missing 7 amino acids of p72. The full-length cDNA of p72 was obtained by two PCR rounds (Takara ExTaq, Takara, cat # R001A was used), which are schematically represented in FIG. 8.

In the first PCR the clone obtained from Incyte Genomics was used as the template with the forward primer: CTCAAGATGGACAACCGGGATGTTGCAGGAAAGG (SEQ ID NO:11) synthesized to contain 15 (underlined) out of the 21 missing nucleotides together with the existent sequence of p72 (FIG. 8, primer 2), and the reverse primer: CCACTCGAGTCAGTAGTAAGGCCGTCTGGGATT (SEQ ID NO:12) containing the 3' region ending with the stop codon (FIG. 8, primer 3).

The second PCR comprises as the template the PCR product of the first PCR round and the forward primer: AATGGATCCATGAGTCTCAAGATGGACAACCGGGA (SEQ ID NO:13) containing the whole 21 missing nucleotides and 5 existent nucleotides (FIG. 8, primer 1) and the same reverse primer (FIG. 8, primer 3). The whole cDNA encoding p72 was recovered and sequenced (SEQ ID NO:2), and the amino acid sequence was predicted from the nucleotide sequence (SEQ ID NO:3).

Comparison of the sequence obtained in the THC report (THC510568 SEQ ID NO:1) containing the consensus of all the ESTs, and the polypeptide predicted by the generated full length cDNA (SEQ ID NO:3) in FIG. 13 shows the missing 7 first amino acids in the ESTs the missing 25 amino acids sequence in the ESTs and inaccuracy of amino acid 397 (proline instead of leucine).

P72 polypeptide was found to contain three conserved motifs (FIG. 7): the C motif a coiled motif, two tandem located 'SURP' (also called 'SWAP' motifs, denoted as S FIG. 7) (Denhez and Lafyatis, 1994) close to the N terminus of the polypeptide, and one C terminally located 'G-patch' (FIG. 7 denoted as G) (Aravind and Koonin, 1999). Both the SURP and the G-patch motifs are believed to contribute to RNA-binding, suggesting that the target of p72 may be a RNA molecule. Thus p72 was renamed to Cari (Caspase-8 Associated polypeptide with RNA binding motifs)

Example 8

Cleavage of Cari by Caspase-8

As shown in Example 6, Cari is bound only to pro-caspase-8 and not to active caspase-8 as tested one hour after stimulation. Some pro-caspase-8 can be still detected after 20 minutes stimulation. To determine whether Cari can be co-precipitated with pro-caspase-8 at shorter stimulation times, BJAB cells activated for only 20 minutes were lysed and immunoprecipitated with mAb 179. Following immunoprecipitation and elution, caspase-8 and bound polypeptides were resolved by SDS-PAGE and the polypeptides were detected by Silver staining. One band of 72.5 kDa (FIG. 9, lane 3) probably corresponding to Cari was immunoprecipitated in lysates from cells before stimulation while after 20 minutes stimulation, in addition to Cari, a polypeptide with a lower apparent molecular weight of about 68 kDa was detected (FIG. 9, lane 4). Both polypeptides, the 72.5 and 68 kDa, immunoprecipitated from BJAB cells, were subjected to mass spectroscopy analysis. After tripsynization, both polypeptides exhibited similar peptide profile except one clear difference, an additional peptide of sequence FRPNPLNNPR (residues 632-641 of SEQ ID NO:3) was present in the 72.5 kDa (Cari) at the C-terminus but absent in the 68 kDa polypeptide.

This result suggests that upon cell stimulation a fragment of about 4.5 kDa is removed from the C-terminus of Cari, probably by activated caspase-8, resulting in a smaller polypeptide with an apparent molecular weight of 68 kDa, which is still bound to the remaining pro-caspase-8.

It is conceivable that residue D 600 located at the C-terminus of Cari (FIG. 7) could be a candidate residue for cleavage, because the putative fragments resulting from such a cleavage exhibit similar molecular weight as the Cari fragments detected in vivo following 20 minutes stimulation.

In order to test whether, as suggested, Cari is a substrate of caspase-8 and D 600 is the target residue for cleavage, an in vitro transcripted-translated and radioisotope labeled ($S^{35}$) Cari (TnT system) was subjected to the action of recombinant active caspase-8. Cari cDNA was expressed in vitro in reticulocyte lysates in the presence of $^{35}S$ methionine using the TnT T7 Coupled Reticulocyte Lysate System, and subjected to cleavage by recombinant active caspase-8 (each Sub-unit 1 and 2 prepared separately in *E. coli* mixed and re-folded together in vitro). Briefly, in-vitro synthesized $^{35}S$ labeled Cari was incubated for 30 min. in protease buffer (25 mM HEPES, pH 7.5, 0.1% CHAPS, 5 mM EDTA and 2 mM DTT) at 37° C. in the presence or the absence of bacterially produced active caspase-8. Proteins and their fragments were separated on SDS-PAGE and the results visualized by phospho-imaging. The results (FIG. 10) show that in the absence of caspase-8 only the 72.5 band corresponding to full length Cari (lane 1) was detected. This band disappears after addition of activated caspase-8 for 1 hour and a new smaller fragment corresponding to 68 kDa appears (lane 4). This result indicates that the protein encoded by the Cari cDNA used as substrate, is effectively cleaved by caspase-8.

In addition, the TnT transcription translation system was used also to produce in vitro two different Cari mutants: (1) Cari in which the residue D 600, suspected from the in vivo experiments to be the target residue for caspase-8, was mutated to E (D600E), and (2) a deleted Cari missing the residues down-stream D600 (i.e., the expressed protein will exhibit the 1-600 residues).

Cleavage of the above two Cari mutants was tested in the presence (FIG. 10, lanes 5 and 6, respectively) or in the absence (lanes 2 and 3, respectively) of active recombinant caspase-8. As shown in FIG. 10 (lanes 3 and 6 respectively), the same protein profile of Cari D600E mutant is observed in the presence or the absence of caspase-8, indicating that caspase-8 does not cleave the Cari D600E mutant. The Cari 1-600 mutant co-migrates with the 68 kDa fragment produced after cleavage of the wild type Cari and is not further cleaved by addition of caspase-8 (lanes 2 and 5). These results show that, upon activation, caspase-8 cleaves Cari at the D600 residue.

Studies carried out in vivo suggest that cleavage of Cari by caspase-8 occurs rapidly in cells, within 5-20 minutes after Fas ligand stimulation (FIG. 11), and that the cleaved Cari (or rather—its larger fragment) may remain associated with pro-caspase-8.

Example 9

Functional Characterization of Cari

To analyze the effect of Cari on apoptotic cell death induced by the TNF receptor signaling pathway, Cari cDNA or antisense Cari (a/s), or a vector without p72 cDNA insert as the negative control was used (pc). The cDNA was inserted into the pcDNA 3.1 expression vector (available from Invitrogen) and co-transfected with p55 TNFR receptor DNA inserted into the pcDNA3 vector (Invitrogen) and with the reporter gene green fluorescence protein (GFP) inserted into the pEGFPC1 expression vector (Clontech), into HEK 293 cells constitutively expressing the T antigen.

After 24 hours the transfected cells were examined under a fluorescent microscope and cell death was scored by determining the number of cells displaying apoptotic morphology out of the total population of fluorescent cells. Overexpression of Cari was found to potentiate the cell death induced by overexpression of the p55 TNF receptor (FIG. 12a, p72). In contrast, when antisense cDNA construct was used for co-transfection (FIG. 12a p72/a/s), the cells were protected from death induced by overexpression of the p55 TNF.

This result indicates that Cari modulates apoptotic cell death induced by the TNF receptor-signaling pathway.

In general, triggering of a receptor like CD120a by FasL requires the addition of a protein synthesis inhibitor like cycloheximide in order to achieve a strong signal for apoptosis. To analyze the effect of Cari on cell death induced by the Fas signaling pathway, the effect of Cari overexpression on Fas ligand mediated cell death, without addition of cycloheximide, was monitored in HEK 293 cells constitutively expressing the T antigen (HEK-293 T). In the experiment, HEK-293 T cells were co transfected with a vector pcDNA3.1 or pcDNA3.1 encoding Cari or Cari antisense (pc, p72 and p72 a/s respectively) and a vector pSBC-2 (Dirks et al, 1983) encoding the reporter gene SEAP (secreted alkaline phosphatase). After 24 hours, the transfected cells were induced with Fas-ligand for 16 hours and the growth medium was replaced with fresh growth medium. Cell death was calculated by determining the amount of SEAP secreted into the growth medium during 24 hours (detected by enzymatic reaction as described by Boldin et al). The results in FIG. 12b indicate that overexpression of Cari, but not Cari antisense, caused death in combination with Fas-ligand stimulation. The results show also that overexpression of Cari in the absence of Fas-ligand stimulation does not have any effect on cell death (not shown).

The effect of pSuper-Cari overexpression, a system for stable expression of short interfering Cari RNAs, which supposedly will blockage Cari, was tested on apoptosis induced in HeLa cells by overexpression of Mach a1 (caspase-8) or by a chimera comprising the extracellular part of p55 TNFR1 fused to the transmembrane and intracellular part of FAS receptor (CI*).

HeLa cells ($2 \times 10^5$ cells) were seeded and cotransfected using 2 μg Mach a1 or CI* DNA containing plasmid (backbone plasmid, pcDNA3 from Invitrogen) and 3 μg psuper vector (Brummelkamp et al, 2002) or pSuper-Cari (pSuper-Cari is a 1:1 mix of psuper plasmids containing sequences derived from human Cari cDNA's AAGAGGATAAGGTAGAGCTCC (1169-1190 SEQ ID NO:6) or from 3'-non-translated region AATGACCAACCGTCCCTGGAC (3' 26-47 bp SEQ ID NO:7) and 0.5 μg reporter GFP gene containing plasmid (backbone plasmid, pRGFP Clontech). 27 hours post transfection, the cells were examined under a fluorescent microscope and cell death was estimated by the morphology of the GFP containing cells.

The results are summarized in FIG. 16. While death of cells is induced by overexpressing Mach a1 or CI* (apoptosis is more elevated in Mach a1 than in CL* overexpressing cells), cells transfected with pSuper-Cari together with Mach a1 or Cl* show significantly reduced or no apoptosis. These results demonstrate that induction of apoptosis through the TNF receptor signaling pathway or by caspase-8 requires the activity of Cari.

Example 10

Western Blot Analysis for Detection of Caspase-8 Immunoreactive Serum

A mixture of recombinant purified Sub-1 and Sub-2 was used for Western blot analysis of antibodies developed to synthetic peptides. Briefly a 12% SDS Poly Acryl amide gel was loaded with 100 ng/lane of a mixture of Sub-1 and Sub-2 under reducing conditions (40 mM DTT). One lane was loaded with Low Molecular Weight Markers (LMW). The proteins separated on the gels were transferred by electro elution to PVDF high bond-P (Amersham) membranes. The membranes were incubated in PBS containing 5% low-fat milk, 0.05% Tween 20, for 16 hours. The membranes were cut into strips and each strip was incubated for 1 hour at room temperature with the mouse antiserum (diluted 1/2000). Membrane strips were washed with PBS containing 0.05% Tween 20 (3×15 min) and incubated for one hour with the second antibody—goat anti-mouse conjugated to horseradish peroxidase (diluted 1:10.000, Jakson) for 1 hour at room temperature.

The strips were washed with PBS containing 0.1% Tween 20 (3×15 min). The positive bands were detected by enhanced chemiluminescence (ECL, Amersham).

For Western blots performed in Example 5 antibodies specific to Sub-1 were used (Cell Signaling Technology Caspase-8 ICI2 Cat 9746).

Example 11

ELISA for Hybridoma Clones Screening

The direct ELISA for screening hybridoma producing specific antibody was performed as following: 96 wells plates were coated with 50 µl/well of BSA-peptide (or BSA alone for control plates) at a concentration of 2.5 µg/ml in binding solution (0.1 M $Na_2HPO_4$, pH 9) for 1 hour at 37° C. or 16 hours at 4° C. Subsequently the plates were washed 3 times with PBS-T (PBS with 0.05% of Tween-20) and loaded with 200 µl/well of blocking solution (1% hemoglobin in PBS) for 1 hour at 37° C. and washed 3 times with PBS. 50 µl of hybridoma culture supernatant or diluted standards (with PBS-T) were loaded per well and incubated for 1 hour at 37° C. or 4 hours at 22° C. After this incubation period the wells were washed 6 times with PBS-T. A second antibody, anti mouse antibody conjugated to HRP (Jackson 115-025-100) was diluted 1:5000 in PBS-T, incubated for 1 hour at 37° C. and washed away by washing 6 times with PBS-T. The substrate for HRP was freshly prepared (2.2 ml of 0.2M $Na_2HPO_4$, pH 9.2, 1.4 ml of 0.2 M citric acid, pH 4.35, 6.4 ml $H_2O$, 10 mg ABTS and 1 µl $H_2O_2$) and 50 µl/well were loaded and incubated at 22° C. until color developed (about 5-80 minutes). The color reaction was stopped by adding 50 µl/well 0.2 M citric acid. The plates were read at 405 nm.

As a positive control antibody, positive mouse antiserum diluted 1:1000 was used and as negative control media.

Example 12

Immunoprecipitation of Caspase-8

For every immunoprecipitation $10^8$ cells were used. Cells were collected and lysed by incubation in 1% NP-40 lysis buffer and complete protease inhibitor (complete protease inhibitor cocktail tablets from Roche Molecular Biochemicals) on 0° C. for 40 min. The cell lysates were aliquoted in Eppendorf tubes, centrifuged at 14000 rpm for 10 minutes at 4° C. and the supernatant collected in a new tube. The cell lysates were subjected to a pre-clearing step, intended to remove proteins that bind non-specifically to the protein-G-sepharose. For pre-clearing, cell lysate was pre-incubated with PBS pre-washed protein-G-sepharose (Pharmacia) and with mouse IgG for 2-3 hours at 4° C. Following this incubation the lysates were centrifuged in Eppendorf tubes for 14000 rpm for 30 seconds, the protein G-sepharose was discarded and the pre-cleared supernatant collected. Purified monoclonal antibody (or mouse IgG 1 kappa for negative controls) and PBS pre-washed protein-G-sepharose were mixed and incubated with the pre-cleared supernatant for 4- to 16 hours at 4° C. Following this incubation period the unbound material denoted "depleted lysate" was collected by centrifugation (30 seconds at 14000 rpm) and the bound material was eluted by washing the sepharose beads 6 times with lysis buffer and by incubation with an "eluting solution" containing 0.2% NP-40 lysis buffer, protease inhibitors and 400 µg/ml peptide used for immunization (300 µl eluting solution/100 µl sepharose) for 2 hours at 22° C. The tubes were spun for 5 minutes at 5,000 rpm and the supernatant denoted "caspase-8 eluate" transferred into a new tube.

Example 13

Assessment of the Effect of the Non-Cleavable Mutant p72 D600E in Fas-Mediated Apoptosis Cari was found to be cleaved by active caspase-8 and the specific cleavage site was demonstrated by generating a non-cleavable mutant (p72 D600E) (Example 8). Transient overexpression of Cari was shown to potentiate the apoptotic activity of Fas ligand-treated cells (Example 8). To assess the effect of the non-cleavable mutant p72 D600E over the wild type polypeptide in Fas mediated apoptosis, BJAB cells were genetically engineered to produce constitutively either the mutant or the wild type Cari and the effect of Fas ligand in the engineered cells was monitored. To generate the constitutive production, the cDNAs encoding each of the two Cari proteins were inserted in the pcDNA 3.1 expression vector. Transfectant BJAB cells were selected in 1500 µg/ml neomycin and isolates were collected and tested for Cari production by Western blot analysis of the cell lysates. Isolates producing similar levels of Cari wild type and mutant were further selected. The survival of BJAB cells was monitored after Fas ligand application to control cells (B1), cells constitutively expressing transfected p72 (B2) and cells constitutively expressing transfected D600E p72 (B3). The results in FIG. 14 show that the cells expressing the non-cleavable Cari mutant are more efficiently killed by Fas ligand treatment than those expressing the wild type Cari. One possible explanation for this result is that Cari might be involved in the conversion of pro-caspase-8 into active caspase-8. Therefore a non-cleavable Cari will continuously induce conversion of pro-caspase-8 into active caspase-8 resulting increase of apoptosis, unlike the wild type p72, which will be cleaved and probably inactivated by active caspase-8.

To test the possible involvement of Cari in the activation of caspase-8, the rate of pro caspase-8 conversion into active caspase-8 upon Fas ligand treatment in BJAB cells expressing wild type Cari or the uncleavable Cari mutant were monitored by western blot analysis with anti-caspase-8 specific antibodies for the detection of pro-caspase-8 and activated caspase-8. The results obtained indicated that the rate of caspase-8 activation is higher in BJAB cells producing the mutant Cari (not shown).

These results suggest that p72 is involved in activation of caspase-8 and that the increase in anti-apoptotic activity mediated by Fas ligand obtained with cells expressing the mutant p72 D600E over the wild type protein is due to the fact that the former protein remains active (is not cleaved) in spite of the presence of active caspase-8.

Example 14

Determination of the Domain in Cari Responsible for Binding Caspase-8

Deletion studies were carried out with Cari to determine the minimal amino acid sequence in Cari responsible for binding caspase-8. Cari was progressively deleted and the resulting fragment was ligated to a GFP reporter gene and introduced into pcDNA3.1/HisC vector (Invitrogen). The Cari constructs (10 µg) were co-transfected into HeLa cell together with a vector (10 µg) containing pro-caspase-8 (Mach a1 (C360S) introduced in pcDNA 3 vector (Invitrogen).

24 hours post transfection, the cells were lysed in 1% NP-40 lysis buffer. Caspase-8 was immunoprecipitated with antibody 179 and protein G for two hours. The precipitated complex was washed 5 times with washing buffer (0.2% NP-40 buffer) and eluted in washing buffer containing peptide 179. The immunoprecipitated proteins were resolved by SDS-PAGE and subjected to Western blot analysis using anti caspase-8 antibody 1C12 (1:2000, Cell Signaling Technology) and polyclonal antibody against *E. coli* produced His-Cari (1:2000).

FIG. 7 shows the schematic representation of Cari including the Coiled-coil motif, SURP-or SWAP motif, G-patch motif, the NLS motifs, the caspase-8 cleavage site D600 and the corresponding amino acid spanning the above motifs. Table II summarizes the results of binding of Cari full and deleted construct to caspase-8.

D600, the cleavage site of caspase-8 in Cari is probably not required for its binding since the D600E Cari mutant does bind caspase-8. The deletion construct 393-645 which lacks part of the N-terminal of the protein including some of the above Cari motifs (Coiled-coil motif, SURP-or SWAP motif, G-patch motif, the NLS motifs) but contains the intact C terminus of the protein still binds caspase-8, indicating that unlike the C terminus end, those motifs are not required for binding caspase-8. The G-patch motif is probably not necessary as well, as demonstrated with the deletion construct 393-437 which lacks the G-patch motif and still binds to the caspase. The protein could be further deleted from its N-terminal end to get a 24 amino acid peptide SVQDLKGLGYEKGKPVGLVGVTEL (construct 414-437) (SEQ ID NO:4), which still binds to caspase-8. Additional deletion of 16 amino acids to such peptide, from the N terminal end, resulted in a 9 amino acid peptide (construct 429-437) that failed to bind caspase-8. Thus, a deletion of only 7 amino acids from the N terminal of the 414-437 construct, resulting in a 16 amino acid peptide (construct 422-437), was tested and was found to bind to caspase-8. Thus, the smallest amino acid able to bind caspase-8 was found to be a 16 amino acid peptide of sequence GYEKGKPVGLVGVTEL (construct 422-437) (SEQ ID NO:5; FIG. 15).

TABLE II

| Cari Construct | Binding to Caspase-8 | Comment |
| --- | --- | --- |
| Full length Cari (1-645) | + | |
| Mutant D600E (1-645) | + | Non-cleavable at residue 600 |
| 1-260 | − | N-terminal end including only the first SURP module |
| 1-330 | − | N-terminal end including two SURP modules |
| 1-352 | − | N-terminal end including two SURP modules and the first NLS |
| 1-427 | − | N-terminal end including two SURP modules and the first NLSs |
| 1-490 | + | N-terminal end including two SURP modules and all 3 NLSs |
| 1-531 | + | N-terminal end including two SURP modules and all 3 NLSs |
| 179-645 | + | Including two SURP modules and the C-terminal end |
| 260-645 | + | Including only the second SURP module and the C-terminal end |
| 370-645 | + | Including only two NLSs and the C-terminal end |
| 370-645 with mut NLS | + | Similar to 370-645 mutant but with the NLS sequence mutated |
| 393-645 | + | Comprising the C-terminal end without any NLS |
| 370-484 | + | Containing NLS and part of the C-terminal end excluding the G-patch motive |
| 370-484 with mut NLS | + | Similar to 370-484 mutant but with the NLS sequence mutated |
| 438-484 | − | GFP-fusion to C-terminal end |
| 393-437 | + | GFP-fusion to C-terminal end |
| 398-437 | + | GFP-fusion to C-terminal end |
| 406-437 | + | GFP-fusion to C-terminal end |
| 414-437 | + | GFP-fusion to C-terminal end |
| 429-437 | − | GFP-fusion to C-terminal end |
| 422-437 | + | GFP-fusion to C-terminal end |

REFERENCES

Adelman et al, "In vitro deletional mutagenesis for bacterial production of the 20,000-dalton form of human pituitary growth hormone", *DNA* 2(3):183-193 (1983)

Ahmad et al, "CRADD, a novel human apoptotic adaptor molecule for caspase-2, and FasL/tumor necrosis factor receptor-interacting protein RIP", *Cancer Res* 57(4):615-619 (1997)

Akagi et al, "Transcriptional activation of a hybrid promoter composed of cytomegalovirus enhancer and beta-actin/beta-globin gene in glomerular epithelial cells in vivo", *Kidney Int* 51(4):1265-1269 (1997)

Aravind et al, "G-patch: a new conserved domain in eukaryotic RNA-processing proteins and type D retroviral polyproteins", *Trends Biochem Sci* 24(9):342-344 (1999)

Ausubel et al, *Current Protocols in Molecular Biology*, Greene Publications and Wiley Interscience, New York, N.Y. (1978-1995, 1999 and 2003)

Beidler et al, "The baculovirus p35 protein inhibits Fas- and tumor necrosis factor-induced apoptosis", *J Biol Chem* 270(28):16526-16528 (1995)

Beutler et al, "Cachectin: more than a tumor necrosis factor", *N Engl J Med* 316(7):379-385 (1987)

Bigda et al, "Dual role of the p75 tumor necrosis factor (TNF) receptor in TNF cytotoxicity", *J Exp Med* 180(2): 445-460 (1994)

Bodanszky and Bodanszky, *The Practice of Peptide Synthesis*, Springer, New York, ISBN 0-387-13471-9 (1984)

Bodanszky, *The Principles of Peptide Synthesis*, Springer, New York, ISBN 0-387-56341-4 (1993).

Boldin et al, "A novel protein that interacts with the death domain of Fas/APO1 contains a sequence motif related to the death domain", *J Biol Chem* 270(14):7795-7798 (1995)

Boldin et al, "Self-association of the "death domains" of the p55 tumor necrosis factor (TNF) receptor and Fas/APO1 prompts signaling for TNF and Fas/APO1 effects", *J Biol Chem* 270(1):387-391 (1995a)

Boldin et al, "A protein related to a proteasomal subunit binds to the intracellular domain of the p55 TNF receptor upstream to its 'death domain'", *FEBS Lett* 367(1):39-44 (1995b)

Boldin et al, "Involvement of MACH, a novel MORT1/FADD-interacting protease, in Fas/APO-1- and TNF receptor-induced cell death", *Cell* 85(6):803-815 (1996)

Boone et al, "Structure/Function analysis of p55 tumor necrosis factor receptor and fas-associated death domain. Effect on necrosis in L929sA cells", *J Biol Chem* 275(48):37596-37603 (2000)

Boulianne et al, "Production of functional chimaeric mouse/human antibody", *Nature* 312(5995):643-646 (1984)

Brakebusch et al, "Cytoplasmic truncation of the p55 tumour necrosis factor (TNF) receptor abolishes signalling, but not induced shedding of the receptor", *EMBO J.* 11(3):943-950 (1992)

Brockhaus et al, "Identification of two types of tumor necrosis factor receptors on human cell lines by monoclonal antibodies", *Proc Natl Acad Sci USA* 87(8):3127-3131 (1990)

Brummelkamp et al, "A system for stable expression of short interfering RNAs in mammalian cells", *Science* 296(5567):550-553 (2002)

Bruggemann et al, "Human antibody production in transgenic mice: expression from 100 kb of the human IgH locus", *Eur J Immunol* 21(5):1323-1326 (1991)

Cabilly et al, "Generation of antibody activity from immunoglobulin polypeptide chains produced in *Escherichia coli*." *Proc Natl Acad Sci USA* 81:3273-3277 (1984)

Cantor et al "Ribozyme cleaves rex/tax mRNA and inhibits bovine leukemia virus expression", *Proc Natl Acad Sci USA* 90(23):10932-10936 (1993)

Cao et al, "Lymphotactin gene-modified bone marrow dendritic cells act as more potent adjuvants for peptide delivery to induce specific antitumor immunity", *J Immunol* 161(11):6238-6244 (1998)

Chen et al, "Inhibition of HIV-1 replication by novel multitarget ribozymes", *Ann NY Acad Sci* 660:271-273 (1992)

Chinnaiyan et al, "FADD, a novel death domain-containing protein, interacts with the death domain of Fas and initiates apoptosis", *Cell* 81(4):505-512 (1995)

Chinnaiyan et al, "FADD/MORT1 is a common mediator of CD95 (Fas/APO-1) and tumor necrosis factor receptor-induced apoptosis", *J Biol Chem* 271(9):4961-4965 (1996)

Clements et al, "Production by EBV infection of an EBNA-positive subline from an EBNA-negative human lymphoma cell line without detectable EBV DNA", *Int J Cancer* 16(1):125-133 (1975)

Cohen G M, "Caspases: the executioners of apoptosis", *Biochem J* 326(Pt 1):1-16 (1997)

Creighton T E, *Proteins: Structure and Molecular Properties*, W.H. Freeman & Co., San Francisco, Calif. (1983)

Daniel et al, "Retroviral transfer of antisense sequences results in reduction of C-Abl and induction of apoptosis in hemopoietic cells", *J Biomed Sci* 5(5):383-394 (1998)

Denhez and Lafyatis, "Conservation of regulated alternative splicing and identification of functional domains in vertebrate homologs to the *Drosophila* splicing regulator, suppressor-of-white-apricot", *J Biol Chem* 269(23):16170-16179 (1994)

Dirks et al, "Dicistronic transcription units for gene expression in mammalian cells", *Gene* 128(2):247-249 (1993)

Duan and Dixit, "RAIDD is a new 'death' adaptor molecule", *Nature* 385(6611):86-89 (1997)

Edamatsu et al, "Inducible high-level expression vector for mammalian cells, pEF-LAC carrying human elongation factor 1alpha promoter and lac operator", *Gene* 187(2):289-294 (1997)

Edinger et al, "Use of GPR1, GPR15, and STRL33 as coreceptors by diverse human immunodeficiency virus type 1 and simian immunodeficiency virus envelope proteins", *Virology* 249(2):367-378 (1998)

Enari et al, "Involvement of an ICE-like protease in Fas-mediated apoptosis", *Nature* 375(6526):78-81 (1995)

Enari et al, "A caspase-activated DNase that degrades DNA during apoptosis, and its inhibitor ICAD", *Nature* 391(6662):43-50 (1998)

Engelmann et al, "Two tumor necrosis factor-binding proteins purified from human urine. Evidence for immunological cross-reactivity with cell surface tumor necrosis factor receptors", *J Biol Chem* 265(3):1531-1536 (1990a)

Engelmann et al, "Antibodies to a soluble form of a tumor necrosis factor (TNF) receptor have TNF-like activity", *J Biol Chem* 265(24):14497-14504 (1990b)

Eshhar Z, in *Hybridoma technology in the bioscience and medicine*, Chapter 1, Edited by Timothy A. Springer (Plenum Publishing Corporation, 1985)

Everett et al, "The repeated GC-rich motifs upstream from the TATA box are important elements of the SV40 early promoter", *Nucleic Acids Res* 11(8):2447-2464 (1983)

Fernandes-Alnemri et al, "In vitro activation of CPP32 and Mch3 by Mch4, a novel human apoptotic cysteine protease containing two FADD-like domains", *Proc Natl Acad Sci USA* 93(15):7464-7469 (1996)

Flanagan W M, "Antisense comes of age", *Cancer Metastasis Rev*, 17(2):169-176 (1998)

Furth et al, "Temporal control of gene expression in transgenic mice by a tetracycline-responsive promoter", *Proc Natl Acad Sci USA* 91(20):9302-9306 (1994)

Gerster et al, "Quantitative analysis of modified antisense oligonucleotides in biological fluids using cationic nanoparticles for solid-phase extraction", *Anal Biochem* 262(2):177-184 (1998)

Graham et al, "Isolation and characterisation of the human lung NK-2 receptor gene using rapid amplification of cDNA ends", *Biochem Biophys Res Commun* 177(1):8-16 (1991)

Grau G E, "Tumor necrosis factor (TNF) and pathology; its relationships with other cytokines", *Schweiz Med Wochenschr* 119(49):1756-1761 (1989)

Griscelli et al, "Heart-specific targeting of beta-galactosidase by the ventricle-specific cardiac myosin light chain 2 promoter using adenovirus vectors", *Hum Gene Ther* 9(13):1919-1928 (1998)

Guang-Lin et al, "Adenovirus-mediated gene transfer of CTLA4IG gene results in prolonged survival of heart allograft", *Transplant Proc* 30(7):2923-2924 (1998)

Guinot and Temsamani, "Antisense oligonucleotides: a new therapeutic approach", *Pathol Biol (Paris)* 46(5):347-354 (1998)

Harlow and Lane, Antibodies: A Laboratory Manual, Cold Spring Harbor Laboratory, Cold Spring Harbor, N.Y., (1988)

Hemmi et al, "The presence of human coxsackievirus and adenovirus receptor is associated with efficient adenovirus-mediated transgene expression in human melanoma cell cultures", *Hum Gene Ther* 9(16):2363-2373 (1998)

Henkart P A, "ICE family proteases: mediators of all apoptotic cell death?", *Immunity* 4(3):195-201 (1996)

Hohmann et al, "Two different cell types have different major receptors for human tumor necrosis factor (TNF alpha)", *J Biol Chem* 264(25):14927-14934 (1989)

Hsu et al, "TRADD-TRAF2 and TRADD-FADD interactions define two distinct TNF receptor 1 signal transduction pathways", *Cell.* 84(2):299-308 (1996)

Huang et al, "Intervening sequences increase efficiency of RNA 3' processing and accumulation of cytoplasmic RNA", *Nucleic Acids Res* 18(4):937-947 (1990)

Innis et al, eds, PCR Protocols: A Guide to Method and Applications, Academic Press (1990)

Itoh et al, "The polypeptide encoded by the cDNA for human cell surface antigen Fas can mediate apoptosis", *Cell.* 66(2):233-243 (1991)

Itoh and Nagata, "A novel protein domain required for apoptosis. Mutational analysis of human Fas antigen", *J Biol Chem* 268(15):10932-10937 (1993)

Janmey et al, "Modulation of gelsolin function by phosphatidylinositol 4,5-bisphosphate", *Nature* 325(6102):362-364 (1987)

Joseph and Burke, "Optimization of an anti-HIV hairpin ribozyme by in vitro selection", *J Biol Chem* 268(33): 24515-24518 (1993)

Kischkel et al, "Cytotoxicity-dependent APO-1 (Fas/CD95)-associated proteins form a death-inducing signaling complex (DISC) with the receptor", *EMBO J* 14(22):5579-5588 (1995)

Kohler and Milstein, "Continuous cultures of fused cells secreting antibody of predefined specificity", *Nature* 256 (5517):495-497 (1975)

Kondo et al, "Modulation of apoptosis by endogenous Bcl-xL expression in MKN-45 human gastric cancer cells", *Oncogene* 17(20):2585-2591 (1998)

Kothakota et al, "Caspase-3-generated fragment of gelsolin: effector of morphological change in apoptosis", *Science* 278(5336):294-298 (1997)

Kozak M, "Compilation and analysis of sequences upstream from the translational start site in eukaryotic mRNAs", *Nucleic Acids Res* 12(2):857-872 (1984)

Kumar S, "ICE-like proteases in apoptosis", *Trends Biochem Sci* 20(5):198-202 (1995)

Kumar et al, "Antisense RNA: function and fate of duplex RNA in cells of higher eukaryotes. *Microbiol Mol Biol Rev* 62(4):1415-1434 (1998)

Kunstle et al, "ICE-protease inhibitors block murine liver injury and apoptosis caused by CD95 or by TNF-alpha", *Immunol Lett* 55(1):5-10 (1997)

Kurth and Bryan, "Platelet activation induces the formation of a stable gelsolin-actin complex from monomeric gelsolin", *J Biol Chem* 259(12):7473-7479 (1984)

Lehninger, Biochemistry, Chapter 4, Worth Publishing, NY (1979)

Loetscher et al, "Purification and partial amino acid sequence analysis of two distinct tumor necrosis factor receptors from HL60 cells", *J Biol Chem* 265(33):20131-20138 (1990)

MacFarlane et al, "Identification and molecular cloning of two novel receptors for the cytotoxic ligand TRAIL", *J Biol Chem* 272(41):25417-25420 (1997)

Meinkoth et al, "Hybridization of nucleic acids immobilized on solid supports", *Anal Biochem* 138:267-284 (1984)

Meiri et al, "Memory and long-term potentiation (LTP) dissociated: normal spatial memory despite CA1 LTP elimination with Kv1.4 antisense", *Proc Natl Acad Sci USA* 95(25):15037-15042 (1998)

Mendez et al, "Functional transplant of megabase human immunoglobulin loci recapitulates human antibody response in mice", *Nat Genet* 15(2):146-156 (1997)

Messing et al, Third Cleveland Symposium on Macromolecules and Recombinant DNA, Editor A. Walton, Elsevier, Amsterdam (1981)

Mittl, "Structure of recombinant human CPP32 in complex with the tetrapeptide acetyl-Asp-Val-Ala-Asp fluoromethyl ketone", *J Biol Chem* 272(10):6539-6547 (1997)

Morrison et al, "Chimeric human antibody molecules: mouse antigen-binding domains with human constant region domains". *Proc Natl Acad Sci USA* 81:6851-6855 (1984)

Muranishi et al., "Lipophilic peptides: synthesis of lauroyl thyrotropin-releasing hormone and its biological activity", *Pharm Research* 8:649-652 (1991)

Muzio et al, "FLICE, a novel FADD-homologous ICE/CED-3-like protease, is recruited to the CD95 (Fas/APO-1) death—inducing signaling complex", *Cell* 85(6):817-827 (1996)

Muzio et al "An induced proximity model for caspase-8 activation", *J Biol Chem* 273(5):2926-2930 (1998)

Nagata and Goldstein "The Fas death factor", *Science.* 267(5203):1449-1456 (1995)

Nagata S, "Apoptosis by death factor", *Cell* 88(3):355-365 (1997)

Narumi et al, "SAF-B protein couples transcription and pre-mRNA splicing to SAR/MAR elements", *Nucleic Acids Res* 26(15):3542-3549 (1998)

Nicholson and Thornberry, "Caspases: killer proteases", *Trends Biochem Sci* 22:299-306 (1997)

Nishida et al, "Adenovirus-mediated gene transfer to nucleus pulposus cells. Implications for the treatment of intervertebral disc degeneration", *Spine* 23:2437-2442, (1998)

Nophar et al, "Soluble forms of tumor necrosis factor receptors (TNF-Rs). The cDNA for the type I TNF-R, cloned using amino acid sequence data of its soluble form, encodes both the cell surface and a soluble form of the receptor", *EMBO J.* 9(10):3269-3278 (1990)

Ohtsu et al, "Inhibition of apoptosis by the actin-regulatory protein gelsolin", *EMBO J.* 16(15):4650-4656 (1997)

Pederson et al, "Combined cytosine deaminase expression, 5-fluorocytosine exposure, and radiotherapy increases cytotoxicity to cholangiocarcinoma cells", *J Gastrointest Surg* 2:283-291 (1998)

Peng et al, "Molecular ordering of the Fas-apoptotic pathway: the Fas/APO-1 protease Mch5 is a CrmA-inhibitable protease that activates multiple Ced-3/ICE-like cysteine proteases", *Antisense Nucleic Acid Drug Dev* 11(1):15-27 (2001)

Rotonda et al, "The three-dimensional structure of apopain/CPP32, a key mediator of apoptosis", *Nat Struct Biol* 3(7):619-625 (1996)

Ruzicka et al, Immuno-PCR with a commercially available avidin system" *Science* 260(5108):698-699 (1993)

Sakahira et al, "Cleavage of CAD inhibitor in CAD activation and DNA degradation during apoptosis", *Nature* 391(6662):96-99 (1998)

Salvesen and Dixit, "Caspases: intracellular signaling by proteolysis", *Cell* 91(4):443-446 (1997)

Sambrook et al (Eds), *Molecular Cloning: A Laboratory Manual*, second edition, Cold Spring Harbor Laboratory Press, Cold Spring Harbor, (NY, 1989)

Sano et al, "A streptavidin-protein A chimera that allows one-step production of a variety of specific antibody conjugates", *Biotechnology (NY)* 9(12):1378-1381 (1991)

Sano et al, Immuno-PCR: very sensitive antigen detection by means of specific antibody-DNA conjugates", *Science* 258(5079):120-122 (1992)

Schall et al, "Molecular cloning and expression of a receptor for human tumor necrosis factor", *Cell* 61(2):361-370 (1990)

Schek et al, "Definition of the upstream efficiency element of the simian virus 40 late polyadenylation signal by using in vitro analyses", *Mol Cell Biol* 12(12):5386-5393 (1992)

Schulz et al, *Principles of Protein Structure*, Springer-Verlag, New York, N.Y. (1979)

Schwarzenberger et al, "IL-17 stimulates granulopoiesis in mice: use of an alternate, novel gene therapy-derived method for in vivo evaluation of cytokines", *J Immunol* 161:6383-6389 (1998)

Shevchenko et al, "Rapid 'de novo' peptide sequencing by a combination of nanoelectrospray, isotopic labeling and a quadrupole/time-of-flight mass spectrometer", *Rapid Commun Mass Spectrom* 11(9):1015-1024 (1997)

Shimayama et al, "Cleavage of the highly conserved hairpin-loop region of HIV-1 by synthetic ribozymes", *Nucleic Acids Symp Ser* 29:177-178 (1993)

Shoji et al, "Enhancement of anti-herpetic activity of antisense phosphorothioate oligonucleotides 5' end modified with geraniol", *J Drug Target* 5:261-273 (1998)

Shore et al, "Ribozyme-mediated cleavage of the BCRABL oncogene transcript: in vitro cleavage of RNA and in vivo loss of P210 protein-kinase activity", *Oncogene* 8:3183-3188 (1993)

Smith et al, "Tumor necrosis factor-alpha plays a role in host defense against Histoplasma capsulatum", *J Infect Dis* 162(6):1373-8 (1990)

Soukchareun et al, "Use of Nalpha-Fmoc-cysteine(S-thiobutyl) derivatized oligodeoxynucleotides for the preparation of oligodeoxynucleotide-peptide hybrid molecules", *Bioconjug. Chem* 9(4):466-475 (1998)

Srinivasula et al, "Molecular ordering of the Fas-apoptotic pathway: the Fas/APO-1 protease Mch5 is a CrmA-inhibitable protease that activates multiple Ced-3/ICE-like cysteine proteases", *Proc Natl Acad Sci USA* 93(25):14486-14491 (1996)

Srinivasula et al, "Generation of constitutively active recombinant caspases-3 and -6 by rearrangement of their subunits", *J Biol Chem* 273(17):10107-10111 (1998)

Stanger et al, "RIP: a novel protein containing a death domain that interacts with Fas/APO-1 (CD95) in yeast and causes cell death", *Cell* 81(4):513-523 (1995)

Steinitz et al, "Comparison between growth characteristics of an Epstein—Barr virus (EBV)-genome-negative lymphoma line and its EBV-converted subline in vitro", *Proc Natl Acad Sci USA* 72(9):3518-3520 (1975)

Stix G, "Shutting down a gene. Antisense drug wins approval", *Sci Am* 279(5):46, 50 (1998)

Surinya et al, "Identification and characterization of a conserved erythroid-specific enhancer located in intron 8 of the human 5-aminolevulinate synthase 2 gene", *J Biol Chem* 273(27):16798-16809 (1998)

Tartaglia et al, "A novel domain within the 55 kd TNF receptor signals cell death", *Cell* September 10;74(5):845-853 (1993)

Teoh et al, "Adenovirus vector-based purging of multiple myeloma cells", *Blood,* 92:4591-4601 (1998)

Tewari et al, "Yama/CPP32 beta, a mammalian homolog of CED-3, is a CrmA-inhibitable protease that cleaves the death substrate poly(ADP-ribose) polymerase", *Cell* 81(5):801-809 (1995)

Tokushige et al, "Comparison between cytomegalovirus promoter and elongation factor-1 alpha promoter-driven constructs in the establishment of cell lines expressing hepatitis C virus core protein", *J Virol Methods* 64(1):73-80 (1997)

Tomizuka et al, "Double trans-chromosomic mice: maintenance of two individual human chromosome fragments containing Ig heavy and kappa loci and expression of fully human antibodies", *Proc Natl Acad Sci USA* 97(2):722-7 (2000)

Tracey et al, "Tumor necrosis factor: a pleiotropic cytokine and therapeutic target", *Ann Rev Med* 45:491-503 (1994)

Vandenabeele et al, "Both TNF receptors are required for TNF-mediated induction of apoptosis in PC60 cells", *J Immunol* 154(6):2904-2913 (1995)

Vieira et al, "Production of single-stranded plasmid DNA", *Methods Enzymol* 153:3-11 (1987)

Vercammen et al, "Inhibition of caspases increases the sensitivity of L929 cells to necrosis mediated by tumor necrosis factor", *J Exp Med* 187(9):1477-1485 (1998)

Villa et al, "Caspases and caspase inhibitors", *Trends Biochem Sci* 22(10):388-393 (1997)

Vincenz and Dixit, "Fas-associated death domain protein interleukin-1beta-converting enzyme 2 (FLICE2), an ICE/Ced-3 homologue, is proximally involved in CD95- and p55-mediated death signaling", *J Biol Chem* 272(10):6578-6583 (1997)

Wahl et al, "Improved radioimaging and tumor localization with monoclonal F(ab') 2", *J Nucl Med* 24(4):316-325 (1983)

Wallach D, in *Interferon* 7 (Ion Gresser, ed.), pp. 83-122, Academic Press, London (1986)

Wallach et al, "Tumor necrosis factor receptor and Fas signaling mechanisms", *Annu Rev Immunol* 17:331-367 (1999)

Wang J, "Cyclic peptides incorporating 4-carboxyphenylalanine and phosphotyrosine are potent inhibitors of pp60 (c-) (src)", *J Controlled Release* 53:39-48 (1998)

Watanabe-Fukunaga et al, "Lymphoproliferation disorder in mice explained by defects in Fas antigen that mediates apoptosis" *Nature* 356(6367):314-317 (1992)

Xue et al, "Inhibition of the *Caenorhabditis elegans* cell-death protease CED-3 by a CED-3 cleavage site in baculovirus p35 protein", *Nature* 377(6546):248-251 (1995)

Yang et al, "Autoproteolytic activation of pro-caspases by oligomerization", *Mol Cell* 1(2):319-325 (1998)

Yeh et al, "Inhibition of BMP receptor synthesis by antisense oligonucleotides attenuates OP-1 action in primary cultures of fetal rat calvaria cells", *J Bone Miner Res* 13:1870-1879 (1998)

Yin and Stossel, "Control of cytoplasmic actin gel-sol transformation by gelsolin, a calcium-dependent regulatory protein", *Nature* 281(5732):583-586 (1979)

Yin and Stossel, "Purification and structural properties of gelsolin, a Ca2+-activated regulatory protein of macrophages", *J Biol Chem* 255(19):9490-9493 (1980)

Zacharia et al, "New reduced peptide bond substance P agonists and antagonists: effects on smooth muscle contraction", *Eur J Pharmacol* 203(3):353-357 (1991)

Zhang et al, "Selection of tumor antigens as targets for immune attack using immunohistochemistry: protein antigens", *Clin Cancer Res* 11:2669-2676 (1998)

Zhao and Pick, "Generating loss-of-function phenotypes of the fushi tarazu gene with a targeted ribozyme in *Drosophila*", *Nature* 365(6445):448-451 (1993)

---

The invention claimed is:

1. An isolated polypeptide capable of binding to pro-caspase-8 selected from the group consisting of:
   a) a polypeptide consisting of the amino acid sequence of SEQ ID NO: 3 (Cari);
   b) a variant of Cari (SEQ ID NO: 3) comprising no more than ten amino acid changes and retains the capability of binding to pro-caspase-8;
   c) a fragment of Cari (SEQ ID NO: 3) having the sequence of SEQ ID NO: 5 and includes the pro-caspase-8 binding site; and
   d) a derivative of Cari (SEQ ID NO: 3), which is prepared by modifying the —NH$_2$ group at the N-terminus or the —COOH group at the C-terminus or the functional groups that appear as side chains of one or more amino acids residues of the polypeptides of (a) to (c), without changing one amino acid to another one of the twenty commonly occurring natural amino acids,
without the proviso that said polypeptide is not DF518-3.

2. A polypeptide according to claim 1, being encoded by SEQ ID NO:2.

3. A polypeptide according to claim 1, which is cleaved in vitro by caspase-8.

4. A polypeptide according to claim 1, which is cleaved in vivo by caspase-8.

5. A polypeptide according to claim 1, which is cleaved in vitro or in vivo by caspase-8.

6. A polypeptide according to claim 1, wherein said polypeptide is said fragment of SEQ ID NO:3, or said derivative thereof, having a dominant-negative effect in the activity of the endogenous Cari polypeptide.

7. A polypeptide according to claim 6, capable of inhibiting the apoptotic effect of caspase-8.

8. A polypeptide according to claim 1, wherein said polypeptide is said fragment of SEQ ID NO: 3, or said derivative thereof, capable of inhibiting the interaction of Cari (SEQ ID NO: 3) and a caspase-8.

9. A polypeptide according to claim 8, consisting of the amino acid sequence in SEQ ID NO:4.

10. A polypeptide according to claim 8, consisting of the amino acid sequence in SEQ ID NO:5.

11. A polypeptide according to claim 1, capable of increasing the apoptotic effect of caspase-8.

12. A polypeptide according to claim 11, wherein a variant of Cari (SEQ ID NO: 3) is Cari D600E mutant.

13. An isolated DNA sequence encoding a polypeptide according to claim 1.

14. A DNA sequence according to claim 13, encoding the polypeptide of SEQ ID NO:3.

15. A DNA sequence according to claim 13, consisting of the DNA of SEQ ID NO:2.

16. A DNA sequence according to claim 13, wherein the polypeptide is Cari D600E mutant.

17. A DNA sequence according to claim 13, consisting of the sequence encoding SEQ ID NO:4.

18. A DNA sequence according to claim 13, consisting of the sequence encoding SEQ ID NO:5.

19. A vector comprising a DNA sequence according to claim 13.

20. A vector according to claim 19, wherein the vector is an expression vector.

21. A vector according to claim 19, wherein the vector is a viral vector.

22. A vector having a DNA regulatory sequence functional in cells for enabling endogenous gene activation of an endogenous gene encoding the Cari polypeptide (SEQ ID NO:3), said vector further including targeting sequences corresponding to portions of said endogenous gene such that, after a step of homologous recombination, said regulating sequence will be appropriately targeted to allow said endogenous gene activation.

23. An isolated host cell comprising a vector according to claim 19.

24. A method of producing a polypeptide capable of binding to pro-caspase-8, comprising growing an isolated host cell according to claim 23, and isolating the polypeptide produced.

25. A method according to claim 24, wherein the cell is a eukaryotic cell.

26. A method according to claim 25, wherein the eukaryotic cell is a mammalian, insect, or yeast cell.

27. A method according to claim 26, wherein the cell is selected from HeLa, 293 T HEK and CHO cells.

28. A method according to claim 24, wherein the cell is a prokaryotic cell.

29. A method for down-regulation of a caspase-8, in situations where excessive cell death by apoptosis occurs, comprising causing said caspase-8 to come into contact with a polypeptide according to claim 1, wherein caspase-8 activity is inhibited.

30. The method according to claim 29, wherein said for polypeptide consists of (SEQ ID NO: 4).

31. The method according to claim 29, wherein said polypeptide consists of (SEQ ID NO: 5).

32. The method according to claim 29, wherein the apoptosis is induced by the TNF receptor signaling pathway.

33. A composition comprising a therapeutically effective amount of the polypeptide according to claim 1.

34. A composition according to claim 33, wherein the polypeptide is Cari D600E mutant.

35. A composition according to claim 33, wherein the polypeptide consists of (SEQ ID NO: 4).

36. A composition according to 33, wherein the polypeptide consists of (SEQ ID NO: 5).

\* \* \* \* \*

SEQUENCE LISTING

<160> NUMBER OF SEQ ID NOS: 13

<210> SEQ ID NO 1
<211> LENGTH: 616
<212> TYPE: PRT
<213> ORGANISM: Homo sapiens

<400> SEQUENCE: 1

```
Ala Arg Gly Arg Asp Val Ala Gly Lys Ala Asn Arg Trp Phe Gly Val
1               5                   10                  15

Ala Pro Pro Lys Ser Gly Lys Met Asn Met Asn Ile Leu His Gln Glu
            20                  25                  30

Glu Leu Ile Ala Gln Lys Arg Glu Ile Glu Ala Lys Met Glu Gln
        35                  40                  45

Lys Ala Lys Gln Asn Gln Val Ala Ser Pro Gln Pro Pro His Pro Gly
    50                  55                  60

Glu Ile Thr Asn Ala His Asn Ser Ser Cys Ile Ser Asn Lys Phe Ala
65                  70                  75                  80

Asn Asp Gly Ser Phe Leu Gln Gln Phe Leu Asn Ala Gly Lys Arg Ser
                85                  90                  95

Leu Leu Ile Ser Arg Arg Thr Gly Leu Gly Leu Ala Ser Leu Pro Gly
            100                 105                 110

Pro Val Lys Ser Tyr Ser His Ala Lys Gln Leu Pro Val Ala His Arg
        115                 120                 125

Pro Ser Val Phe Gln Ser Pro Asp Glu Asp Glu Glu Asp Tyr Glu
    130                 135                 140

Gln Trp Leu Glu Ile Lys Val Ser Pro Pro Glu Gly Ala Glu Thr Arg
145                 150                 155                 160

Lys Val Ile Glu Lys Leu Ala Arg Phe Val Ala Glu Gly Gly Pro Glu
                165                 170                 175

Leu Glu Lys Val Ala Met Glu Asp Tyr Lys Asp Asn Pro Ala Phe Ala
            180                 185                 190

Phe Leu His Asp Lys Asn Ser Arg Glu Phe Leu Tyr Tyr Arg Lys Lys
        195                 200                 205

Val Ala Glu Ile Arg Lys Glu Ala Gln Lys Ser Gln Ala Ala Ser Gln
    210                 215                 220

Lys Val Ser Pro Pro Glu Asp Glu Val Lys Asn Leu Ala Glu Lys
225                 230                 235                 240

Leu Ala Arg Phe Ile Ala Asp Gly Gly Pro Glu Val Glu Thr Ile Ala
                245                 250                 255

Leu Gln Asn Asn Arg Glu Asn Gln Ala Phe Ser Phe Leu Tyr Glu Pro
            260                 265                 270

Asn Ser Gln Gly Tyr Lys Tyr Tyr Arg Gln Lys Leu Glu Glu Phe Arg
        275                 280                 285
```

```
Lys Ala Lys Ala Ser Ser Thr Gly Ser Phe Thr Ala Pro Asp Pro Gly
    290                 295                 300

Leu Lys Arg Lys Ser Pro Pro Glu Ala Leu Ser Gly Ser Leu Pro Pro
305                 310                 315                 320

Ala Thr Thr Cys Pro Ala Ser Ser Thr Pro Ala Pro Thr Ile Ile Pro
                325                 330                 335

Ala Pro Ala Ala Pro Gly Lys Pro Ala Ser Ala Ala Thr Val Lys Arg
            340                 345                 350

Lys Arg Lys Ser Arg Trp Gly Pro Glu Glu Asp Lys Val Glu Leu Pro
        355                 360                 365

Pro Ala Glu Leu Val Gln Arg Asp Val Asp Ala Ser Pro Ser Pro Leu
370                 375                 380

Ser Val Gln Asp Leu Lys Gly Leu Gly Tyr Glu Lys Gly Lys Pro Val
385                 390                 395                 400

Gly Leu Val Gly Val Thr Glu Leu Ser Asp Ala Gln Lys Lys Gln Leu
                405                 410                 415

Lys Glu Gln Gln Glu Met Gln Gln Met Tyr Asp Met Ile Met Gln His
            420                 425                 430

Lys Arg Ala Met Gln Asp Met Gln Leu Leu Trp Glu Lys Ala Val Gln
        435                 440                 445

Gln His Gln His Gly Tyr Asp Ser Asp Glu Glu Val Asp Ser Glu Leu
    450                 455                 460

Gly Thr Trp Glu His Gln Leu Arg Arg Met Glu Met Asp Lys Thr Arg
465                 470                 475                 480

Glu Trp Ala Glu Gln Leu Thr Lys Met Gly Arg Gly Lys His Phe Ile
                485                 490                 495

Gly Asp Phe Leu Pro Pro Asp Glu Leu Glu Lys Phe Met Glu Thr Phe
            500                 505                 510

Lys Ala Leu Lys Glu Gly Arg Glu Pro Asp Tyr Ser Glu Tyr Lys Glu
        515                 520                 525

Phe Lys Leu Thr Val Glu Asn Ile Gly Tyr Gln Met Leu Met Lys Met
    530                 535                 540

Gly Trp Lys Glu Gly Glu Gly Leu Gly Ser Glu Gly Gln Gly Ile Lys
545                 550                 555                 560

Asn Pro Val Asn Lys Gly Thr Thr Thr Val Asp Gly Ala Gly Phe Gly
                565                 570                 575

Ile Asp Arg Pro Ala Glu Leu Ser Lys Glu Asp Asp Glu Tyr Glu Ala
            580                 585                 590

Phe Arg Lys Arg Met Met Leu Ala Tyr Arg Phe Arg Pro Asn Pro Leu
        595                 600                 605

Asn Asn Pro Arg Arg Pro Tyr Tyr
    610                 615

<210> SEQ ID NO 2
<211> LENGTH: 1938
<212> TYPE: DNA
<213> ORGANISM: Homo sapiens

<400> SEQUENCE: 2
atgagtctca agatggacaa ccgggatgtt gcaggaaagg ctaaccggtg gtttgggggtt      60 gctccccta aatctggaaa aatgaacatg aacatccttc accaggaaga gctcatcgct      120
cagaagaaac gggaaattga agccaaaatg aacagaaag ccaagcagaa tcaggtggcc      180
agccctcagc ccccacatcc tggcgaaatc acaaatgcac acaactcttc ctgcatttcc      240
```

-continued

| | |
|---|---|
| aacaagtttg ccaacgatgg tagcttcttg cagcagtttc tgaagttgca gaaggcacag | 300 |
| accagcacag acgccccgac cagtgcgccc agcgcccctc ccagcacacc caccccagc | 360 |
| gctgggaaga ggtccctgct catcagcagg cggacaggcc tggggctggc cagcctgccg | 420 |
| ggccctgtga agagctactc ccacgccaag cagctgcccg tggcgcaccg cccgagtgtc | 480 |
| ttccagtccc ctgacgagga cgaggaggag gactatgagc agtggctgga gatcaaagtt | 540 |
| tcacccccag agggagccga gactcggaaa gtgatagaga aattggcccg ctttgtggca | 600 |
| gaaggaggcc ccgagttaga aaaagtagct atggaggact acaaggataa cccagcattt | 660 |
| gcatttttgc acgataagaa tagcagggaa ttcctctact acaggaagaa ggtggctgag | 720 |
| ataagaaagg aagcacagaa gtcgcaggca gcctctcaga aagtttcacc cccagaggac | 780 |
| gaagaggtca agaaccttgc agaaaagttg gccaggttca tagcggacgg gggtcccgag | 840 |
| gtggaaacca ttgccctcca gaacaaccgt gagaaccagg cattcagctt tctgtatgag | 900 |
| cccaatagcc aagggtacaa gtactaccga cagaagctgg aggagttccg gaaagccaag | 960 |
| gccagctcca caggcagctt cacagcacct gatcccggcc tgaagcgcaa gtcccctcct | 1020 |
| gaggccctgt cagggtcctt accccccagcc accacctgcc ccgcctcgtc cacgcctgcg | 1080 |
| cccactatca tccctgctcc agctgccccc gggaagccag cctccgcagc caccgtgaag | 1140 |
| aggaagcgga agagccggtg ggggcctgaa gaggataagg tagagctcct acctgctgaa | 1200 |
| ctggtgcaga gggacgtgga tgcctctccc tcgcctctgt cagttcagga cctcaagggg | 1260 |
| ctcggctatg agaaggggaa gcctgtgggt ctagtgggcg tcacagagct ttcagacgcc | 1320 |
| cagaagaagc agctgaagga gcagcaggag atgcagcaga tgtacgacat gatcatgcag | 1380 |
| cacaagcggg ccatgcagga catgcagctg ctgtgggaga aggcagtcca acagcaccag | 1440 |
| cacggctatg acagtgatga ggaggtggac agcgagctgg gcacctggga gcaccagctg | 1500 |
| cggcgcatgg agatggataa gaccagggaa tgggccgagc agctgacaaa gatgggccgg | 1560 |
| ggcaagcact tcatcggaga cttcctgcct ccagacgagc tggaaaagtt tatggagacc | 1620 |
| ttcaaggccc tgaaggaggg ccgtgagcct gactactcag agtacaagga gttcaagctg | 1680 |
| actgtggaga acatcggcta ccagatgctg atgaagatgg gctggaagga gggcgagggg | 1740 |
| ctgggctcag agggccaggg catcaagaac ccagtgaaca aggcaccac cacagtggac | 1800 |
| ggcgctggct tcggcattga ccggccggcg gagctctcca aggaggacga cgagtatgag | 1860 |
| gcgttccgca agaggatgat gctggcctac cgcttccggc ccaaccccct gaacaatccc | 1920 |
| agacggcctt actactga | 1938 |

<210> SEQ ID NO 3
<211> LENGTH: 645
<212> TYPE: PRT
<213> ORGANISM: Homo sapiens

<400> SEQUENCE: 3

Met Ser Leu Lys Met Asp Asn Arg Asp Val Ala Gly Lys Ala Asn Arg
1               5                   10                  15

Trp Phe Gly Val Ala Pro Pro Lys Ser Gly Lys Met Asn Met Asn Ile
            20                  25                  30

Leu His Gln Glu Glu Leu Ile Ala Gln Lys Lys Arg Glu Ile Glu Ala
        35                  40                  45

Lys Met Glu Gln Lys Ala Lys Gln Asn Gln Val Ala Ser Pro Gln Pro
    50                  55                  60

-continued

```
Pro His Pro Gly Glu Ile Thr Asn Ala His Asn Ser Ser Cys Ile Ser
 65                  70                  75                  80

Asn Lys Phe Ala Asn Asp Gly Ser Phe Leu Gln Gln Phe Leu Lys Leu
                 85                  90                  95

Gln Lys Ala Gln Thr Ser Thr Asp Ala Pro Thr Ser Ala Pro Ser Ala
            100                 105                 110

Pro Pro Ser Thr Pro Thr Pro Ser Ala Gly Lys Arg Ser Leu Leu Ile
        115                 120                 125

Ser Arg Arg Thr Gly Leu Gly Leu Ala Ser Leu Pro Gly Pro Val Lys
    130                 135                 140

Ser Tyr Ser His Ala Lys Gln Leu Pro Val Ala His Arg Pro Ser Val
145                 150                 155                 160

Phe Gln Ser Pro Asp Glu Asp Glu Glu Asp Tyr Glu Gln Trp Leu
                165                 170                 175

Glu Ile Lys Val Ser Pro Pro Glu Gly Ala Glu Thr Arg Lys Val Ile
                180                 185                 190

Glu Lys Leu Ala Arg Phe Val Ala Glu Gly Pro Glu Leu Glu Lys
            195                 200                 205

Val Ala Met Glu Asp Tyr Lys Asp Asn Pro Ala Phe Ala Phe Leu His
    210                 215                 220

Asp Lys Asn Ser Arg Glu Phe Leu Tyr Tyr Arg Lys Lys Val Ala Glu
225                 230                 235                 240

Ile Arg Lys Glu Ala Gln Lys Ser Gln Ala Ala Ser Gln Lys Val Ser
                245                 250                 255

Pro Pro Glu Asp Glu Val Lys Asn Leu Ala Glu Lys Leu Ala Arg
                260                 265                 270

Phe Ile Ala Asp Gly Gly Pro Glu Val Glu Thr Ile Ala Leu Gln Asn
            275                 280                 285

Asn Arg Glu Asn Gln Ala Phe Ser Phe Leu Tyr Glu Pro Asn Ser Gln
        290                 295                 300

Gly Tyr Lys Tyr Tyr Arg Gln Lys Leu Glu Glu Phe Arg Lys Ala Lys
305                 310                 315                 320

Ala Ser Ser Thr Gly Ser Phe Thr Ala Pro Asp Pro Gly Leu Lys Arg
                325                 330                 335

Lys Ser Pro Pro Glu Ala Leu Ser Gly Ser Leu Pro Pro Ala Thr Thr
            340                 345                 350

Cys Pro Ala Ser Ser Thr Pro Ala Pro Thr Ile Ile Pro Ala Pro Ala
        355                 360                 365

Ala Pro Gly Lys Pro Ala Ser Ala Ala Thr Val Lys Arg Lys Arg Lys
    370                 375                 380

Ser Arg Trp Gly Pro Glu Glu Asp Lys Val Glu Leu Leu Pro Ala Glu
385                 390                 395                 400

Leu Val Gln Arg Asp Val Asp Ala Ser Pro Ser Pro Leu Ser Val Gln
                405                 410                 415

Asp Leu Lys Gly Leu Gly Tyr Glu Lys Gly Lys Pro Val Gly Leu Val
                420                 425                 430

Gly Val Thr Glu Leu Ser Asp Ala Gln Lys Lys Gln Leu Lys Glu Gln
            435                 440                 445

Gln Glu Met Gln Gln Met Tyr Asp Met Ile Met Gln His Lys Arg Ala
        450                 455                 460

Met Gln Asp Met Gln Leu Leu Trp Glu Lys Ala Val Gln Gln His Gln
465                 470                 475                 480

His Gly Tyr Asp Ser Asp Glu Glu Val Asp Ser Glu Leu Gly Thr Trp
```

```
                        485                 490                 495

Glu His Gln Leu Arg Arg Met Glu Met Asp Lys Thr Arg Glu Trp Ala
            500                 505                 510

Glu Gln Leu Thr Lys Met Gly Arg Gly Lys His Phe Ile Gly Asp Phe
            515                 520                 525

Leu Pro Pro Asp Glu Leu Glu Lys Phe Met Glu Thr Phe Lys Ala Leu
            530                 535                 540

Lys Glu Gly Arg Glu Pro Asp Tyr Ser Glu Tyr Lys Gly Phe Lys Leu
545                 550                 555                 560

Thr Val Glu Asn Ile Gly Tyr Gln Met Leu Met Lys Met Gly Trp Lys
                565                 570                 575

Glu Gly Glu Gly Leu Gly Ser Glu Gly Gln Gly Ile Lys Asn Pro Val
            580                 585                 590

Asn Lys Gly Thr Thr Thr Val Asp Gly Ala Gly Phe Gly Ile Asp Arg
            595                 600                 605

Pro Ala Glu Leu Ser Lys Glu Asp Glu Tyr Glu Ala Phe Arg Lys
            610                 615                 620

Arg Met Met Leu Ala Tyr Arg Phe Arg Pro Asn Pro Leu Asn Asn Pro
625                 630                 635                 640

Arg Arg Pro Tyr Tyr
                645

<210> SEQ ID NO 4
<211> LENGTH: 24
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: Peptide derived from Cari

<400> SEQUENCE: 4

Ser Val Gln Asp Leu Lys Gly Leu Gly Tyr Glu Lys Gly Lys Pro Val
1               5                   10                  15

Gly Leu Val Gly Val Thr Glu Leu
            20

<210> SEQ ID NO 5
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: Peptide derived from Cari

<400> SEQUENCE: 5

Gly Tyr Glu Lys Gly Lys Pro Val Gly Leu Val Gly Val Thr Glu Leu
1               5                   10                  15

<210> SEQ ID NO 6
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: anti sense olygo nucleotides to Cari sequence

<400> SEQUENCE: 6
```

-continued

```
aagaggataa ggtagagctc c                                              21

<210> SEQ ID NO 7
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: anti sense olygo nucleotides to Cari sequence

<400> SEQUENCE: 7
aatgaccaac cgtccctgga c                                              21

<210> SEQ ID NO 8
<211> LENGTH: 496
<212> TYPE: PRT
<213> ORGANISM: Artificial
<220> FEATURE:
<223> OTHER INFORMATION: Synthetic
<220> FEATURE:
<221> NAME/KEY: SIGNAL
<222> LOCATION: (1)..(18)
<220> FEATURE:
<221> NAME/KEY: mat_peptide
<222> LOCATION: (19)..(496)

<400> SEQUENCE: 8

Met Asp Phe Ser Arg Asn Leu Tyr Asp Ile Gly Glu Gln Leu Asp Ser
            -15                 -10                  -5

Glu Asp Leu Ala Ser Leu Lys Phe Leu Ser Leu Asp Tyr Ile Pro Gln
 -1   1               5                  10

Arg Lys Gln Glu Pro Ile Lys Asp Ala Leu Met Leu Phe Gln Arg Leu
 15                  20                  25                  30

Gln Glu Lys Arg Met Leu Glu Glu Ser Asn Leu Ser Phe Leu Lys Glu
                 35                  40                  45

Leu Leu Phe Arg Ile Asn Arg Leu Asp Leu Leu Ile Thr Tyr Leu Asn
                 50                  55                  60

Thr Arg Lys Glu Glu Met Glu Arg Glu Leu Gln Thr Pro Gly Arg Ala
 65                  70                  75

Gln Ile Ser Ala Tyr Arg Phe His Phe Cys Arg Met Ser Trp Ala Glu
 80                  85                  90

Ala Asn Ser Gln Cys Gln Thr Gln Ser Val Pro Phe Trp Arg Arg Val
 95                 100                 105                 110

Asp His Leu Leu Ile Arg Val Met Leu Tyr Gln Ile Ser Glu Glu Val
                115                 120                 125

Ser Arg Ser Glu Leu Arg Ser Phe Lys Phe Leu Leu Gln Glu Glu Ile
                130                 135                 140

Ser Lys Cys Lys Leu Asp Asp Met Asn Leu Leu Asp Ile Phe Ile
                145                 150                 155

Glu Met Glu Lys Arg Val Ile Leu Gly Glu Gly Lys Leu Asp Ile Leu
 160                 165                 170

Lys Arg Val Cys Ala Gln Ile Asn Lys Ser Leu Leu Lys Ile Ile Asn
 175                 180                 185                 190

Asp Tyr Glu Glu Phe Ser Lys Gly Glu Glu Leu Cys Gly Val Met Thr
                195                 200                 205

Ile Ser Asp Ser Pro Arg Glu Gln Asp Ser Glu Ser Gln Thr Leu Asp
                210                 215                 220
```

-continued

```
Lys Val Tyr Gln Met Lys Ser Lys Pro Arg Gly Tyr Cys Leu Ile Ile
        225                 230                 235

Asn Asn His Asn Phe Ala Lys Ala Arg Glu Lys Val Pro Lys Leu His
        240                 245                 250

Ser Ile Arg Asp Arg Asn Gly Thr His Leu Asp Ala Gly Ala Leu Thr
255                 260                 265                 270

Thr Thr Phe Glu Glu Leu His Phe Glu Ile Lys Pro His His Asp Cys
            275                 280                 285

Thr Val Glu Gln Ile Tyr Glu Ile Leu Lys Ile Tyr Gln Leu Met Asp
            290                 295                 300

His Ser Asn Met Asp Cys Phe Ile Cys Cys Ile Leu Ser His Gly Asp
        305                 310                 315

Lys Gly Ile Ile Tyr Gly Thr Asp Gly Gln Glu Ala Pro Ile Tyr Glu
        320                 325                 330

Leu Thr Ser Gln Phe Thr Gly Leu Lys Cys Pro Ser Leu Ala Gly Lys
335                 340                 345                 350

Pro Lys Val Phe Phe Ile Gln Ala Cys Gln Gly Asp Asn Tyr Gln Lys
            355                 360                 365

Gly Ile Pro Val Glu Thr Asp Ser Glu Glu Gln Pro Tyr Leu Glu Met
        370                 375                 380

Asp Leu Ser Ser Pro Gln Thr Arg Tyr Ile Pro Asp Glu Ala Asp Phe
        385                 390                 395

Leu Leu Gly Met Ala Thr Val Asn Asn Cys Val Ser Tyr Arg Asn Pro
400                 405                 410

Ala Glu Gly Thr Trp Tyr Ile Gln Ser Leu Cys Gln Ser Leu Arg Glu
415                 420                 425                 430

Arg Cys Pro Arg Gly Asp Asp Ile Leu Thr Ile Leu Thr Glu Val Asn
            435                 440                 445

Tyr Glu Val Ser Asn Lys Asp Asp Lys Lys Asn Met Gly Lys Gln Met
                450                 455                 460

Pro Gln Pro Thr Phe Thr Leu Arg Lys Lys Leu Val Phe Pro Ser Asp
        465                 470                 475
```

<210> SEQ ID NO 9
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: Peptide 182

<400> SEQUENCE: 9

```
Leu Ser Ser Pro Gln Thr Arg Tyr Ile Pro Asp Glu Ala Asp Cys
1               5                   10                  15
```

<210> SEQ ID NO 10
<211> LENGTH: 18
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: Peptide 183

<400> SEQUENCE: 10

```
Ser Glu Ser Gln Thr Leu Asp Lys Val Tyr Gln Met Lys Ser Lys Pro
1               5                   10                  15
```

Arg Cys

```
<210> SEQ ID NO 11
<211> LENGTH: 34
<212> TYPE: DNA
<213> ORGANISM: Artificial
<220> FEATURE:
<223> OTHER INFORMATION: Synthetic

<400> SEQUENCE: 11
ctcaagatgg acaaccggga tgttgcagga aagg                            34

<210> SEQ ID NO 12
<211> LENGTH: 33
<212> TYPE: DNA
<213> ORGANISM: Artificial
<220> FEATURE:
<223> OTHER INFORMATION: Synthetic

<400> SEQUENCE: 12
ccactcgagt cagtagtaag gccgtctggg att                             33

<210> SEQ ID NO 13
<211> LENGTH: 35
<212> TYPE: DNA
<213> ORGANISM: Artificial
<220> FEATURE:
<223> OTHER INFORMATION: Synthetic

<400> SEQUENCE: 13
aatggatcca tgagtctcaa gatggacaac cggga                           35
```